(12) United States Patent
von der Osten et al.

(10) Patent No.: US 6,623,950 B1
(45) Date of Patent: Sep. 23, 2003

(54) MODIFIED ENZYMES HAVING POLYMER CONJUGATES

(75) Inventors: Claus von der Osten, Lyngby (DK); Arne Agerlin Olsen, Virum (DK); Erwin Ludo Roggen, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 124 days.

(21) Appl. No.: 09/705,185

(22) Filed: Nov. 2, 2000

Related U.S. Application Data

(62) Division of application No. 09/024,532, filed on Feb. 17, 1998, now Pat. No. 6,245,901, which is a continuation of application No. PCT/DK98/00046, filed on Feb. 6, 1998.

(30) Foreign Application Priority Data

Feb. 6, 1997 (DK) ............................................... 0135/97

(51) Int. Cl.[7] ............................. C12N 9/50; C12N 9/54; C12N 15/57; C11D 3/386
(52) U.S. Cl. ........................ 435/220; 435/69.1; 435/221; 435/252.3; 435/320.1; 435/471; 536/23.2; 510/320
(58) Field of Search ............................... 435/220, 221, 435/222, 69.1, 471, 320.1, 252.31; 536/23.2; 510/320

(56) References Cited

U.S. PATENT DOCUMENTS

| | | | | |
|---|---|---|---|---|
| 5,340,735 A | * | 8/1994 | Christianson et al. | 435/221 |
| 5,352,603 A | * | 10/1994 | Vetter et al. | 435/221 |
| 5,621,089 A | * | 4/1997 | Sloma et al. | 536/23.2 |
| 5,631,217 A | * | 5/1997 | Branner et al. | 510/320 |
| 5,665,587 A | * | 9/1997 | Aaslyng et al. | 435/221 |
| 5,851,811 A | * | 12/1998 | Welinder et al. | 435/192 |
| 6,197,567 B1 | * | 3/2001 | Aaslyng et al. | 435/221 |

FOREIGN PATENT DOCUMENTS

| | | |
|---|---|---|
| WO | WO 92/10755 | 6/1992 |
| WO | WO 93/15189 | 8/1993 |
| WO | WO 96/17929 | 6/1996 |

OTHER PUBLICATIONS

Hershfield et al., Proc. Natl. Acad. Sci., vol. 88, pp. 7185–7189 (Aug. 1991).

Zalipisky, S., Advanced Drug Delivery Reviews, Vol 16, pp. 157–182 (1995).

* cited by examiner

Primary Examiner—Ponnathapu Achutamurthy
Assistant Examiner—William W. Moore
(74) Attorney, Agent, or Firm—Elias J. Lambiris

(57) ABSTRACT

The present invention relates to polypeptide-polymer conjugates having added and/or removed one or more attachment groups for coupling polymeric molecules on the surface of the polypeptide structure, a method for preparing polypeptide-polymer conjugates of the invention, the use of said conjugates for reducing the immunogenicity and allergenicity and compositions comprising said conjugate.

11 Claims, 1 Drawing Sheet

SEQUENCE LISTING

<160> NUMBER OF SEQ ID NOS: 9

<210> SEQ ID NO 1
<211> LENGTH: 840
<212> TYPE: DNA

```
<213> ORGANISM: bacillus sp.
<220> FEATURE:
<221> NAME/KEY: CDS
<222> LOCATION: (1)...(840)

<400> SEQUENCE: 1 tgg tca ccg aat gac cct tac tat tct gct tac cag tat gga cca caa      48
Trp Ser Pro Asn Asp Pro Tyr Tyr Ser Ala Tyr Gln Tyr Gly Pro Gln
  1               5                  10                  15 aac acc tca acc cct gct gcc tgg gat gta acc cgt gga agc agc act      96
Asn Thr Ser Thr Pro Ala Ala Trp Asp Val Thr Arg Gly Ser Ser Thr
             20                  25                  30 caa acg gtg gcg gtc ctt gat tcc gga gtg gat tat aac cac cct gat     144
Gln Thr Val Ala Val Leu Asp Ser Gly Val Asp Tyr Asn His Pro Asp
         35                  40                  45 ctt gca aga aaa gta ata aaa ggg tac gac ttt atc gac agg gac aat     192
Leu Ala Arg Lys Val Ile Lys Gly Tyr Asp Phe Ile Asp Arg Asp Asn
 50                  55                  60 aac cca atg gat ctt aac gga cat ggt acc cat gtt gcc ggt act gtt     240
Asn Pro Met Asp Leu Asn Gly His Gly Thr His Val Ala Gly Thr Val
 65                  70                  75                  80 gct gct gat acg aac aat gga att ggc gta gcc ggt atg gca cca gat     288
Ala Ala Asp Thr Asn Asn Gly Ile Gly Val Ala Gly Met Ala Pro Asp
                 85                  90                  95 acg aag atc ctt gcc gta cgg gtc ctt gat gcc aat gga agt ggc tca     336
Thr Lys Ile Leu Ala Val Arg Val Leu Asp Ala Asn Gly Ser Gly Ser
            100                 105                 110 ctt gac agc att gcc tca ggt atc cgc tat gct gct gat caa ggg gca     384
Leu Asp Ser Ile Ala Ser Gly Ile Arg Tyr Ala Ala Asp Gln Gly Ala
        115                 120                 125 aag gta ctc aac ctc tcc ctt ggt tgc gaa tgc aac tcc aca act ctt     432
Lys Val Leu Asn Leu Ser Leu Gly Cys Glu Cys Asn Ser Thr Thr Leu
130                 135                 140 aag agt gcc gtc gac tat gca tgg aac aaa gga gct gta gtc gtt gct     480
Lys Ser Ala Val Asp Tyr Ala Trp Asn Lys Gly Ala Val Val Val Ala
145                 150                 155                 160 gct gca ggg aat gac aat gta tcc cgt aca ttc caa cca gct tct tac     528
Ala Ala Gly Asn Asp Asn Val Ser Arg Thr Phe Gln Pro Ala Ser Tyr
                165                 170                 175 cct aat gcc att gca gta ggt gcc att gac tcc aat gat cga aaa gca     576
Pro Asn Ala Ile Ala Val Gly Ala Ile Asp Ser Asn Asp Arg Lys Ala
            180                 185                 190 tca ttc tcc aat tac gga acg tgg gtg gat gtc act gct cca ggt gtg     624
Ser Phe Ser Asn Tyr Gly Thr Trp Val Asp Val Thr Ala Pro Gly Val
        195                 200                 205 aac ata gca tca acc gtt ccg aat aat ggc tac tcc tac atg tct ggt     672
Asn Ile Ala Ser Thr Val Pro Asn Asn Gly Tyr Ser Tyr Met Ser Gly
210                 215                 220 acg tcc atg gca tcc cct cac gtg gcc ggt ttg gct gct ttg ttg gca     720
Thr Ser Met Ala Ser Pro His Val Ala Gly Leu Ala Ala Leu Leu Ala
225                 230                 235                 240 agt caa ggt aag aat aac gta caa atc cgc cag gcc att gag caa acc     768
Ser Gln Gly Lys Asn Asn Val Gln Ile Arg Gln Ala Ile Glu Gln Thr
                245                 250                 255 gcc gat aag atc tct ggc act gga aca aac ttc aag tat ggt aaa atc     816
Ala Asp Lys Ile Ser Gly Thr Gly Thr Asn Phe Lys Tyr Gly Lys Ile
            260                 265                 270 aac tca aac aaa gct gta aga tac                                     840
Asn Ser Asn Lys Ala Val Arg Tyr
        275                 280
```

```
<210> SEQ ID NO 2
<211> LENGTH: 280
<212> TYPE: PRT
<213> ORGANISM: bacillus sp.

<400> SEQUENCE: 2

Trp Ser Pro Asn Asp Pro Tyr Tyr Ser Ala Tyr Gln Tyr Gly Pro Gln
 1               5                  10                  15

Asn Thr Ser Thr Pro Ala Ala Trp Asp Val Thr Arg Gly Ser Ser Thr
             20                  25                  30

Gln Thr Val Ala Val Leu Asp Ser Gly Val Asp Tyr Asn His Pro Asp
         35                  40                  45

Leu Ala Arg Lys Val Ile Lys Gly Tyr Asp Phe Ile Asp Arg Asp Asn
 50                  55                  60

Asn Pro Met Asp Leu Asn Gly His Gly Thr His Val Ala Gly Thr Val
 65                  70                  75                  80

Ala Ala Asp Thr Asn Asn Gly Ile Gly Val Ala Gly Met Ala Pro Asp
                 85                  90                  95

Thr Lys Ile Leu Ala Val Arg Val Leu Asp Ala Asn Gly Ser Gly Ser
             100                 105                 110

Leu Asp Ser Ile Ala Ser Gly Ile Arg Tyr Ala Ala Asp Gln Gly Ala
         115                 120                 125

Lys Val Leu Asn Leu Ser Leu Gly Cys Glu Cys Asn Ser Thr Thr Leu
130                 135                 140

Lys Ser Ala Val Asp Tyr Ala Trp Asn Lys Gly Ala Val Val Val Ala
145                 150                 155                 160

Ala Ala Gly Asn Asp Asn Val Ser Arg Thr Phe Gln Pro Ala Ser Tyr
                 165                 170                 175

Pro Asn Ala Ile Ala Val Gly Ala Ile Asp Ser Asn Asp Arg Lys Ala
             180                 185                 190

Ser Phe Ser Asn Tyr Gly Thr Trp Val Asp Val Thr Ala Pro Gly Val
         195                 200                 205

Asn Ile Ala Ser Thr Val Pro Asn Asn Gly Tyr Ser Tyr Met Ser Gly
    210                 215                 220

Thr Ser Met Ala Ser Pro His Val Ala Gly Leu Ala Ala Leu Leu Ala
225                 230                 235                 240

Ser Gln Gly Lys Asn Asn Val Gln Ile Arg Gln Ala Ile Glu Gln Thr
                 245                 250                 255

Ala Asp Lys Ile Ser Gly Thr Gly Thr Asn Phe Lys Tyr Gly Lys Ile
             260                 265                 270

Asn Ser Asn Lys Ala Val Arg Tyr
    275                 280

<210> SEQ ID NO 3
<211> LENGTH: 269
<212> TYPE: PRT
<213> ORGANISM: Bacillus lentus

<400> SEQUENCE: 3

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
         35                  40                  45
```

```
Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 4
<211> LENGTH: 344
<212> TYPE: PRT
<213> ORGANISM: Arthromyces ramosus

<400> SEQUENCE: 4

Gln Gly Pro Gly Gly Gly Gly Ser Val Thr Cys Pro Gly Gly Gln
1               5                   10                  15

Ser Thr Ser Asn Ser Gln Cys Cys Val Trp Phe Asp Val Leu Asp Asp
                20                  25                  30

Leu Gln Thr Asn Phe Tyr Gln Gly Ser Lys Cys Glu Ser Pro Val Arg
            35                  40                  45

Lys Ile Leu Arg Ile Val Phe His Asp Ala Ile Gly Phe Ser Pro Ala
    50                  55                  60

Leu Thr Ala Ala Gly Gln Phe Gly Gly Gly Ala Asp Gly Ser Ile
65                  70                  75                  80

Ile Ala His Ser Asn Ile Glu Leu Ala Phe Pro Ala Asn Gly Gly Leu
                85                  90                  95

Thr Asp Thr Ile Glu Ala Leu Arg Ala Val Gly Ile Asn His Gly Val
            100                 105                 110

Ser Phe Gly Asp Leu Ile Gln Phe Ala Thr Ala Val Gly Met Ser Asn
        115                 120                 125

Cys Pro Gly Ser Pro Arg Leu Glu Phe Leu Thr Gly Arg Ser Asn Ser
    130                 135                 140

Ser Gln Pro Ser Pro Pro Ser Leu Ile Pro Gly Pro Gly Asn Thr Val
145                 150                 155                 160
```

-continued

```
Thr Ala Ile Leu Asp Arg Met Gly Asp Ala Gly Phe Ser Pro Asp Glu
            165                 170                 175
Val Val Asp Leu Leu Ala Ala His Ser Leu Ala Ser Gln Glu Gly Leu
            180                 185                 190
Asn Ser Ala Ile Phe Arg Ser Pro Leu Asp Ser Thr Pro Gln Val Phe
            195                 200                 205
Asp Thr Gln Phe Tyr Ile Glu Thr Leu Leu Lys Gly Thr Thr Gln Pro
            210                 215                 220
Gly Pro Ser Leu Gly Phe Ala Glu Glu Leu Ser Pro Phe Pro Gly Glu
225                 230                 235                 240
Phe Arg Met Arg Ser Asp Ala Leu Leu Ala Arg Asp Ser Arg Thr Ala
            245                 250                 255
Cys Arg Trp Gln Ser Met Thr Ser Ser Asn Glu Val Met Gly Gln Arg
            260                 265                 270
Tyr Arg Ala Ala Met Ala Lys Met Ser Val Leu Gly Phe Asp Arg Asn
            275                 280                 285
Ala Leu Thr Asp Cys Ser Asp Val Ile Pro Ser Ala Val Ser Asn Asn
            290                 295                 300
Ala Ala Pro Val Ile Pro Gly Gly Leu Thr Val Asp Asp Ile Glu Val
305                 310                 315                 320
Ser Cys Pro Ser Glu Pro Phe Pro Glu Ile Ala Thr Ala Ser Gly Pro
            325                 330                 335
Leu Pro Ser Leu Ala Pro Ala Pro
            340
```

<210> SEQ ID NO 5
<211> LENGTH: 876
<212> TYPE: DNA
<213> ORGANISM: Humicola lanuginosa DSM 4109
<220> FEATURE:
<221> NAME/KEY: CDS
<222> LOCATION: (1)...(876)
<221> NAME/KEY: sig_peptide
<222> LOCATION: (1)...(66)
<221> NAME/KEY: mat_peptide
<222> LOCATION: (67)...(876)

<400> SEQUENCE: 5

```
atg agg agc tcc ctt gtg ctg ttc ttt gtc tct gcg tgg acg gcc ttg      48
Met Arg Ser Ser Leu Val Leu Phe Phe Val Ser Ala Trp Thr Ala Leu
        -20                 -15                 -10 gcc agt cct att cgt cga gag gtc tcg cag gat ctg ttt aac cag ttc      96
Ala Ser Pro Ile Arg Arg Glu Val Ser Gln Asp Leu Phe Asn Gln Phe
    -5                   1               5                  10 aat ctc ttt gca cag tat tct gca gcc gca tac tgc gga aaa aac aat     144
Asn Leu Phe Ala Gln Tyr Ser Ala Ala Ala Tyr Cys Gly Lys Asn Asn
                15                  20                  25 gat gcc cca gct ggt aca aac att acg tgc acg gga aat gcc tgc ccc     192
Asp Ala Pro Ala Gly Thr Asn Ile Thr Cys Thr Gly Asn Ala Cys Pro
            30                  35                  40 gag gta gag aag gcg gat gca acg ttt ctc tac tcg ttt gaa gac tct     240
Glu Val Glu Lys Ala Asp Ala Thr Phe Leu Tyr Ser Phe Glu Asp Ser
        45                  50                  55 gga gtg ggc gat gtc acc ggc ttc ctt gct ctc gac aac acg aac aaa     288
Gly Val Gly Asp Val Thr Gly Phe Leu Ala Leu Asp Asn Thr Asn Lys
    60                  65                  70 ttg atc gtc ctc tct ttc cgt ggc tct cgt tcc ata gag aac tgg atc     336
Leu Ile Val Leu Ser Phe Arg Gly Ser Arg Ser Ile Glu Asn Trp Ile
75                  80                  85                  90
```

```
ggg aat ctt aac ttc gac ttg aaa gaa ata aat gac att tgc tcc ggc     384
Gly Asn Leu Asn Phe Asp Leu Lys Glu Ile Asn Asp Ile Cys Ser Gly
             95                 100                 105 tgc agg gga cat gac ggc ttc act tcg tcc tgg agg tct gta gcc gat     432
Cys Arg Gly His Asp Gly Phe Thr Ser Ser Trp Arg Ser Val Ala Asp
        110                 115                 120 acg tta agg cag aag gtg gag gat gct gtg agg gag cat ccc gac tat     480
Thr Leu Arg Gln Lys Val Glu Asp Ala Val Arg Glu His Pro Asp Tyr
            125                 130                 135 cgc gtg gtg ttt acc gga cat agc ttg ggt ggt gca ttg gca act gtt     528
Arg Val Val Phe Thr Gly His Ser Leu Gly Gly Ala Leu Ala Thr Val
        140                 145                 150 gcc gga gca gac ctg cgt gga aat ggg tat gat atc gac gtg ttt tca     576
Ala Gly Ala Asp Leu Arg Gly Asn Gly Tyr Asp Ile Asp Val Phe Ser
155                 160                 165                 170 tat ggc gcc ccc cga gtc gga aac agg gct ttt gca gaa ttc ctg acc     624
Tyr Gly Ala Pro Arg Val Gly Asn Arg Ala Phe Ala Glu Phe Leu Thr
                175                 180                 185 gta cag acc ggc gga aca ctc tac cgc att acc cac acc aat gat att     672
Val Gln Thr Gly Gly Thr Leu Tyr Arg Ile Thr His Thr Asn Asp Ile
            190                 195                 200 gtc cct aga ctc ccg ccg cgc gaa ttc ggt tac agc cat tct agc cca     720
Val Pro Arg Leu Pro Pro Arg Glu Phe Gly Tyr Ser His Ser Ser Pro
        205                 210                 215 gag tac tgg atc aaa tct gga acc ctt gtc ccc gtc acc cga aac gat     768
Glu Tyr Trp Ile Lys Ser Gly Thr Leu Val Pro Val Thr Arg Asn Asp
220                 225                 230 atc gtg aag ata gaa ggc atc gat gcc acc ggc ggc aat aac cag cct     816
Ile Val Lys Ile Glu Gly Ile Asp Ala Thr Gly Gly Asn Asn Gln Pro
235                 240                 245                 250 aac att ccg gat atc cct gcg cac cta tgg tac ttc ggg tta att ggg     864
Asn Ile Pro Asp Ile Pro Ala His Leu Trp Tyr Phe Gly Leu Ile Gly
                255                 260                 265 aca tgt ctt tag                                                     876
Thr Cys Leu *

<210> SEQ ID NO 6
<211> LENGTH: 291
<212> TYPE: PRT
<213> ORGANISM: Humicola lanuginosa DSM 4109
<220> FEATURE:
<221> NAME/KEY: SIGNAL
<222> LOCATION: (1)...(22)

<400> SEQUENCE: 6

Met Arg Ser Ser Leu Val Leu Phe Phe Val Ser Ala Trp Thr Ala Leu
        -20                 -15                 -10

Ala Ser Pro Ile Arg Arg Glu Val Ser Gln Asp Leu Phe Asn Gln Phe
     -5                   1               5                  10

Asn Leu Phe Ala Gln Tyr Ser Ala Ala Tyr Cys Gly Lys Asn Asn
                 15                  20                  25

Asp Ala Pro Ala Gly Thr Asn Ile Thr Cys Thr Gly Asn Ala Cys Pro
                30                  35                  40

Glu Val Glu Lys Ala Asp Ala Thr Phe Leu Tyr Ser Phe Glu Asp Ser
            45                  50                  55

Gly Val Gly Asp Val Thr Gly Phe Leu Ala Leu Asp Asn Thr Asn Lys
        60                  65                  70

Leu Ile Val Leu Ser Phe Arg Gly Ser Arg Ser Ile Glu Asn Trp Ile
75                  80                  85                  90
```

-continued

```
Gly Asn Leu Asn Phe Asp Leu Lys Glu Ile Asn Asp Ile Cys Ser Gly
                 95                 100                 105

Cys Arg Gly His Asp Gly Phe Thr Ser Ser Trp Arg Ser Val Ala Asp
             110                 115                 120

Thr Leu Arg Gln Lys Val Glu Asp Ala Val Arg Glu His Pro Asp Tyr
             125                 130                 135

Arg Val Val Phe Thr Gly His Ser Leu Gly Gly Ala Leu Ala Thr Val
     140                 145                 150

Ala Gly Ala Asp Leu Arg Gly Asn Gly Tyr Asp Ile Asp Val Phe Ser
155                 160                 165                 170

Tyr Gly Ala Pro Arg Val Gly Asn Arg Ala Phe Ala Glu Phe Leu Thr
             175                 180                 185

Val Gln Thr Gly Gly Thr Leu Tyr Arg Ile Thr His Thr Asn Asp Ile
             190                 195                 200

Val Pro Arg Leu Pro Pro Arg Glu Phe Gly Tyr Ser His Ser Ser Pro
             205                 210                 215

Glu Tyr Trp Ile Lys Ser Gly Thr Leu Val Pro Val Thr Arg Asn Asp
     220                 225                 230

Ile Val Lys Ile Glu Gly Ile Asp Ala Thr Gly Gly Asn Asn Gln Pro
235                 240                 245                 250

Asn Ile Pro Asp Ile Pro Ala His Leu Trp Tyr Phe Gly Leu Ile Gly
             255                 260                 265

Thr Cys Leu

<210> SEQ ID NO 7
<211> LENGTH: 32
<212> TYPE: DNA
<213> ORGANISM: R28K oligo

<400> SEQUENCE: 7
gggatgtaac caagggaagc agcactcaaa cg                                    32

<210> SEQ ID NO 8
<211> LENGTH: 27
<212> TYPE: DNA
<213> ORGANISM: R169K oligo

<400> SEQUENCE: 8
cgactttatc gataaggaca ataaccc                                          27

<210> SEQ ID NO 9
<211> LENGTH: 27
<212> TYPE: DNA
<213> ORGANISM: R169K oligo

<400> SEQUENCE: 9
caatgtatcc aaaacgttcc aaccagc                                          27
```

MODIFIED ENZYMES HAVING POLYMER CONJUGATES

CROSS-REFERENCE TO RELATED APPLICATIONS

Figure 1:
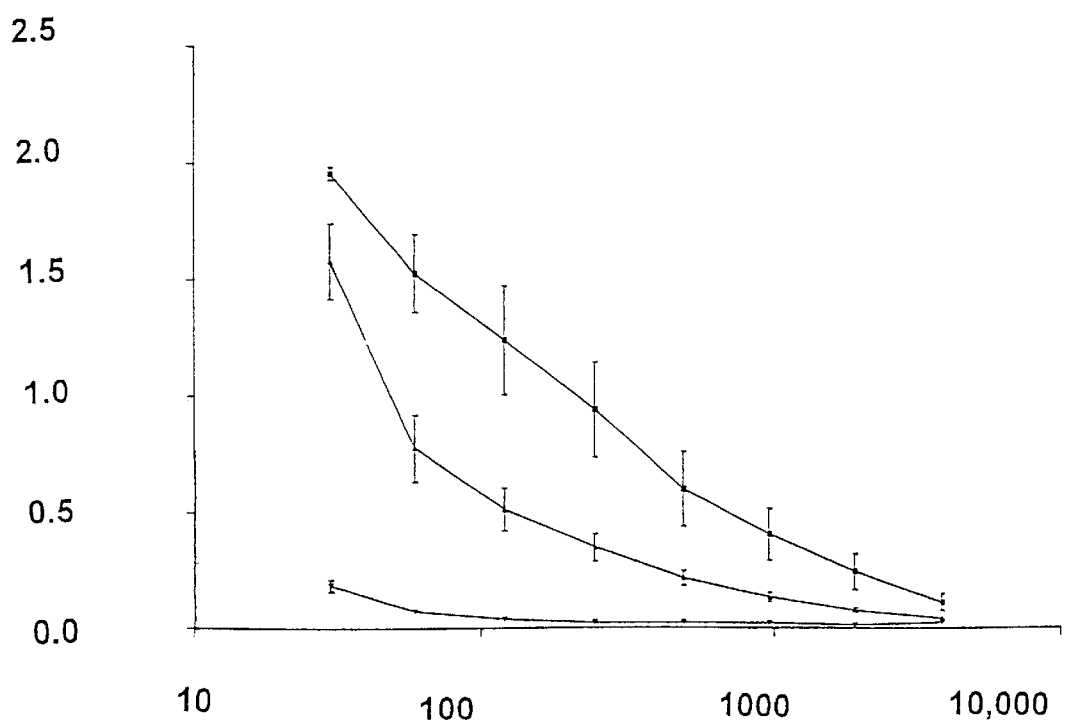

This application is a divisional of application Ser. No. 09/024,532 filed on Feb. 17, 1998, now U.S. Pat. No. 6,245,901, which is a continuation of PCT/DK98/00046 filed on Feb. 6, 1998, and claims priority under 35 U.S.C. 119 of Danish application no. 0135/97 filed Feb. 6, 1997, the contents of which are fully incorporated herein by reference.

FIELD OF THE INVENTION

The present invention relates to polypeptide-polymer conjugates having added and/or removed one or more attachment groups for coupling polymeric molecules on the surface of the 3D structure of the polypeptide, a method for preparing polypeptide-polymer conjugates of the invention, the use of said conjugated for reducing the immunogenicity and allergenicity, and compositions comprising said conjugate.

BACKGROUND OF THE INVENTION

The use of polypeptides, including enzymes, in the circulatory system to obtain a particular physiological effect is well-known in the medical arts. Further, within the arts of industrial applications, such as laundry washing, textile bleaching, person care, contact lens cleaning, food and feed preparation enzymes are used as a functional ingredient. One of the important differences between pharmaceutical and industrial application is that for the latter type of applications (i.e. industrial applications) the polypeptides (often enzymes) are not intended to enter into the circulatory system of the body.

Certain polypeptides and enzymes have an unsatisfactory stability and may under certain circumstances—dependent on the way of challenge—cause an immune response, typically an IgG and/or IgE response.

It is today generally recognized that the stability of polypeptides is improved and the immune response is reduced when polypeptides, such as enzymes, are coupled to polymeric molecules. It is believed that the reduced immune response is a result of the shielding of (the) epitope(s) on the surface of the polypeptide responsible for the immune response leading to antibody formation by the coupled polymeric molecules.

Techniques for conjugating polymeric molecules to polypeptides are well-known in the art.

One of the first commercially suitable techniques was described back in the early 1970's and disclosed in e.g. U.S. Pat. No. 4,179,337. Said patent concerns non-immunogenic polypeptides, such as enzymes and peptide hormones coupled to polyethylene glycol (PEG) or polypropylene glycol (PPG). At least 15% of polypeptides' physiological activity is maintained.

GB patent no. 1,183,257 (Crook et al.) describes chemistry for conjugation of enzymes to polysaccharides via a triazine ring.

Further, techniques for maintaining of the enzymatic activity of enzyme-polymer conjugates are also known in the art.

WO 93/15189 (Veronese et al.) concerns a method for maintaining the activity in polyethylene glycol-modified proteolytic enzymes by linking the proteolytic enzyme to a macromolecularized inhibitor. The conjugates are intended for medical applications.

It has been found that the attachment of polymeric molecules to a polypeptide often has the effect of reducing the activity of the polypeptide by interfering with the interaction between the polypeptide and its substrate. EP 183 503 (Beecham Group PLC) discloses a development of the above concept by providing conjugates comprising pharmaceutically useful proteins linked to at least one water-soluble polymer by means of a reversible linking group.

EP 471,125 (Kanebo) discloses skin care products comprising a parent protease (Bacillus protease with the trade name Esperase®) coupled to polysaccharides through a triazine ring to improve the thermal and preservation stability. The coupling technique used is also described in the above mentioned GB patent no. 1,183,257 (Crook et al.).

JP 3083908 describes a skin cosmetic material which contains a transglutaminase from guinea pig liver modified with one or more water-soluble, substances such as PEG, starch, cellulose etc. The modification is performed by activating the polymeric molecules and coupling them to the enzyme. The composition is stated to be mild to the skin.

However, it is not always possible to readily couple polymeric molecules to polypeptides and enzymes. Further, there is still a need for polypeptide-polymer conjugates with an even more reduced immunogenicity and/or allergenicity.

SUMMARY OF THE INVENTION

It is the object of the present invention to provide improved polypeptide-polymer conjugates suitable for industrial and pharmaceutical applications.

The term "improved polypeptide-polymer conjugates" means in the context of the present invention conjugates having a reduced immune response in humans and animals and/or a improved stability. As will be described further below the immune response is dependent on the way of challenge.

The present inventors have found that polypeptides, such as enzymes, may be made less immunogenic and/or allergenic by adding and/or removing one or more attachment groups on the surface of the parent polypeptide to be coupled to polymeric molecules.

When introducing pharmaceutical polypeptide directly into the circulatory system (i.e. bloodstream) the potential risk is an immunogenic response in the form of mainly IgG, IgA and/or IgM antibodies. In contrast hereto, industrial polypeptides, such as enzymes used as a functional ingredient in e.g. detergents, are not intended to enter the circulatory system. The potential risk in connection with industrial polypeptides is inhalation causing an allergenic response in the form of mainly IgE antibody formation.

Therefore, in connection with industrial polypeptides the potential risk is respiratory allergenicity caused by inhalation, intratracheal and intranasal presentation of polypeptides.

The main potential risk of pharmaceutical polypeptides is immunogenicity caused by, intradermal, intravenous, or subcutaneous presentation of the polypeptide.

It is to be understood that reducing the "immunogenicity" and reducing the "respiratory allergenicity" are two very different problems based on different routes of exposure and on two very different immunological mechanisms:

The term "immunogenicity" used in connection with the present invention may be referred to as allergic contact dermatitis in a clinical setting and is a cell mediated delayed immune response to chemicals that contact and penetrate the skin. This cell mediated reaction is also termed delayed contact hypersensitivity (type IV reaction according to Gell and Combs classification of immune mechanisms in tissue damage).

The term "allergenicity" or "respiratory allergenicity" is an immediate anaphylactic reaction (type I antibody-mediated reaction according to Gell and Combs) following inhalation of e.g. polypeptides.

According to the present invention it is possible to provide polypeptides with a reduced immune response and/or improved stability, which has a substantially retained residual activity.

The allergic and the immunogenic response are in one term, at least in the context of the present invention called the "immune response".

In the first aspect the invention relates to a polypeptide-polymer conjugate having a) one or more additional polymeric molecules coupled to the polypeptide having been modified in a manner to increase the number of attachment groups on the surface of the polypeptide in comparison to the number of attachment groups available on the corresponding parent polypeptide, and/or b) one or more fewer polymeric molecules coupled to the polypeptide having been modified in a manner to decrease the number of attachment groups at or close to the functional site(s) of the polypeptide in comparison to the number of attachment groups available on the corresponding parent polypeptide.

The term "parent polypeptide" refers to the polypeptide to be modified by coupling to polymeric molecules. The parent polypeptide may be a naturally-occurring (or wild-type) polypeptide or may be a variant thereof prepared by any suitable means. For instance, the parent polypeptide may be a variant of a naturally-occurring polypeptide which has been modified by substitution, deletion or truncation of one or more amino acid residues or by addition or insertion of one or more amino acid residues to the amino acid sequence of a naturally-occurring polypeptide.

A "suitable attachment group" means in the context of the present invention any amino acid residue group on the surface of the polypeptide capable of coupling to the polymeric molecule in question.

Preferred attachment groups are amino groups of Lysine residues and the N-terminal amino group. Polymeric molecules may also be coupled to the carboxylic acid groups (—COOH) of amino acid residues in the polypeptide chain located on the surface. Carboxylic acid attachment groups may be the carboxylic acid group of Aspartate or Glutamate and the C-terminal COOH-group.

A "functional site" means any amino acid residues and/or cofactors which are known to be essential for the performance of the polypeptide, such as catalytic activity, e.g. the catalytic triad residues, Histidine, Aspartate and Serine in Serine proteases, or e.g. the heme group and the distal and proximal Histidines in a peroxidase such as the *Arthromyces ramosus* peroxidase.

In the second aspect the invention relates to a method for preparing improved polypeptide-polymer conjugates comprising the steps of:

a) identifying amino acid residues located on the surface of the 3D structure of the parent polypeptide in question, b) selecting target amino acid residues on the surface of said 3D structure of said parent polypeptide to be mutated, c) i) substituting or inserting one or more amino acid residues selected in step b) with an amino acid residue having a suitable attachment group, and/or ii) substituting or deleting one or more amino acid residues selected in step b) at or close to the functional site(s), d) coupling polymeric molecules to the mutated polypeptide.

The invention also relates to the use of a conjugate of the invention and the method of the invention for reducing the immunogenicity of pharmaceuticals and reducing the allergenicity of industrial products.

Finally the invention relates to compositions comprising a conjugate of the invention and further ingredients used in industrial products or pharmaceuticals.

BRIEF DESCRIPTION OF THE DRAWING

FIG. 1 shows the anti-lipase serum antibody levels after 5 weekly immunizations with i) control ii) unmodified lipase variant, iii) lipase variant-SPEG. (X: log(serum dilution); Y optical Density (490/620)).

DETAILED DESCRIPTION OF THE INVENTION

It is the object of the present invention to provide improved polypeptide-polymer conjugates suitable for industrial and pharmaceutical applications.

Even though polypeptides used for pharmaceutical applications and industrial application can be quite different the principle of the present invention may be tailored to the specific type of parent polypeptide (i.e. enzyme, hormone peptides etc.).

The inventors of the present invention have provided improved polypeptide-polymer conjugates with a reduced immune response in comparison to conjugates prepared from the corresponding parent polypeptides.

The present inventors have found that polypeptides, such as enzymes, may be made less immunogenic and/or less allergenic by adding one or more attachment groups on the surface of the parent polypeptide. In addition thereto the inventors have found that a higher percentage of maintained residual functional activity may be obtained by removing attachment groups at or close to the functional site(s).

In the first aspect the invention relates to an improved polypeptide-polymer conjugate having a) one or more additional polymeric molecules coupled to the polypeptide having been modified in a manner to increase the number of attachment groups on the surface of the polypeptide in comparison to the number of attachment groups available on the corresponding parent polypeptide, and/or b) one or more fewer polymeric molecules coupled to the polypeptide having been modified in a manner to decrease the number of attachment groups at or close to the functional site(s) of the polypeptide in comparison to the number of attachment groups available on the corresponding parent polypeptide.

Whether the attachment groups should be added and/or removed depends on the specific parent polypeptide.

a) Addition of Attachment Groups

There may be a need for further attachment groups on the polypeptide if only few attachment groups are available on the surface of the parent polypeptide. The addition of one or more attachment groups by substituting or inserting one or more amino acid residues on the surface of the parent polypeptide increases the number of polymeric molecules which may be attached in comparison to the corresponding parent polypeptide. Conjugates with an increased number of polymeric molecules attached thereto are generally seen to have a reduced immune response in comparison to the corresponding conjugates having fewer polymeric molecules coupled thereto.

Any available amino acid residues on the surface of the polypeptide, preferentially not being at or close to the functional site(s), such as the active site(s) of enzymes, may in principle be subject to substitution and/or insertion to provide additional attachment groups.

As will be described further below the location of the additional coupled polymeric molecules may be of importance for the reduction of the immune response and the percentage of maintained residual functional activity of the polypeptide itself.

A conjugate of the invention may typically have from 1 to 25, preferentially 1 to 10 or more additional polymeric molecules coupled to the surface of the polypeptide in comparison to the number of polymeric molecules of a conjugate prepared on the basis of the corresponding parent polypeptide.

However, the optimal number of attachment groups to be added depends (at least partly) on the surface area (i.e. molecular weight) of the parent polypeptide to be shielded by the coupled polymeric molecules, and also on the number of already available attachment groups on the parent polypeptide.

b) Removing Attachment Groups

In the case of enzymes or other polypeptides performing their function by interaction with a substrate or the like, polymeric molecules coupled to the polypeptide might be impeded by the interaction between the polypeptide and its substrate or the like, if they are coupled at or close to the functional site(s) (i.e. active site of enzymes). This will most probably cause reduced activity.

In the case of enzymes having one or more polymeric molecules coupled at or close to the active site a substantial loss of residual enzymatic activity can be expected. Therefore, according to the invention conjugates may be constructed to maintain a higher percentage of residual enzymatic activity in comparison to a corresponding conjugates prepared on the basis of the parent enzyme in question. This may be done by substituting and/or deleting attachment groups at or close to the active site, hereby increasing the substrate affinity by improving the accessibility of the substrate in the catalytic cleft.

An enzyme-polymer conjugate of the invention may typically have from 1 to 25, preferably 1 to 10 fewer polymeric molecules coupled at or close to the active site in comparison to the number of polymeric molecules of a conjugate prepared on the basis of the corresponding parent polypeptide.

As will be explained below "at or close to" the functional site(s) means that no polymeric molecule(s) should be coupled within 5 Å, preferably 8 Å, especially 10 Å of the functional site(s).

Removal of attachment groups at or close to the functional site(s) of the polypeptide may advantageously be combined with addition of attachment groups in other parts of the surface of the polypeptide.

The total number of attachment groups may this way be unchanged, increased or decreased. However the location(s) of the total number of attachment group(s) is (are) improved assessed by the reduction of the immune response and/or percentage of maintained residual activity. Improved stability may also be obtained this way.

The Number of Attachment Groups

Generally seen the number of attachment groups should be balanced to the molecular weight and/or surface area of the polypeptide. The more heavy the polypeptide is the more polymeric molecules should be coupled to the polypeptide to obtain sufficient shielding of the epitope(s) responsible for antibody formation.

Therefore, if the parent polypeptide molecule is relatively light (e.g. 1 to 35 kDa) it may be advantageous to increase the total number of coupled polymeric molecules (outside the functional site(s)) to a total between 4 and 20.

If the parent polypeptide molecules is heavier, for instance 35 to 60 kDa, the number of coupled polymeric molecules (outside the functional site(s)) may advantageously be increased to 7 to 40, and so on.

The ratio between the molecular weight (Mw) of the polypeptide in question and the number of coupled polymeric molecules considered to be suitable by the inventors is listed below in Table 1.

TABLE 1

| Molecular weight of parent polypeptide ($M_w$) kDa | Number of polymeric molecules coupled to the polypeptide |
| --- | --- |
| 1 to 35 | 4–20 |
| 35 to 60 | 7–40 |
| 60 to 80 | 10–50 |
| 80 to 100 | 15–70 |
| more than 100 | more than 20 |

Reduced Immune Response vs. Maintained Residual Enzymatic Activity

Especially for enzymes, in comparison to many other types of polypeptides, there is a conflict between reducing the immune response and maintaining a substantial residual enzymatic activity as the activity of enzymes are connected with interaction between a substrate and the active site often present as a cleft in the enzyme structure.

Without being limited to any theory it is believed that the loss of enzymatic activity of enzyme-polymer conjugates might be a consequence of impeded access of the substrate to the active site in the form of spatial hindrance of the substrate by especially bulky and/or heavy polymeric molecules to the catalytic cleft. It might also, at least partly, be caused by disadvantageous minor structural changes of the 3D structure of the enzyme due to the stress made by the coupling of the polymeric molecules.

Maintained Residual Activity

A polypeptide-polymer conjugates of the invention has a substantially maintained functional activity.

A "substantially" maintained functional activity is in the context of the present invention defined as an activity which is at least between 20% and 30%, preferably between 30% and 40%, more preferably between 40% and 60%, better from 60% up to 80%, even better from 80% up to about 100%, in comparison to the activity of the conjugates prepared on the basis of corresponding parent polypeptides.

In the case of polypeptide-polymer conjugates of the invention where no polymeric molecules are coupled at or close to the functional site(s) the residual activity may even be up to 100% or very close thereto. If attachment group(s) of the parent polypeptide is(are) removed from the functional site the activity might even be more than 100% in comparison to modified (i.e. polymer coupled) parent polypeptide conjugate.

Position of Coupled Polymeric Molecules

To obtain an optimally reduced immune response (i.e. immunogenic and allergenic response) the polymeric molecules coupled to the surface of the polypeptide in question should be located in a suitable distance from each other.

In a preferred embodiment of the invention the parent polypeptide is modified in a manner whereby the polymeric molecules are spread broadly over the surface of the polypeptide. In the case of the polypeptide in question has enzymatic activity it is preferred to have as few as possible, especially none, polymeric molecules coupled at or close to the area of the active site.

In the present context "spread broadly over the surface of the polypeptide" means that the available attachment groups are located so that the polymeric molecules shield different parts of the surface, preferably the whole or close to the whole surface area away from the functional site(s), to make sure that epitope(s) are shielded and hereby not recognized by the immune system or its antibodies.

The area of antibody-polypeptide interaction typically covers an area of 500 $Å^2$, as described by Sheriff et al. (1987), Proc. Natl. Acad. Sci. USA 84, p. 8075–8079. 500 $Å^2$ corresponds to a rectangular box of 25 Å×20 Å or a circular region of radius 12.6 Å. Therefore, to prevent binding of antibodies to the epitope(s) to the polypeptide in question it is preferred to have a maximum distance between two attachment groups around 10 Å.

Consequently, amino acid residues which are located in excess of 10 Å away from already available attachment groups are suitable target residues. If two or more attachment groups on the polypeptide are located very close to each other it will in most cases result in that only one polymeric molecule will be coupled.

To ensure a minimal loss of functional activity it is preferred not to couple polymeric molecules at or close to the functional site(s). Said distance depends at least partly on the bulkiness of the polymeric molecules to be coupled, as impeded access by the bulky polymeric molecules to the functional site is undesired. Therefore, the more bulky the polymeric molecules are the longer should the distance from the functional site to the coupled polymeric molecules be.

To maintain a substantial functional activity of the polypeptide in question attachment groups located within 5 Å, preferred 8 Å, especially 10 Å from such functional site(s) should be left uncoupled and may therefore advantageously be removed or changed by mutation. Functional residues should normally not be mutated/removed, even though they potentially can be the target for coupling polymeric molecules. In said case it may thus be advantageous to choose a coupling chemistry involving different attachment groups.

Further, to provide a polypeptide having coupled polymeric molecules at (a) known epitope(s) recognizable by the immune system or close to said epitope(s) specific mutations at such sites are also considered advantageous according to the invention. If the position of the epitope(s) is(are) unknown it is advantageous to couple several or many polymeric molecules to the polypeptide.

As also mentioned above it is preferred that said attachment groups are spread broadly over the surface.

The Attachment Group

Virtually all ionized groups, such as the amino groups of Lysine residues, are located on the surface of the polypeptide molecule (see for instance Thomas E. Creighton, (1993), "Proteins", W. H. Freeman and Company, New York).

Therefore, the number of readily accessible attachment groups (e.g. amino groups) on a modified or parent polypeptide equals generally seen the number of Lysine residues in the primary structure of the polypeptide plus the N-terminus amino group.

The chemistry of coupling polymeric molecules to amino groups are quite simple and well established in the art. Therefore, it is preferred to add and/or remove Lysine residues (i.e. attachment groups) to/from the parent polypeptide in question to obtain improved conjugates with reduced immunogenicity and/or allergenicity and/or improved stability and/or high percentage maintained functional activity.

Polymeric molecules may also be coupled to the carboxylic groups (—COOH) of amino acid residues on the surface of the polypeptide. Therefore, if using carboxylic groups (including the C-terminal group) as attachment groups addition and/or removal of Aspartate and Glutamate residues may also be suitable according to the invention.

If using other attachment groups, such as —SH groups, they may be added and/or removed analogously.

Substitution of the amino acid residues is preferred over insertion, as the impact on the 3D structure of the polypeptide normally will be less pronounced.

Preferred substitutions are conservative substitutions. In the case of increasing the number of attachment groups the substitution may advantageously be performed at a location having a distance of 5 Å, preferred 8 Å, especially 10 Å from the functional site(s) (active site for enzymes).

An example of a suitable conservative substitution to obtain an additional amino attachment group is an Arginine to Lysine substitution. Examples of conservative substitutions to obtain additional carboxylic attachment groups are Aspargine to Aspartate/Glutamate or Glutamine to Aspartate/Glutamate substitutions. To remove attachment groups a Lysine residue may be substituted with an Arginine and so on.

The Parent Polypeptide

In the context of the present invention the term "polypeptides" includes proteins, peptides and/or enzymes for pharmaceutical or industrial applications. Typically the polypeptides in question have a molecular weight in the range between about 1 to 100 kDa, often 15 kDa and 100 kDa.

Pharmaceutical Polypeptides

The term "pharmaceutical polypeptides" is defined as polypeptides, including peptides, such as peptide hormones, proteins and/or enzymes, being physiologically active when introduced into the circulatory system of the body of humans and/or animals.

Pharmaceutical polypeptides are potentially immunogenic as they are introduced into the circulatory system.

Examples of "pharmaceutical polypeptides" contemplated according to the invention include insulin, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, antidiuretic hormones, thyroid stimulating hormone, relaxin, interferon, thrombopoietin (TPO) and prolactin.

Industrial Polypeptides

Polypeptides used for industrial applications often have an enzymatic activity. Industrial polypeptides (e.g. enzymes) are (in contrast to pharmaceutical polypeptides) not intended to be introduced into the circulatory system of the body.

It is not very like that industrial polypeptides, such as enzymes used as ingredients in industrial compositions and/or products, such as detergents and personal care products, including cosmetics, come into direct contact with the circulatory system of the body of humans or animals, as such enzymes (or products comprising such enzymes) are not injected (or the like) into the bloodstream.

Therefore, in the case of the industrial polypeptide the potential risk is respiratory allergy (i.e. IgE response) as a consequence of inhalation to polypeptides through the respiratory passage.

In the context of the present invention "industrial polypeptides" are defined as polypeptides, including peptides, proteins and/or enzymes, which are not intended to be introduced into the circulatory system of the body of humans and/or animals.

Examples of such polypeptides are polypeptides, especially enzymes, used in products such as detergents, household article products, agrochemicals, personal care products, such as skin care products, including cosmetics and toiletries, oral and dermal pharmaceuticals, composition use for processing textiles, compositions for hard surface cleaning, and compositions used for manufacturing food and feed etc.

Enzymatic Activity

Pharmaceutical or industrial polypeptides exhibiting enzymatic activity will often belong to one of the following groups of enzymes including Oxidoreductases (E.C. 1, "Enzyme Nomenclature, (1992), Academic Press, Inc.), such as laccase and Superoxide dismutase (SOD); Transferases, (E.C. 2), such as transglutaminases (TGases); Hydrolases (E.C. 3), including proteases, especially subtilisins, and lipolytic enzymes; Isomerases (E.C. 5), such as Protein disulfide Isomerases (PDI).

Hydrolases

Proteolytic Enzymes

Contemplated proteolytic enzymes include proteases selected from the group of Aspartic proteases, such pepsins, Cysteine proteases, such as Papain, Serine proteases, such as subtilisins, or metallo proteases, such as NEUTRASE®.

Specific examples of parent proteases include PD498 (WO 93/24623 and SEQ ID NO. 2), SAVINASE® (von der Osten et al., (1993), Journal of Biotechnology, 28, p. 55+, SEQ ID NO 3), Proteinase K (Gunkel et al., (1989), Eur. J. Biochem, 179, p. 185–194), Proteinase R (Samal et al, (1990), Mol. Microbiol, 4, p. 1789–1792), Proteinase T (Samal et al., (1989), Gene, 85, p. 329–333), Subtilisin DY (Betzel et al. (1993), Arch. Biophys, 302, no. 2, p. 499–502), Lion Y (JP 04197182-A), RENNILASE® (Available from Novo Nordisk A/S), JA16 (WO 92/17576), ALCALASE® (a natural subtilisin Carlberg variant) (von der Osten et al., (1993), Journal of Biotechnology, 28, p. 55+).

Lipolytic Enzymes

Contemplated lipolytic enzymes include *Humicola lanuginosa* lipases, e.g. the one described in EP 258 068 and EP 305 216 (See SEQ ID NO 6 below), *Humicola insolens*, a *Rhizomucor miehei* lipase, e.g. as described in EP 238 023, Absidia sp. lipolytic enzymes (WO 96/13578), a *Candida lipase*, such as a *C. antarctica* lipase, e.g. the *C. antarctica* lipase A or B described in EP 214 761, a *Pseudomonas lipase* such as a *P. alcaligenes* and *P. pseudoalcaligenes* lipase, e.g. as described in EP 218 272, a *P. cepacia* lipase, e.g. as described in EP 331 376, a Pseudomonas sp. lipase as disclosed in WO 95/14783, a *Bacillus lipase*, e.g. a *B. subtilis* lipase (Dartois et al., (1993) Biochemica et Biophysica acta 1131, 253–260), a *B. stearothermophilus* lipase (JP 64/744992) and a *B. pumilus* lipase (WO 91/16422). Other types of lipolytic enzymes include cutinases, e.g. derived from *Pseudomonas mendocina* as described in WO 88/09367, or a cutinase derived from *Fusarium solani* pisi (e.g. described in WO 90/09446).

Oxidoreductases

Laccases

Contemplated laccases include *Polyporus pinisitus* laccase (WO 96/00290), *Myceliophthora laccase* (WO 95/33836) *Scytalidium laccase* (WO 95/338337), and *Pyricularia oryzae* laccase (Available from Sigma).

Peroxidase

Contemplated peroxidases include *B. pumilus* peroxidases (WO 91/05858), *Myxococcaceae peroxidase* (WO 95/11964), *Coprinus cinereus* (WO 95/10602) and *Arthromyces ramosus* peroxidase (Kunishima et al. (1994), J. Mol. Biol. 235, p. 331–344).

Transferases

Transglutaminases

Suitable transferases include any transglutaminases disclosed in WO 96/06931 (Novo Nordisk A/S) and WO 96/22366 (Novo Nordisk A/S).

Isomerases

Protein Disulfide Isomerase

Without being limited thereto suitable protein disulfide isomerases include PDIs described in WO 95/01425 (Novo Nordisk A/S).

The Polymeric Molecule

The polymeric molecules coupled to the polypeptide may be any suitable polymeric molecule, including natural and synthetic homo-polymers, such as polyols (i.e. poly-OH), polyamines (i.e. poly-$NH_2$) and polycarboxyl acids (i.e. poly—COOH), and further hetero-polymers i.e. polymers comprising one or more different coupling groups e.g. a hydroxyl group and amine groups.

Examples of suitable polymeric molecules include polymeric molecules selected from the group comprising polyalkylene oxides (PAO), such as polyalkylene glycols (PAG), including polyethylene glycols (PEG), methoxypolyethylene glycols (mPEG) and polypropylene glycols, PEG-glycidyl ethers (Epox-PEG), PEG-oxycarbonylimidazole (CDI-PEG), branched PEGS, poly-vinyl alcohol (PVA), poly-carboxylates, polyvinlypyrrlidone poly-D,L-amino acids, polyethylene-co-maleic acid anhydride, polystyrene-co-malic acid anhydride dextrans including carboxymethyl-dextrans, heparin, homologous albumin, celluloses, including methylcellulose, carboxymethylcellulose, ethylcellulose, hydroxyethylcellulose carboxyethylcellulose and hydroxypropylcellulose, hydrolysates of chitosan, starches such as hydroxyethyl-starches and hydroxy propyl-starches, glycogen, agaroses and derivatives thereof, guar gum, pullulan, inulin, xanthan gum, carrageenin, pectin, alginic acid hydrolysates and bio-polymers.

Preferred polymeric molecules are non-toxic polymeric molecules such as (m)polyethylene glycol ((m)PEG) which further requires a relatively simple chemistry for its covalently coupling to attachment groups on the enzyme's surface.

Generally seen polyalkylene oxides (PAO), such as polyethylene oxides, such as PEG and especially mPEG, are the preferred polymeric molecules, as these polymeric molecules, in comparison to polysaccharides such as dextran, pullulan and the like, have few reactive groups capable of cross-linking.

Even though all of the above mentioned polymeric molecules may be used according to the invention the methoxypolyethylene glycols (mPEG) may advantageously be used. This arises from the fact that methoxyethylene glycols have only one reactive end capable of conjugating with the enzyme. Consequently, the risk of cross-linking is less pronounced. Further, it makes the product more homogeneous and the reaction of the polymeric molecules with the enzyme easier to control.

Preparation of Enzyme Variants

Enzyme variants to be conjugated may be constructed by any suitable method. A number of methods are well established in the art. For instance enzyme variants according to the invention may be generated using the same materials and methods described in e.g. WO 89/06279 (Novo Nordisk A/S), EP 130,756 (Genentech), EP 479,870 (Novo Nordisk A/S), EP 214,435 (Henkel), WO 87/b4461 (Amgen), WO 87/05050 (Genex), EP application no. 87303761 (Genentech), EP 260,105 (Genencor), WO 88/06624 (Gist-Brocades NV), WO 88/07578 (Genentech), WO 88/08028 (Genex), WO 88/08033 (Amgen), WO 88/08164 (Genex), Thomas et al. (1985) Nature, 318 375–376; Thomas et al. (1987) J. Mol. Biol., 193, 803–813; Russel and Fersht (1987) Nature 328 496–500.

Generation of Site Directed Mutations

Prior to mutagenesis the gene encoding the polypeptide of interest must be cloned in a suitable vector. Methods for generating mutations in specific sites is described below.

Once the polypeptide encoding gene has been cloned, and desirable sites for mutation identified and the residue to substitute for the original ones have been decided, these mutations can be introduced using synthetic oligonucleotides.

These oligonucleotides contain nucleotide sequences flanking the desired mutation sites; mutant nucleotides are inserted during oligo-nucleotide synthesis. In a preferred method, Site-directed mutagenesis is carried out by SOE-PCR mutagenesis technique described by Kammann et al. (1989) Nucleic Acids Research 17(13), 5404, and by Sarkar G. and Sommer, S. S. (1990); Biotechniques 8, 404–407.

Activation of Polymers

If the polymeric molecules to be conjugated with the polypeptide in question are not active it must be activated by the use of a suitable technique. It is also contemplated according to the invention to couple the polymeric molecules to the polypeptide through a linker. Suitable linkers are well-known to the skilled person.

Methods and chemistry for activation of polymeric molecules as well as for conjugation of polypeptides are intensively described in the literature. Commonly used methods for activation of insoluble polymers include activation of functional groups with cyanogen bromide, periodate, glutaraldehyde, biepoxides, epichlorohydrin, divinylsulfone, carbodiimide, sulfonyl halides, trichlorotriazine etc. (see R. F. Taylor, (1991), "Protein immobilization Fundamentals and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). Some of the methods concern activation of insoluble polymers but are also applicable to activation of soluble polymers e.g. periodate, trichlorotriazine, sulfonylhalides, divinylsulfone, carbodiimide etc. The functional groups being amino, hydroxyl, thiol, carboxyl, aldehyde or sulfydryl on the polymer and the chosen attachment group on the protein must be considered in choosing the activation and conjugation chemistry which normally consist of i) activation of polymer, ii) conjugation, and iii) blocking of residual active groups.

In the following a number of suitable polymer activation methods will be described shortly. However, it is to be understood that also other methods may be used.

Coupling polymeric molecules to the free acid groups of poly-peptides may be performed with the aid of diimide and for example amino-PEG or hydrazino-PEG (Pollak et al., (1976), J. Amr. Chem. Soc., 98, 289–291) or diazoacetate/amide (Wong et al., (1992), "Chemistry of Protein Conjugation and Crosslinking", CRC Press).

Coupling polymeric molecules to hydroxy groups are generally very difficult as it must be performed in water. Usually hydrolysis predominates over reaction with hydroxyl groups.

Coupling polymeric molecules to free sulfhydryl groups can be reached with special groups like maleimido or the ortho-pyridyl disulfide. Also vinylsulfone (U.S. Pat. No. 5,414,135, (1995), Snow et al.) has a preference for sulfhydryl groups but is not as selective as the other mentioned.

Accessible Arginine residues in the polypeptide chain may be targeted by groups comprising two vicinal carbonyl groups.

Techniques involving coupling electrophilically activated PEGs to the amino groups of Lysines may also be useful. Many of the usual leaving groups for alcohols give rise to an amine linkage. For instance, alkyl sulfonates, such as tresylates (Nilsson et al., (1984), Methods in Enzymology vol. 104, Jacoby, W. B., Ed., Academic Press: Orlando, p. 56–66; Nilsson et al., (1987), Methods in Enzymology vol. 135; Mosbach, K., Ed.; Academic Press: Orlando, pp. 65–79; Scouten et al., (1987), Methods in Enzymology vol. 135, Mosbach, K., Ed., Academic Press: Orlando, 1987; pp 79–84; Crossland et al., (1971), J. Amr. Chem. Soc. 1971, 93, pp. 4217–4219), mesylates (Harris, (1985), supra; Harris et al., (1984), J. Polym. Sci. Polym. Chem. Ed. 22, pp 341–352), aryl sulfonates like tosylates, and para-nitrobenzene sulfonates can be used.

Organic sulfonyl chlorides, e.g. Tresyl chloride, effectively converts hydroxy groups in a number of polymers, e.g. PEG, into good leaving groups (sulfonates) that, when reacted with nucleophiles like amino groups in polypeptides allow stable linkages to be formed between polymer and polypeptide. In addition to high conjugation yields, the reaction conditions are in general mild (neutral or slightly alkaline pH, to avoid denaturation and little or no disruption of activity), and satisfy the non-destructive requirements to the polypeptide.

Tosylate is more reactive than the mesylate but also more unstable decomposing into PEG, dioxane, and sulfonic acid (zalipsky, (1995), Bioconjugate Chem., 6, 150–165). Epoxides may also been used for creating amine bonds but are much less reactive than the above mentioned groups.

Converting PEG into a chloroformate with phosgene gives rise to carbamate linkages to Lysines. This theme can be played in many variants substituting the chlorine with N-hydroxy succinimide (U.S. Pat. No. 5,122,614, (1992); Zalipsky et al., (1992), Biotechnol. Appl. Biochem., 15, p. 100–114; Monfardini et al., (1995), Bioconjugate Chem., 6, 62–69, with imidazole (Allen et al., (1991), Carbohydr. Res., 213, pp 309–319), with para-nitrophenol, DMAP (EP 632 082 A1, (1993), Looze, Y.) etc. The derivatives are usually made by reacting the chloroformate with the desired leaving group. All these groups give rise.to carbamate linkages to the peptide.

Furthermore, isocyanates and isothiocyanates may be employed yielding ureas and thioureas, respectively.

Amides may be obtained from PEG acids using the same leaving groups as mentioned above and cyclic imide thrones (U.S. Pat. No. 5,349,001, (1994), Greenwald et al.). The reactivity of these compounds are very high but may make the hydrolysis to fast.

PEG succinate made from reaction with succinic anhydride can also be used. The hereby comprised ester group make the conjugate much more susceptible to hydrolysis (U.S. Pat. No. 5,122,614, (1992), Zalipsky). This group may be activated with N-hydroxy succinimide.

Furthermore, a special linker can be introduced. The oldest being cyanuric chloride (Abuchowski et al., (1977), J. Biol. Chem., 252, 3578–3581; U.S. Pat. No. 4,179,337, (1979), Davis et al.; Shafer et al., (1986), J. Polym. Sci. Polym. Chem. Ed., 24, 375–378.

Coupling of PEG to an aromatic amine followed by, diazotization yields a very reactive diazonium salt which in situ can be reacted with a peptide. An amide linkage may also be obtained by reacting an azlactone derivative of PEG (U.S. Pat. No. 5,321,095, (1994), Greenwald, R. B.) thus introducing an additional amide linkage.

As some peptides do not comprise many Lysines it may be advantageous to attach more than one PEG to the same Lysine. This can be done e.g. by the use of 1,3-diamino-2-propanol.

PEGs may also be attached to the amino-groups of the enzyme with carbamate linkages (WO 95111924, Greenwald et al.). Lysine residues may also be used as the backbone.

The coupling technique used in the examples is, the N-succinimidyl carbonate conjugation technique, described in WO 90/13590 (Enzon).

Method for Preparing Improved Conjugates

It is also an object of the invention to provide a method for preparing improved polypeptide-polymer conjugates comprising the steps of:

a) identifying amino acid residues located on the surface of the 3D structure of the parent polypeptide in question, b) selecting target amino acid residues on the surface of said 3D structure of said parent polypeptide to be mutated, c) i) substituting or inserting one or more amino acid residues selected in step b) with an amino acid residue having a suitable attachment group, and/or ii) substituting or deleting one or more amino acid residues selected in step b) at or close to the functional site(s), d) coupling polymeric molecules to the mutated polypeptide.

Step a) Identifyinq Amino Acid Residues Located on the Surface of the Parent Polypeptide 3-dimensional Structure (3D-structure)

To perform the method of the invention a 3-dimensional structure of the parent polypeptide in question is required. This structure may for example be an X-ray structure, an NMR structure or a model-built structure. The Brookhaven Databank is a source of X-ray- and NMR-structures.

A model-built structure may be produced by the person skilled in the art if one or more 3D-structure(s) exist(s) of homologous polypeptide(s) sharing at least 30% sequence identity with the polypeptide in question. Several software packages exist which may be employed to construct a model structure. One example is the Homology 95.0 package from Biosym.

Typical actions required for the construction of a model structure are: alignment of homologous sequences for which 3D-structures exist, definition of Structurally Conserved Regions (SCRs), assignment of coordinates to SCRs, search for structural fragments/loops in structure databases to replace Variable Regions, assignment of coordinates to these regions, and structural refinement by energy minimization. Regions containing large inserts (≧3 residues) relative to the known 3D-structures are known to be quite difficult to model, and structural predictions must be considered with care.

Having obtained the 3D-structure of the polypeptide in question, or a model of the structure based on homology to known structures, this structure serves as an essential prerequisite for the fulfillment of the method described below.

Step b) Selection of Target Amino Acid Residues for Mutation

Target amino acid residues to be mutated are according to the invention selected in order to obtain additional or fewer attachment groups, such as free amino groups (—$NH_2$) or free carboxylic acid groups (—COOH), on the surface of the polypeptide and/or to obtain a more complete and broadly spread shielding of the epitope(s) on the surface of the polypeptide.

Conservative Substitution

It is preferred to make conservative substitutions in the polypeptide, as conservative substitutions secure that the impact of the mutation on the polypeptide structure is limited.

In the case of providing additional amino groups this may be done by substitution of Arginine to Lysine, both residues being positively charged, but only the Lysine having a free amino group suitable as an attachment group.

In the case of providing additional carboxylic acid groups the conservative substitution may for instance be an Aspargine to Aspartic acid or Glutamine to Glutamic acid substitution. These residues resemble each other in size and shape, except from the carboxylic groups being present on the acidic residues.

In the case of providing fewer attachment groups, e.g. at or close to the active site, a Lysine may be substituted with an Arginine, and so on.

Which amino acids to substitute depends in principle on the coupling chemistry to be applied.

Non-conservative Substitution

The mutation may also be on target amino acid residues which are less/non-conservative. Such mutation is suitable for obtaining a more complete and broadly spread shielding of the polypeptide surface than can be obtained by the conservative substitutions.

The method of the invention is first described in general terms, and subsequently using specific examples.

Note the use of the following terms:

Attachment_residue: residue(s) which can bind polymeric molecules, e.g. Lysines (amino group) or Aspartic/Glutamic acids (carboxylic groups). N- or C-terminal amino/carboxylic groups are to be included where relevant. Mutation_residue: residue(s) which is to be mutated, e.g. Arginine or Aspargine/Glutamine. Essential_catalytic_residues: residues which are known to be essential for catalytic function, e.g. the catalytic triad in Serine proteases. Solvent_exposed_residues: These are defined as residues which are at least 5% exposed according to the BIOSYM/INSIGHT algorithm found in the module Homology 95.0. The sequence of commands are as follows:

Homology=>ProStat=>Access_Surf=>Solv_Radius 1.4; Heavy atoms only; Radii source VdW; Output: Fractional Area; Polarity source: Default. The file filename_area.tab is produced. Note: For this program to function properly all water molecules must first be removed from the structure. It looks for example like:

| # PD498FINALMODEL | |
|---|---|
| # residue | area |
| TRP_1 | 136.275711 |
| SER_2 | 88.188095 |
| PRO_3 | 15.458788 |
| ASN_4 | 95.322319 |
| ASP_5 | 4.903404 |
| PRO_6 | 68.096909 |
| TYR_7 | 93.333252 |
| TYR_8 | 31.791576 |
| SER_9 | 95.983139 |
| . . . continued | |

1. Identification of residues which are more than 10 Å away from the closest attachment_residue, and which are located at least 8 Å away from essential_catalytic_residues. This residue subset is called REST, and is the primary region for conservative mutation_residue to attachment_residue substitutions.
2. Identification of residues which are located in a 0–5 Å shell around subset REST, but at least 8 Å away from essential_catalytic_residues. This residue subset is called SUB5B. This is a secondary region for conservative mutation_residue to attachment_residue substitutions, as a ligand bound to an attachment_residue in SUB5B will extend into the REST region and potentially prevent epitope recognition.
3. Identification of solvent_exposed mutation_residues in REST and SUB5B as potential mutation sites for introduction of attachment_residues.
4. Use BIOSYM/INSIGHT's Biopolymer module and replace residues identified under action 3.
5. Repeat 1–2 above producing the subset RESTx. This subset includes residues which are more than 10 Å away from the nearest attachment_residue, and which are located at least 8 Å away from essential catalytic residues.
6 Identify solvent_exposed_residues in RESTx. These are potential sites for less/non-conservative mutations to introduce attachment_residues.

Step c) Substituting, Inserting or Deleting Amino Acid Residues

The mutation(s) performed in step c) may be performed by standard techniques well known in the art, such as site-directed mutagenesis (see, e.g., Sambrook et al. (1989), Sambrook et al., Molecular Cloning. A Laboratory Manual, Cold Spring Harbor, N.Y.

A general description of nucleotide substitution can be found in e.g. Ford et al., 1991, Protein Expression and Purification 2, p. 95–107.

Step d) Coupling Polymeric Molecules to the Modified Parent Enzyme

Polypeptide-polymer conjugates of the invention may be prepared by any coupling method known in the art including the above mentioned techniques.

Coupling of Polymeric Molecules to the Polypeptide in Question

If the polymeric molecules to be conjugated with the polypeptide are not active it must be activated by the use of a suitable method. The polymeric molecules may be coupled to the polypeptide through a linker. Suitable linkers are well known to the skilled person.

Methods and chemistry for activation of polymeric molecules as well as for conjugation of polypeptides are intensively described in the literature. Commonly used methods for activation of insoluble polymers include activation of functional groups with cyanogen bromide, periodate, glutaraldehyde biepoxides, epichlorohydrin, divinylsulfone, carbodiimide, sulfonyl halides, trichlorotriazine etc. (see R. F. Taylor, (1991), "Protein immobilization, Fundamentals and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). Some of the methods concern activation of insoluble polymers but are also applicable to activation of soluble polymers e.g. periodate, trichlorotriazine, sulfonylhalides, divinylsulfone, carbodiimide etc. The functional groups being amino, hydroxyl, thiol, carboxyl, aldehyde or sulfydryl on the polymer and the chosen attachment group on the protein must be considered in choosing the activation and conjugation chemistry which normally consist of i) activation of polymer, ii) conjugation, and iii) blocking of residual active groups.

In the following a number of suitable polymer activation methods will be described shortly. However, it is to be understood that also other methods may be used.

Coupling polymeric molecules to the free acid groups of enzymes can be performed with the aid of diimide and for example amino-PEG or hydrazino-PEG (Pollak et al., (1976), J. Amr. Chem. Soc., 98, 289–291) or diazoacetate/amide (Wong et al., (1992), "Chemistry of Protein Conjugation and Crosslinking", CRC Press).

Coupling polymeric molecules to hydroxy groups are generally very difficult as it must be performed in water. Usually hydrolysis predominates over reaction with hydroxyl groups.

Coupling polymeric molecules to free sulfhydryl groups can be reached with special groups like maleimido or the ortho-pyridyl disulfide. Also vinylsulfone (U.S. Pat. No. 5,414,135, (1995), Snow et al.) has a preference for sulfhydryl groups but is not as selective as the other mentioned.

Accessible Arginine residues in the polypeptide chain may be targeted by groups comprising two vicinal carbonyl groups.

Techniques involving coupling electrophilically activated PEGs to the amino groups of Lysines are also be useful. Many of the usual leaving groups for alcohols give rise to an amine linkage. For instance, alkyl sulfonates, such as tresylates (Nilsson et al., (1984), Methods in Enzymology vol. 104, Jacoby, W. B., Ed., Academic Press: Orlando, p. 56–66; Nilsson et al., (1987), Methods in Enzymology vol. 135; Mosbach, K., Ed.; Academic Press: Orlando, pp. 65–79; Scouten et al., (1987), Methods in Enzymology vol. 135, Mosbach, K., Ed., Academic Press: Orlando, 1987; pp 79–84; Crossland et al., (1971), J. Amr. Chem. Soc. 1971, 93, pp. 4217–4219), mesylates (Harris, (1985), supra; Harris et al., (1984), J. Polym. Sci. Polym. Chem. Ed. 22, pp. 341–352), aryl sulfonates like tosylates, and para-nitrobenzene sulfonates can be used.

Organic sulfonyl chlorides, e.g. Tresyl chloride, effectively converts hydroxy groups in a number of polymers, e.g. PEG, into good leaving groups (sulfonates) that, when reacted with nucleophiles like amino groups in polypeptides allow stable linkages to be formed between polymer and polypeptide. In addition to high conjugation yields, the reaction conditions are in general mild (neutral or slightly alkaline pH, to avoid denaturation and little or no disruption of activity), and satisfy the non-destructive requirements to the polypeptide.

Tosylate is more reactive than the mesylate but also more unstable decomposing into PEG, dioxane, and sulfonic acid (Zalipsky, (1995), Bioconjugate Chem., 6, 150–165).

Epoxides may also been used for creating amine bonds but are much less reactive than the above mentioned groups.

Converting PEG into a chloroformate with phosgene gives rise to carbamate linkages to Lysines. This theme can be played in many variants substituting the chlorine with N-hydroxy succinimide (U.S. Pat. No. 5,122,614, (1992); Zalipsky et al., (1992), Biotechnol. Appl. Biochem., 15, p. 100–114; Monfardini et al., (1995), Bioconjugate Chem., 6, 62–69, with imidazole (Allen et al., (1991), Carbohydr. Res., 213, pp 309–319), with para-nitrophenol, DMAP (EP 632 082 A1, (1993), Looze, Y.) etc. The derivatives are usually made by reacting the chloroformate with the desired leaving group. All these groups give rise to carbamate linkages to the peptide.

Furthermore, isocyanates and isothiocyanates may be employed yielding ureas and thioureas, respectively.

Amides may be obtained from PEG acids using the same leaving groups as mentioned above and cyclic imide thrones (U.S. Pat. No. 5,349,001, (1994), Greenwald et al.). The reactivity of these compounds are very high but may make the hydrolysis to fast.

PEG succinate made from reaction with succinic anhydride can also be used. The hereby comprised ester group make the conjugate much more susceptible to hydrolysis (U.S. Pat. No. 5,122,614, (1992), Zalipsky). This group may be activated with N-hydroxy succinimide.

Furthermore, a special linker can be introduced. The oldest being cyanuric chloride (Abuchowski et al., (1977), J. Biol. Chem., 252, 3578–3581; U.S. Pat. No. 4,179,337, (1979), Davis et al.; Shafer et al., (1986), J. Polym. Sci. Polym. Chem. Ed., 24, 375–378.

Coupling of PEG to an aromatic amine followed by diazotization yields a very reactive diazonium salt which in situ can be reacted with a peptide. An amide linkage may also be obtained by reacting an azlactone derivative of PEG (U.S. Pat. No. 5,321,095, (1994), Greenwald, R. B.) thus introducing an additional amide linkage.

As some peptides do not comprise many Lysines it may be advantageous to attach more than one PEG to the same Lysine. This can be done e.g. by the use of 1,3-diamino-2-propanol.

PEGs may also be attached to the amino-groups of the enzyme with carbamate linkages (WO 95/11924, Greenwald et al.). Lysine residues may also be used as the backbone.

Addition of Attachment Groups
Specific Examples of PD498 Variant-SPEG Conjugates A specific example of a protease is the parent PD498 (WO 93/24623 and SEQ ID NO. 2). The parent PD498 has a molecular weight of 29 kDa.
Lysine and Arginine Residues are Located as Follows:

| Distance from the active site | Arginine | Lysine |
|---|---|---|
| 0–5 Å | 1 | |
| 5–10 Å | | |
| 10–15 Å | 5 | 6 |
| 15–20 Å | 2 | 3 |
| 20–25 Å | 1 | 3 |
| total | 9 | 12 |

The inventors examined which parent PD498 sites on the surface may be suitable for introducing additional attachment groups.

A. Suitable conservative Arginine to Lysine substitutions in parent PD498 may be any of R51K, R62K, R121K, R169K, R250K, R28K, R190K.

B. Suitable non-conservative substitutions in parent PD498 may be any of P6K, Y7K, S9K, A10K, Y11K, Q12K, D43K, Y44K, N45K, N65K, G87K, I88K, N209K, A211K, N216K, N217K, G218K, Y219K, S220K, Y221K, G262K.

As there is no Lysine residues at or close to the active site there is no need for removing any attachment group.

PD498 variant-SPEG conjugates may be prepared using any of the above mentioned PD498 variants as the starting material by any conjugation technique known in the art for coupling polymeric molecules to amino groups on the enzyme. A specific example is described below.

Removal of Attachment Groups
Specific Examples of BPN' Variant-SPEG Conjugates

A specific example of a protease having an attachment group in the active site is BPN' which has 11 attachment groups (plus an N-terminal amino group): BPN' has a molecular weight of 28 kDa.
Lysine and Arginine Residues are Located as Follows:

| Distance from the active site | Arginine | Lysine |
|---|---|---|
| 0–5 Å | | 1 |
| 5–10 Å | | |
| 10–15 Å | 1 | 4 |
| 15–20 Å | 1 | 4 |
| 20–25 Å | — | 2 |
| total | 2 | 11 |

The Lysine residue located within 0–5 Å of the active site can according to the invention advantageously be removed. Specifically this may be done by a K94R substitution.

BPN' variant-SPEG conjugates may be prepared using the above mentioned BPN' variant as the starting material by any conjugation technique known in the art for coupling polymeric molecules to amino groups on the enzyme.

Addition and Removal of Attachment Groups
Specific Example of SAVINASE®-SPEG Conjugate As described in Example 2 parent SAVINASE® (von der Osten et al., (1993), Journal of Biotechnology, 28, p. 55+ and SEQ ID NO. 3) may according to the invention have added a number of amino attachment groups to the surface and removed an amino attachment group close to the active site.

Any of the following substitutions in the parent SAVINASE® are sites for mutagenesis: R10K, R19K, R45K, R145K, R170K, R186K and R247K.

The substitution K94R are identified as a mutation suitable for preventing attachment of polymers close to active site. SAVINASE® variant-SPEG conjugates may be prepared using any of the above mentioned SAVINASE® variants as the starting material by any conjugation technique known in the art for coupling polymeric molecules to amino groups on the enzyme.

Addition of Attachment Groups
A Specific Examples of *Humicola Lanuginosa* Lipase Variants-SPEG Conjugates Specific examples of lipase variants with reduced immunogenicity using the parent *Huminocal lanuginosa* DSM 4109 lipase (see SEQ ID No 6) as the backbone for substitutions are listed below.

The parent unmodified *Humicola lanuginosa* lipase has 8 attachment groups including the N-terminal $NH_2$ group and a molecular weight of about 29 kDa. A. Suitable conservative Arginine to Lysine substitutions in the parent lipase may be any of R133K, R139K, R160K, R179K, R209K, R118K and R125K.

Suitable non-conservative substitutions in the parent lipase may be any of:

A18K,G31K,T32K,N33K,G38K,A40K,D48K,T50K, E56K,D57K,S58K,G59K, V60K, G61K,D62K,T64K, L78K,N88K,G91K,N92K,L93K,S105K,G106K, V120K,P136K,G225K,L227K,V228K,P229K,P250K, F262K.

Further suitable non-conservative substitution in the *Humicola lanuginosa* lipase include: E87K or D254K.

Lipase variant-SPEG conjugates may be prepared using any of the above mentioned lipase variants as the starting material by any conjugation technique known in the art for coupling polymeric molecules to amino groups on the enzyme. A specific example is described below.

In Example 12 below it is shown that a conjugate of the *Humicola lanuginosa* lipase variant with a E87K+D254K substitutions coupled to S-PEG 15,000 has reduced immunogenic response in Balb/C mice in comparison to the corresponding parent unmodified enzyme.

Immunogenicity and Allergenicity

"Immunogenicity" is a broader term than "antigenicity" and "allergenicity", and expresses the immune system's response to the presence of foreign substances. Said foreign substances are called immunogens, antigens and allergens depending of the type of immune response they elicit.

An "immunogen" may be defined as a substance which, when introduced into circulatory system of animals and humans, is capable of stimulating an immunologic response resulting in formation of immunoglobulin.

The term "antigen" refers to substances which by themselves are capable of generating antibodies when recognized as a non-self molecule.

Further, an "allergen" may be defined as an antigen which may give rise to allergic sensitization or an allergic response by IgE antibodies (in humans, and molecules with comparable effects in animals).

Assessment of Immunogencity

Assessment of the immunogenicity may be made by injecting animal subcutaneously to enter the immunogen into the circulation system and comparing the response with the response of the corresponding parent polypeptide.

The "circulatory system" of the body of humans and animals means, in the context of the present invention, the system which mainly consists of the heart and blood vessels. The heart delivers the necessary energy for maintaining blood circulation in the vascular system. The circulation system functions as the organism's transportation system, when the blood transports $O_2$, nutritious matter, hormones, and other substances of importance for the cell regulation into the tissue. Further the blood removes $CO_2$ from the tissue to the lungs and residual substances to e.g. the kidneys. Furthermore, the blood is of importance for the temperature regulation and the defense mechanisms of the body, which include the immune system.

A number of in vitro animal models exist for assessment of the immunogenic potential of polypeptides. Some of these models give a suitable basis for hazard assessment in man. Suitable models include a mice model.

This model, seeks to identify the immunogenic response in the form of the IgG response in Balb/C mice being injected subcutaneously with modified and unmodified polypeptides.

Also other animal models can be used for assessment of the immunogenic potential.

A polypeptide having "reduced immunogenicity" according to the invention indicates that the amount of produced antibodies, e.g. immunoglobulin in humans, and molecules with comparable effects in specific animals, which can lead to an immune response, is significantly decreased, when introduced into the circulatory system, in comparison to the corresponding parent polypeptide.

For Balb/C mice the IgG response gives a good indication of the immunigenic potential of polypeptides.

Assessment of Allergenicity

Assessment of allergenicity may be made by inhalation tests, comparing the effect of intratracheally (into the trachea) administrated parent enzymes with the corresponding modified enzymes according to the invention.

A number of in vivo animal models exist for assessment of the allegenicity of enzymes. Some of these models give a suitable basis for hazard assessment in man. Suitable models include a guinea pig model and a mouse model. These models seek to identify respiratory allergens as a function of elicitation reactions induced in previously sensitized animals. According to these models the alleged allergens are introduced intratracheally into the animals.

A suitable strain of guinea pigs, the Dunkin Hartley strain, do not as humans, produce IgE antibodies in connection with the allergic response. However, they produce another type of antibody the IgG1A and IgG1B (see e.g. Prentø, ATLA, 19, p. 8–14, 1991), which are responsible for their allergenic response to inhaled polypeptides including enzymes. Therefore, when using the Dunkin Hartley animal model, the relative amount of IgG1A and IgG1B is a measure of the allergenicity level.

The Balb/C mice strain is suitable for intratracheal exposure. Balb/C mice produce IgE as the allergic response. More details on assessing respiratory allergens in guinea pigs and mice is described by Kimber et al.,(1996), Fundamental and Applied Toxicology, 33, p. 1–10.

Other animals such as rats, rabbits etc. may also be used for comparable studies.

Composition

The invention relates to a composition comprising a polypeptide-polymer conjugate of the invention.

The composition may be a pharmaceutical or industrial composition.

The composition may further comprise other polypeptides, proteins or enzymes and/or ingredients normally used in e.g. detergents, including soap bars, household articles, agrochemicals, personal care products, including skin care compositions, cleaning compositions for e.g. contact lenses, oral and dermal pharmaceuticals, composition use for treating textiles, compositions used for manufacturing food, e.g. baking, and feed etc.

Use of the Polypeptide-polymer Conjugate

The invention also relates to the use of the method of the invention for reducing the immune response of polypeptides.

It is also an object of the invention to use the polypeptide-polymer conjugate of the invention to reduce the allergenicity of industrial products, such as detergents, such as laundry, dish wash and hard surface cleaning detergents, and food or feed products.

MATERIAL AND METHODS

Materials

Enzymes:

PD498: Protease of subtilisin type shown in WO 93/24623. The sequence of PD498 is shown in SEQ ID NO. 1 and 2. SAVINASE® (Available from Novo Nordisk A/S)

*Humicola lanuginosa* lipase: Available from Novo Nordisk as Lipolase® and is further described in EP 305,216. The DNA and protein sequence is shown in SEQ ID NO 5 and 6, respectively.

Strains:

B. *subtilis* 309 and 147 are variants of *Bacillus lentus*, deposited with the NCIB and accorded the accession numbers NCIB 10309 and 10147, and described in U.S. Pat. No. 3,723,250 incorporated by reference herein.

*E. coli* MC 1000 (M. J. Casadaban and S. N. Cohen (1980); *J. Mol. Biol.* 138 179–207), was made r$^-$, m$^+$ by conventional methods and is also described in U.S. patent application Ser. No. 039,298.

Vectors:

pPD498: *E. coli*—*B. subtilis* shuttle vector (described in U.S. Pat. No. 5,621,089 under section 6.2.1.6) containing the wild-type gene encoding for PD498 protease (SEQ ID NO. 2). The same vector is used for mutagenesis in *E. coli* as well as for expression in *B. subtilis*.

General Molecular Biology Methods:

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990). Enzymes for DNA manipulations were used according to the specifications of the suppliers.

Materials, Chemicals and Solutions:

Horse Radish Peroxidase labeled anti-rat-Ig (Dako, DK, P162, # 031; dilution 1:1000).

Mouse anti-rat IgE (Serotec MCA193; dilution 1:200).

Rat anti-mouse IgE (Serotec MCA419; dilution 1:100).

Biotin-labeled mouse anti-rat IgG1 monoclonal antibody (Zymed 03-9140; dilution 1:1000)

Biotin-labeled rat anti-mouse IgG1 monoclonal antibody (Serotec MCA336B; dilution 1:1000)

Streptavidin-horse radish peroxidase (Kirkegård & Perry 14-30-00; dilution 1:1000).

CovaLink NH$_2$ plates (Nunc, Cat# 459439)

Cyanuric chloride (Aldrich)

Acetone (Merck)

Rat anti-Mouse IgG1, biotin (SeroTec, Cat# MCA336B)

Streptavidin, peroxidase (KPL)

Ortho-Phenylene-diamine (OPD) (Kem-en-Tec)

H$_2$O$_2$, 30% (Merck)

Tween 20 (Merck)

Skim Milk powder (Difco)

H$_2$SO$_4$(Merck)

Buffers and Solutions:

| | | |
|---|---|---|
| Carbonate buffer (0.1 M, pH 10 (1 liter)) | Na$_2$CO$_3$ | 10.60 g |
| PBS (pH 7.2 (1 liter)) | NaCl | 8.00 g |
| | KCl | 0.20 g |
| | K$_2$HPO$_4$ | 1.04 g |
| | KH$_2$PO$_4$ | 0.32 g |

Washing buffer PBS, 0.05% (v/v) Tween 20

Blocking buffer PBS, 2% (wt/v) Skim Milk powder

Dilution buffer PBS, 0.05% (v/v) Tween 20, 0.5% (wt/v) Skim Milk powder

Citrate buffer (0.1M, pH 5.0–5.2 (1 liter))NaCitrate 20.60 g Citric acid 6.30 g

Activation of CovaLink Plates:

Make a fresh stock solution of 10 mg cyanuric chloride per ml acetone.

Just before use, dilute the cyanuric chloride stock solution into PBS, while stirring, to a final concentration of 1 mg/ml.

Add 100 ml of the dilution to each well of the CovaLink NH$_2$ plates, and incubate for 5 minutes at room temperature.

Wash 3 times with PBS.

Dry the freshly prepared activated plates at 50° C. for 30 minutes.

Immediately seal each plate with sealing tape.

Preactivated plates can be stored at room temperature for 3 weeks when kept in a plastic bag.

Sodium Borate, borax (Sigma)

3,3-Dimethyl glutaric acid (Sigma)

CaCl$_2$ (Sigma)

Tresyl chloride (2,2,2-triflouroethansulfonyl chloride) (Fluka)

1-ethyl-3-(3-dimethylaminopropyl)carbodiimide (EDC) (Fluka)

N-Hydroxy succinimide (Fluka art. 56480))

Phosgene (Fluka art. 79380)

Lactose (Merck 7656)

PMSF (phenyl methyl sulfonyl flouride) from Sigma Succinyl-Alanine-Alanine-Proline-Phenylalanine-para-nitroanilide (Suc-AAPF-pNP) Sigma no. S-7388, Mw 624.6 g/mole.

Colouring Substrate:

OPD: o-phenylene-diamine, (Kementec cat no. 4260)

Test Animals:

Dunkin Hartley guinea pigs (from Charles River, Del.)

Female Balb/C mice (about 20 grams) purchased from Bomholdtgaard, Ry, Denmark.

Equipment:

XCEL II (Novex)

ELISA reader (UVmax, Molecular Devices)

HPLC (Waters)

PFLC (Pharmacia)

Superdex-75 column, Mono-Q, Mono S from Pharmacia, SW.

SLT: Fotometer from SLT LabInstruments

Size-exclusion chromatograph (Spherogel TSK-G2000 SW).

Size-exclusion chromatograph (Superdex 200, Pharmacia, SW) Amicon Cell

Enzymes for DNA Manipulations

Unless otherwise mentioned all enzymes for DNA manipulations, such as e.g. restriction endonucleases, ligases etc., are obtained from New England Biolabs. Inc.

Methods

ELISA Procedure for Determination of IqG$_1$ Positive Guinea Pigs

ELISA microtiter plates are coated with rabbit anti-PD498 1:8000 in carbonate buffer and incubated overnight at 4° C. The next day the plates are blocked with 2% BSA for 1 hour and washes 3 times with PBS Tween 20. 1 μg/ml PD498 is added to the plates and incubated for 1 hour, then washed 3 times with PBS Tween 20.

All guinea pig sera samples and controls are applied to the ELISA plates with 2 µl sera and 98 µl PBS, incubated for 1 hour and washed 3 times with PBS Tween 20.

Then goat anti-guinea pig $IgG_1$ (1:4000 in PBS buffer (Nordic Immunology 44–682)) is applied to the plates, incubated for 1 hour and washed with PBS tween 20.

Alkaline phosphatase marked rabbit anti-goat 1:8000 (Sigma A4187) is applied and incubated for 1 hour, washed 2 times in PBS Tween20 and 1 time with diethanol amine buffer.

The marked alkaline phosphatase is developed using p-nitrophenyl phosphate for 30 minutes at 37° C. or until appropriate colour has developed.

The reaction is stopped using Stop medium ($K_2HPO_4$/$HaH_3$ buffer comprising EDTA (pH 10)) and read at OD 405/650 using an ELISA reader.

Double blinds are included on all ELISA plates.

Positive and negative sera values are calculated as the average blind values added 2 times the standard deviation. This gives an accuracy of 95%.

Determination of the Molecule Weight

Electrophoretic separation of proteins was performed by standard methods using 4–20% gradient SDS poly acrylamide gels (Novex). Proteins were detected by silver staining. The molecule weight was measured relative to the mobility of Mark-12® wide range molecule weight standards from Novex.

Protease Activity

Analysis With Suc-Ala-Ala-Pro-Phe-pNa:

Proteases cleave the bond between the peptide and p-nitroaniline to give a visible yellow colour absorbing at 405 nm.

Buffer: e.g. Britton and Robinson buffer pH 8.3 Substrate: 100 mg suc-AAPF-pNa is dissolved into 1 ml dimethyl sulfoxide (DMSO). 100 µl of this is diluted into 10 ml with Britton and Robinson buffer.

The substrate and protease solution is mixed and the absorbance is monitored at 405 nm as a function of time and $ABS_{405}$ nm/min. The temperature should be controlled (20–50° C. depending on protease). This is a measure of the protease activity in the sample.

Proteolytic Activity

In the context of this invention proteolytic activity is expressed in Kilo NOVO Protease Units (KNPU). The activity is determined relatively to an enzyme standard (SAVINASE_), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novo Nordisk A/S, Denmark, which folder is hereby included by reference.

A GU is a Glycine Unit, defined as the proteolytic enzyme activity which, under standard conditions, during a 15-minutes' incubation at 40° C., with N-acetyl casein as substrate, produces an amount of $NH_2$-group equivalent to 1 mmole of glycine.

Enzyme activity can also be measured using the PNA assay, according to reaction with the soluble substrate succinyl-alanine-alanine-proline-phenyl-alanine-para-nitrophenol, which is described in the Journal of American Oil Chemists Society, Rothgeb, T. M., Goodlander, B. D., Garrison, P. H., and Smith, L. A., (1988).

Fermentation of PD498 Variants

Fermentation of PD498 variants in *B. subtilis* are performed at 30° C. on a rotary shaking table (300 r.p.m.) in 500 ml baffled Erlenmeyer flasks containing 100 ml BPX medium for 5 days. In order to make an e.g. 2 liter broth 20 Erlenmeyer flasks are fermented simultaneously.

Media

BPX: Composition (per liter)

| Potato starch | 100 g |
| Ground barley | 50 g |
| Soybean flour | 20 g |
| $Na_2HPO_4 \times 12\ H_2O$ | 9 g |
| Pluronic | 0.1 g |
| Sodium caseinate | 10 g |

The starch in the medium is liquefied with α-amylase and the medium is sterilized by heating at 120° C. for 45 minutes. After sterilization the pH of the medium is adjusted to 9 by addition of $NaHCO_3$ to 0.1 M.

Purification of PD498 Variants

Approximately 1.6 litres of PD498 variant fermentation broth are centrifuged at 5000 rpm for 35 minutes in 1 litre beakers. The supernatants are adjusted to pH 7.0 using 10% acetic acid and filtered on Seitz Supra S100 filter plates. The filtrates are concentrated-to approximately 400 ml using an Amicon CH2A UF unit equipped with an Amicon S1Y10 UF cartridge. The UF concentrate is centrifuged and filtered prior to absorption at room temperature on a Bacitracin affinity column at pH 7. The PD498 variant is eluted from the Bacitracin column at room temperature using 25% 2-propanol and 1 M sodium chloride in a buffer solution with 0.0 dimethylgutaric acid, 0.1 M boric acid and 0.002 M calcium chloride adjusted to pH 7.

The fractions with protease activity from the Bacitracin purification step are combined and applied to a 750 ml Sephadex G25 column (5 cm diameter) equilibrated with a buffer containing 0.01 dimethylglutaric acid, 0.1 M boric acid and 0.002 M calcium chloride adjusted to pH 6.0. Fractions with proteolytic activity from the Sephadex G25 column are combined and applied to a 150 ml CM Sepharose CL 6B cation exchange column (5 cm diameter) equilibrated with a buffer containing 0.01 M dimethylglutaric acid, 0.1 M boric acid, and 0.002 M calcium chloride adjusted to pH 6.0. The protease is eluted using a linear gradient of 0–0.5 M sodium chloride in 1 litres of the same buffer. Protease containing fractions from the CM Sepharose column are combined and filtered through a 2 µfilter.

Balb/C Mice IgG ELISA Procedure:

The antigen is diluted to 1 mg/ml in carbonate buffer.

100 ml is added to each well.

The plates are coated overnight at 4° C.

Unspecific adsorption is blocked by incubating each well for 1 hour at room temperature with 200 ml blocking buffer.

The plates are washed 3× with 300 ml washing buffer.

Unknown mouse sera are diluted in dilution buffer, typically 10×, 20× and 40×, or higher.

100 ml is added to each well.

Incubation is for 1 hour at room temperature.

Unbound material is removed by washing 3× with washing buffer.

The anti-Mouse IgG1 antibody is diluted 2000× in dilution buffer.

100 ml is added to each well.

Incubation is for 1 hour at room temperature.

Unbound material is removed by washing 3× with washing buffer.

Streptavidine is diluted 1000× in dilution buffer.

100 ml is added to each well.

Incubation is for 1 hour at room temperature.

Unbound material is removed by washing 3× with 300 ml washing buffer.

OPD (0.6 mg/ml) and $H_2O_2$ (0.4 ml/ml) is dissolved in citrate buffer.

100 ml is added to each well.

Incubation is for 10 minutes at room temperature.

The reaction is stopped by adding 100 ml $H_2SO_4$.

The plates are read at 492 nm with 620 nm as reference.

Immunisation of Mice

Balb C mice (20 grams) are immunized 10 times (intervals of 14 days) by subcutaneous injection of the modified or unmodified polypeptide in question, respectively by standard, procedures known in art.

EXAMPLES

Example 1

Suitable Substitutions in PD498 for Addition of Amino Attachment Groups (—$NH_2$)

The 3D structure of parent PD498 was modeled as described above based on 59% sequence identity with Thermitase® (2tec.pdb).

The sequence of PD498 is (see SEQ ID NO. 2). PD498 residue numbering is used, 1–280.

The commands performed in Insight (BIOSYM) are shown in the command files makeKzone.bcl and makeKzone2.bcl below:

Conservative Substitutions:
makekzone.bcl

1 Delete Subset *

2 Color Molecule Atoms * Specified Specification 55,0, 255

3 Zone Subset LYS :lys:NZ Static monomer/residue 10 Color_Subset 255,255,0

4 Zone Subset NTERM :1: N Static monomer/residue 10 Color_Subset 255,255,0

5 #NOTE: editnextline ACTSITE residues according to the protein

6 Zone Subset ACTSITE :39,72,226 Static monomer/residue 8 Color_Subset 255,255,0

7 Combine Subset ALLZONE Union LYS NTERM

8 Combine Subset ALLZONE Union ALLZONE ACTSITE

9 #NOTE: editnextline object name according to the protein

10 Combine Subset REST Difference PD498FINALMODEL ALLZONE

11 List Subset REST Atom Output_File restatom.list

12 List Subset REST monomer/residue Output_File restmole.list

13 Color Molecule Atoms ACTSITE Specified Specification 255,0,0

14 List Subset ACTSITE Atom Output_File actsiteatom.list

15 List Subset ACTSITE monomer/residue Output_File actsitemole.list

16 #

17 Zone Subset REST5A REST Static Monomer/Residue 5-Color_Subset

18 Combine Subset SUB5A Difference REST5A ACTSITE

19 Combine Subset SUB5B Difference SUB5A REST

20 Color Molecule Atoms SUB5B Specified Specification 255,255,255

21 List Subset SUB5B Atom Output_File sub5batom.list

22 List Subset SUB5B monomer/residue Output_File sub5bmole.list

23 #Now identify sites for lys→arg substitutions and continue with makezone2.bcl 24 #Use grep command to identify ARG in restatom.list, sub5batom.list & accsiteatom.list Comments:

Lines 1–8: The subset ALLZONE is defined as those residues which are either within 10 Å of the free amino groups on lysines or the N-terminal, or within 8 Å of the catalytic triad residues 39, 72 and 226.

Line 10: The subset REST is defined as those residues not included in ALLZONE.

Lines 17–20: Subset SUB5B is defined as those residues in a 5 Å shell around REST, excluding residues within 8 Å of the catalytic residues.

Line 23–24: REST contains Arg62 and Arg169, SUB5B contains Arg51, Arg121, and Arg250. ACTSITE contains Arg103, but position 103 is within 8 Å from essential_ catalytic residues, and thus not relevant.

The colour codes are: (255,0,255)=magenta, (255,255,0) yellow, (255,0,0) red, and (255, 255, 255)=white.

The substitutions R51K, R62K, R121K, R169K and R250K are identified in parent PD498 as suitable sites for mutagenesis. The residues are substituted below in section 2, and further analysis done:

Non-conservative Substitutions:
makeKzone2.bcl

1 #sourcefile makezone2.bcl Claus von der Osten 961128

2 #

3 #having scanned lists (grep arg command) and identified sites for lys→arg substitutions 4 #NOTE: editnextline object name according to protein 5 Copy Object -To_Clipboard -Displace PD498FINALMODEL newmodel 6 Biopolymer 7 #NOTE: editnextline object name according to protein 8 Blank Object On PD498FINALMODEL 9 #NOTE: editnextlines with lys→arg positions 10 Replace Residue newmodel:51 lys L 11 Replace Residue newmodel:62 lys L 12 Replace Residue newmodel:121 lys L 13 Replace Residue newmodel:169 lys L 14 Replace Residue newmodel:250 lys L

15 #

16 #Now repeat analysis done prior to arg→lys, now including introduced lysines

17 Color Molecule Atoms newmodel Specified Specification 255,0,255

18 Zone Subset LYSx newmodel:lys:NZ Static monomer/residue 10 Color_Subset 255,255,0

19 Zone Subset NTERMx newmodel:1:N Static monomer/residue 10 Color_Subset 255,255,0

20 #NOTE: editnextline ACTSITEx residues according to the protein

21 Zone Subset ACTSITEx newmodel:39,72,226 Static monomer/residue 8 Color_Subset 255,255,0

22 Combine Subset ALLZONEx Union LYSx NTERMx

23 Combine Subset ALLZONEx Union ALLZONEx ACTSITEx

24 Combine Subset RESTx Difference newmodel ALLZONEx
25 List Subset RESTx Atom Output_File restatom.list
26 List Subset RESTx monomer/residue Output_File restxmole.list
27 #
28 Color Molecule Atoms ACTSITEx Specified Specification 255,0,0
29 List Subset ACTSITEx Atom Output_File actsitexatom.list
30 List Subset ACTSITEx monomer/residue Output_File actsitexmole.list
31 #
32 #read restxatom.list or restxmole.list to identify sites for (not_arg)→lys subst. if needed Comments:

Lines 1–15: Solvent exposed arginines in subsets REST and SUB5B are replaced by lysines. Solvent accessibilities are recalculated following arginine replacement.

Lines 16–23: The subset ALLZONEx is defined as those residues which are either within 10 Å of the free amino groups on Lysines (after replacement) or the N-terminal, or within 8 Å of the catalytic triad residues 39, 72 and 226.

Line 24–26: The subset RESTx is defined as those residues not included in ALLZONEx, i.e. residues which are still potential epitope contributors. of the residues in RESTx, the following are >5% exposed (see lists below): 6–7,9–12, 43–45,65,87–88,209,211,216–221,262.

The following mutations are proposed in parent PD498: P6K, Y7K, S9K, A10K, Y11K, Q12K, D43K, Y44K, N45K, N65K, G87K, I88K, N209K, A211K, N216K, N217K, G218K, Y219K, S220K, Y221K, G262K. Relevant data for Example 1: Solvent accessibility data for PD498MODEL:

| # PD498MODEL Fri Nov 29 10:24 MET 1996 | |
|---|---|
| # residue | area |
| TRP_1 | 136.275711 |
| SER_2 | 88.188095 |
| PRO_3 | 15.458788 |
| ASN_4 | 95.322319 |
| ASP_5 | 4.903404 |
| PRO_6 | 68.096909 |
| TYR_7 | 93.333252 |
| TYR_8 | 31.791576 |
| SER_9 | 95.983139 |
| ALA_10 | 77.983536 |
| TYR_11 | 150.704727 |
| GLN_12 | 26.983349 |
| TYR_13 | 44.328232 |
| GLY_14 | 3.200084 |
| PRO_15 | 2.149547 |
| GLN_16 | 61.385445 |
| ASN_17 | 37.776707 |
| THR_18 | 1.237873 |
| SER_19 | 41.031750 |
| THR_20 | 4.321402 |
| PRO_21 | 16.658991 |
| ALA_22 | 42.107288 |
| ALA_23 | 0.000000 |
| TRP_24 | 3.713619 |
| ASP_25 | 82.645493 |
| VAL_26 | 74.397812 |
| THR_27 | 14.950654 |
| ARG_28 | 110.606209 |
| GLY_29 | 0.242063 |
| SER_30 | 57.225292 |
| SER_31 | 86.986198 |

-continued

| # PD498MODEL Fri Nov 29 10:24 MET 1996 | |
|---|---|
| # residue | area |
| THR_32 | 1.928865 |
| GLN_33 | 42.008949 |
| THR_34 | 0.502189 |
| VAL_35 | 0.268693 |
| ALA_36 | 0.000000 |
| VAL_37 | 5.255383 |
| LEU_38 | 1.550332 |
| ASP_39 | 3.585718 |
| SER_40 | 2.475746 |
| GLY_41 | 4.329043 |
| VAL_42 | 1.704864 |
| ASP_43 | 25.889742 |
| TYR_44 | 89.194855 |
| ASN_45 | 109.981819 |
| HIS_46 | 0.268693 |
| PRO_47 | 66.580925 |
| ASP_48 | 0.000000 |
| LEU_49 | 0.770882 |
| ALA_50 | 49.618046 |
| ARG_51 | 218.751709 |
| LYS_52 | 18.808538 |
| VAL_53 | 39.937984 |
| ILE_54 | 98.478104 |
| LYS_55 | 103.612228 |
| GLY_56 | 17.199390 |
| TYR_57 | 67.719147 |
| ASP_58 | 0.000000 |
| PHE_59 | 40.291119 |
| ILE_60 | 50.151962 |
| ASP_61 | 70.078888 |
| ARG_62 | 166.777557 |
| ASP_63 | 35.892376 |
| ASN_64 | 120.641953 |
| ASN_65 | 64.982895 |
| PRO_66 | 6.986028 |
| MET_67 | 58.504269 |
| ASP_68 | 28.668840 |
| LEU_69 | 104.467468 |
| ASN_70 | 78.460953 |
| GLY_71 | 5.615932 |
| HIS_72 | 43.158905 |
| GLY_73 | 0.268693 |
| THR_74 | 0.000000 |
| HIS_75 | 0.484127 |
| VAL_76 | 1.880854 |
| ALA_77 | 0.000000 |
| GLY_78 | 0.933982 |
| THR_79 | 9.589676 |
| VAL_80 | 0.000000 |
| ALA_81 | 0.000000 |
| ALA_82 | 0.000000 |
| ASP_83 | 46.244987 |
| THR_84 | 27.783333 |
| ASN_85 | 75.924225 |
| ASN_86 | 44.813908 |
| GLY_87 | 50.453152 |
| ILE_88 | 74.428070 |
| GLY_89 | 4.115077 |
| VAL_90 | 6.717335 |
| ALA_91 | 2.872341 |
| GLY_92 | 0.233495 |
| MET_93 | 5.876057 |
| ALA_94 | 0.000000 |
| PRO_95 | 17.682203 |
| ASP_96 | 83.431740 |
| THR_97 | 1.506567 |
| LYS_98 | 72.674973 |
| ILE_99 | 4.251006 |
| LEU_100 | 6.717335 |
| ALA_101 | 0.806080 |
| VAL_102 | 1.426676 |
| ARG_103 | 2.662697 |
| VAL_104 | 2.171855 |
| LEU_105 | 18.808538 |
| ASP_106 | 52.167435 |

-continued

PD498MODEL    Fri Nov 29 10:24 MET 1996

| # residue | area |
|---|---|
| ALA_107 | 52.905663 |
| ASN_108 | 115.871315 |
| GLY_109 | 30.943356 |
| SER_110 | 57.933651 |
| GLY_111 | 50.705326 |
| SER_112 | 56.383320 |
| LEU_113 | 71.312195 |
| ASP_114 | 110.410919 |
| SER_115 | 13.910152 |
| ILE_116 | 22.570246 |
| ALA_117 | 5.642561 |
| SER_118 | 29.313131 |
| GLY_119 | 0.000000 |
| ILE_120 | 1.343467 |
| ARG_121 | 118.391129 |
| TYR_122 | 44.203033 |
| ALA_123 | 0.000000 |
| ALA_124 | 7.974043 |
| ASP_125 | 83.851639 |
| GLN_126 | 64.311974 |
| GLY_127 | 36.812618 |
| ALA_128 | 4.705107 |
| LYS_129 | 90.886139 |
| VAL_130 | 1.039576 |
| LEU_131 | 2.149547 |
| ASN_132 | 4.315227 |
| LEU_133 | 1.880854 |
| SER_134 | 3.563334 |
| LEU_135 | 26.371397 |
| GLY_136 | 59.151070 |
| CYS_137 | 63.333755 |
| GLU_138 | 111.553314 |
| CYS_139 | 83.591461 |
| ASN_140 | 80.757843 |
| SER_141 | 25.899158 |
| THR_142 | 99.889725 |
| THR_143 | 73.323814 |
| LEU_144 | 5.589301 |
| LYS_145 | 94.708755 |
| SER_146 | 72.636993 |
| ALA_147 | 9.235920 |
| VAL_148 | 1.612160 |
| ASP_149 | 57.431465 |
| TYR_150 | 106.352493 |
| ALA_151 | 0.268693 |
| TRP_152 | 43.133667 |
| ASN_153 | 112.864975 |
| LYS_154 | 110.009468 |
| GLY_155 | 33.352180 |
| ALA_156 | 3.493014 |
| VAL_157 | 1.048144 |
| VAL_158 | 2.043953 |
| VAL_159 | 0.000000 |
| ALA_160 | 0.537387 |
| ALA_161 | 10.872165 |
| ALA_162 | 7.823834 |
| GLY_163 | 12.064573 |
| ASN_164 | 81.183388 |
| ASP_165 | 64.495300 |
| ASN_166 | 83.457443 |
| VAL_167 | 68.516815 |
| SER_168 | 78.799652 |
| ARG_169 | 116.937134 |
| THR_170 | 57.275074 |
| PHE_171 | 51.416462 |
| GLN_172 | 18.934589 |
| PRO_173 | 1.880854 |
| ALA_174 | 6.522357 |
| SER_175 | 26.184139 |
| TYR_176 | 21.425076 |
| PRO_177 | 85.613541 |
| ASN_178 | 34.700817 |
| ALA_179 | 0.268693 |
| ILE_180 | 1.074774 |
| ALA_181 | 3.761708 |

-continued

PD498MODEL    Fri Nov 29 10:24 MET 1996

| # residue | area |
|---|---|
| VAL_182 | 0.000000 |
| GLY_183 | 2.149547 |
| ALA_184 | 0.951118 |
| ILE_185 | 0.806080 |
| ASP_186 | 30.022263 |
| SER_187 | 72.518509 |
| ASN_188 | 117.128021 |
| ASP_189 | 47.601345 |
| ARG_190 | 150.050873 |
| LYS_191 | 64.822807 |
| ALA_192 | 2.686934 |
| SER_193 | 96.223808 |
| PHE_194 | 51.482613 |
| SER_195 | 1.400973 |
| ASN_196 | 4.148808 |
| TYR_197 | 80.937309 |
| GLY_198 | 10.747736 |
| THR_199 | 93.221252 |
| TRP_200 | 169.943604 |
| VAL_201 | 15.280325 |
| ASP_202 | 12.141763 |
| VAL_203 | 0.268693 |
| THR_204 | 3.409728 |
| ALA_205 | 0.000000 |
| PRO_206 | 0.000000 |
| GLY_207 | 0.000000 |
| VAL_208 | 37.137192 |
| ASN_209 | 78.286270 |
| ILE_210 | 9.404268 |
| ALA_211 | 25.938599 |
| SER_212 | 5.037172 |
| THR_213 | 0.000000 |
| VAL_214 | 22.301552 |
| PRO_215 | 45.251030 |
| ASN_216 | 131.014160 |
| ASN_217 | 88.383461 |
| GLY_218 | 21.226780 |
| TYR_219 | 88.907570 |
| SER_220 | 39.966541 |
| TYR_221 | 166.037018 |
| MET_222 | 50.951096 |
| SER_223 | 54.435001 |
| GLY_224 | 1.880854 |
| THR_225 | 1.634468 |
| SER_226 | 17.432346 |
| MET_227 | 7.233279 |
| ALA_228 | 0.000000 |
| SER_229 | 0.000000 |
| PRO_230 | 0.268693 |
| HIS_231 | 2.680759 |
| VAL_232 | 0.000000 |
| ALA_233 | 0.000000 |
| GLY_234 | 1.074774 |
| LEU_235 | 11.500556 |
| ALA_236 | 0.000000 |
| ALA_237 | 0.000000 |
| LEU_238 | 1.612160 |
| LEU_239 | 0.000000 |
| ALA_240 | 10.648088 |
| SER_241 | 39.138004 |
| GLN_242 | 71.056175 |
| GLY_243 | 66.487144 |
| LYS_244 | 43.256012 |
| ASN_245 | 80.728127 |
| ASN_246 | 34.859673 |
| VAL_247 | 84.145645 |
| GLN_248 | 51.819775 |
| ILE_249 | 8.598188 |
| ARG_250 | 35.055809 |
| GLN_251 | 71.928093 |
| ALA_252 | 0.000000 |
| ILE_253 | 4.845899 |
| GLU_254 | 13.344438 |
| GLN_255 | 81.705254 |
| THR_256 | 9.836061 |

-continued

| # PD498MODEL | Fri Nov 29 10:24 MET 1996 |
|---|---|
| # residue | area |
| ALA_257 | 2.810513 |
| ASP_258 | 44.656136 |
| LYS_259 | 113.071686 |
| ILE_260 | 32.089527 |
| SER_261 | 91.590103 |
| GLY_262 | 26.450439 |
| THR_263 | 38.308762 |
| GLY_264 | 46.870056 |
| THR_265 | 88.551804 |
| ASN_266 | 34.698349 |
| PHE_267 | 7.756911 |
| LYS_268 | 103.212852 |
| TYR_269 | 37.638382 |
| GLY_270 | 0.000000 |
| LYS_271 | 11.376978 |
| ILE_272 | 2.885231 |
| ASN_273 | 19.195255 |
| SER_274 | 2.651736 |
| ASN_275 | 38.177547 |
| LYS_276 | 84.549576 |
| ALA_277 | 1.074774 |
| VAL_278 | 4.775503 |
| ARG_279 | 162.693054 |
| TYR_280 | 96.572929 |
| CA_281 | 0.000000 |
| CA_282 | 0.000000 |
| CA_283 | 8.803203 |

Subset REST:
  restmole.list
Subset REST:
  PD498FINALMODEL:6–7,9–12,43–46,61–63,65, 87–89,111–114,117–118,131,
  PD498FINALMODEL:137–139,158–159,169–171, 173–174,180–181,209,211,
  PD498FINALMODEL:216–221,232–233,262, E282H
  restatom.list
Subset REST:
  PD498FINALMODEL:PRO 6:N,CA,CD,C,O,CB,CG
  PD498FINALMODEL:TYR 7:N,CA,C,O,CB,CG,CD1, CD2,CE1,CE2,CZ,OH
  PD498FINALMODEL:SER 9:N,CA,C,O,CB,OG
  PD498FINALMODEL:ALA 10:N,CA,C,O,CB
  PD498FINALMODEL:TYR 11:N,CA,C,O,CB,CG,CD1, CD2,CE1,CE2,CZ,OH
  PD498FINALMODEL:GLN 12:N,CA,C,O,CB,CG,CD, OE1,NE2
  PD498FINALMODEL:ASP 43:N,CA,C,O,CB,CG,OD1, OD2
  PD498FINALMODEL:TYR 44:N,CA,C,O,CB,CG,CD1,CD2,CE1,CE2,CZ,OH
  PD498FINALMODEL:ASN 45:N,CA,C,O,CB,CG,OD1, ND2
  PD498FINALMODEL:HIS 46:N,CA,C,O,CB,CG,ND1,CD2,CE1,NE2
  PD498FINALMODEL:ASP 61:N,CA,C,O,CB,CG,OD1, OD2
  PD498FINALMODEL:ARG 62:N,CA,C,O,CB,CG,CD,NE,CZ,NH1,NH2
  PD498FINALMODEL:ASP 63:N,CA,C,O,CB,CG,OD1, OD2
  PD498FINALMODEL:ASN 65:N,CA,C,O,CB,CG,OD1, ND2
  PD498FINALMODEL:GLY 87:N,CA,C,O
  PD498FINALMODEL:ILE 88:N,CA,C,O,CB,CG1,CG2, CD1
  PD498FINALMODEL:GLY 89:N,CA,C,O
  PD498FINALMODEL:GLY 111:N,CA,C,O
  PD498FINALMODEL:SER 112:N,CA,C,O,CB,OG
  PD498FINALMODEL:LEU 113:N,CA,C,O,CB,CG, CD1,CD2
  PD498FINALMODEL:ASP 114:N,CA,C,O,CB,CG, OD1,OD2
  PD498FINALMODEL:ALA 117:N,CA,C,O,CB
  PD498FINALMODEL:SER 118:N,CA,C,O,CB,OG
  PD498FINALMODEL:LEU 131:N,CA,C,O,CB,CG, CD1,CD2
  PD498FINALMODEL:CYS 137:N,CA,C,O,CB,SG
  PD498FINALMODEL:GLU 138:N,CA,C,O,CB,CG,CD,OE1,OE2
  PD498FINALMODEL:CYS 139:N,CA,C,O,CB,SG
  PD498FINALMODEL:VAL 158:N,CA,C,O,CB,CG1, CG2
  PD498FINALMODEL:VAL 159:N,CA,C,O,CB,CG1, CG2
  PD498FINALMODEL:ARG 169:N,CA,C,O,CB,CG,CD,NE,CZ,NH1,NH2
  PD498FINALMODEL:THR 170:N,CA,C,O,CB,OG1, CG2
  PD498FINALMODEL:PHE 171:N,CA,C,O,CB,CG,CD1,CD2,CE1,CE2,CZ
  PD498FINALMODEL:PRO 173:N,CA,CD,C,O,CB,CG
  PD498FINALMODEL:ALA 174:N,CA,C,O,CB
  PD498FINALMODEL:ILE 180:N,CA,C,O,CB,CG1, CG2,CD1
  PD498FINALMODEL:ALA 181:N,CA,C,O,CB
  PD498FINALMODEL:ASN 209:N,CA,C,O,CB,CG, OD1,ND2
  PD498FINALMODEL:ALA 211:N,CA,C,O,CB
  PD498FINALMODEL:ASN 216:N,CA,C,O,CB,CG, OD1,ND2
  PD498FINALMODEL:ASN 217:N,CA,C,O,CB,CG, OD1,ND2
  PD498FINALMODEL:GLY 218:N,CA,C,O
  PD498FINALMODEL:TYR 219:N,CA,C,O,CB,CG,CD1,CD2,CE1,CE2,CZ,OH
  PD498FINALMODEL:SER 220:N,CA,C,O,CB,OG
  PD498FINALMODEL:TYR 221:N,CA,C,O,CB,CG,CD1,CD2,CE1,CE2,CZ,OH
  PD498FINALMODEL:VAL 232:N,CA,C,O,CB,CG1, CG2
  PD498FINALMODEL:ALA 233:N,CA,C,O,CB
  PD498FINALMODEL:GLY 262:N,CA,C,O
  PD498FINALMODEL:CA E282H:CA
Subset SUB5B:
  sub5bmole.list
Subset SUB5B:
  PD498FINALMODEL:4–5,8,13–16,34–35,47–51,53,64, 83,85–86,90–91,120–124,
  PD498FINALMODEL:128–130,140–141,143–144, 147–148,151–152,156–157,
  PD498FINALMODEL:165,167–168,172,175–176, 178–179,196,200–205,208, PD498FINALMODEL:234–237,250,253–254,260–261, 263–267,272,E281H,
PD498FINALMODEL:E283H
sub5batom.list
Subset SUB5B:
PD498FINALMODEL:ASN.4:N,CA,C,O,CB,CG,OD1, ND2
PD498FINALMODEL:ASP 5:N,CA,C,O,CB,CG,OD1, OD2
PD498FINALMODEL:TYR 8:N,CA,C,O,CB,CG,CD1,CD2,CE1,CE2,CZ,OH
PD498FINALMODEL:TYR 13:N,CA,C,O,CB,CG,CD1,CD2,CE1,CE2,CZ,OH
PD498FINALMODEL:GLY 14:N,CA,C,O
PD498FINALMODEL:PRO 15:N,CA,CD,C,O, CB,CG
PD498FINALMODEL:GLN 16:N,CA,C,O,CB,CG,CD, OE1,NE2
PD498FINALMODEL:THR 34:N,CA,C,O,CB,OG1, CG2
PD498FINALMODEL:VAL 35:N,CA,C,O,CB,CG1, CG2
PD498FINALMODEL:PRO 47:N,CA,CD,C,O,CB,CG
PD498FINALMODEL:ASP 48:N,CA,C,O,CB,CG,OD1, OD2
PD498FINALMODEL:LEU 49:N,CA,C,O,CB,CG,CD1, CD2
PD498FINALMODEL:ALA 50:N,CA,C,O,CB
PD498FINALMODEL:ARG 51:N,CA,C,O,CB,CG,CD,NE,CZ,NH1,NH2
PD498FINALMODEL:VAL 53:N,CA,C,O,CB,CG1, CG2
PD498FINALMODEL:ASN 64:N,CA,C,O,CB,CG,OD1, ND2
PD498FINALMODEL:ASP 83:N,CA,C,O,CB,CG,OD1, OD2
PD498FINALMODEL:ASN 85:N,CA,C,O,CB,CG,OD1, ND2
PD498FINALMODEL:ASN 86:N,CA,C,O,CB,CG,OD1, ND2
PD498FINALMODEL:VAL 90:N,CA, C,O,CB,CG1, CG2
PD498FINALMODEL:ALA 91:N,CA,C,O,CB
PD498FINALMODEL:ILE 120:N,CA,C,O,CB,CG1, CG2,CD1
PD498FINALMODEL:ARG 121:N,CA,C,O,CB,CG,CD,NE,CZ,NH1,NH2
PD498FINALMODEL:TYR 122:N,CA,C,O,CB,CG,CD1,CD2,CE1,CE2,CZ,OH
PD498FINALMODEL:ALA 123:N,CA,C,O,CB
PD498FINALMODEL:ALA 124:N,CA,C,O,CB
PD498FINALMODEL:ALA 128:N,CA,C,O,CB
PD498FINALMODEL:LYS 129:N,CA,C,O,CB,CG,CD, CE,NZ
PD498FINALMODEL:VAL 130:N,CA,C,O,CB,CG1, CG2
PD498FINALMODEL:ASN 140:N,CA,C,O,CB,CG, OD1,ND2
PD498FINALMODEL:SER 141:N,CA,C,O,CB,OG
PD498FINALMODEL:THR 143:N,CA,C,O,CB,OG1, CG2
PD498FINALMODEL:LEU 144:N,CA,C,O,CB,CG, CD1,CD2
PD498FINALMODEL:ALA 147:N,CA,C,O,CB
PD498FINALMODEL:VAL 148:N,CA,C,O,CB,CG1, CG2
PD498FINALMODEL:ALA 151:N,CA,C,O,CB
PD498FINALMODEL:TRP 52:N,CA,C,O,CB,CG,CD1,CD2,NE1,CE2,CE3, CZ2, CZ3,CH2
PD498FINALMODEL:ALA 156:N,CA,C,O,CB
PD498FINALMODEL:VAL 157:N,CA,C,O,CB,CG1, CG2
PD498FINALMODEL:ASP 165:N,CA,C,O,CB,CG, OD1,OD2
PD498FINALMODEL:VAL 167:N,CA,C,O,CB,CG1, CG2
PD498FINALMODEL:SER 168:N,CA,C,O,CB,OG
PD498FINALMODEL:GLN 172:N,CA,C,O,CB,CG,CD,OE1,NE2
PD498FINALMODEL:SER 175:N,CA,C,O,CB,OG
PD498FINALMODEL:TYR 176:N,CA,C,O,CB,CG,CD1,CD2,CE1,CE2,CZ,OH
PD498FINALMODEL:ASN 178:N,CA,C,O,CB,CG, OD1,ND2
PD498FINALMODEL:ALA 179:N,CA,C,O,CB
PD498FINALMODEL:ASN 196:N,CA,C,O,CB,CG, OD1,ND2
PD498FINALMODEL:TRP 200:N,CA,C,O,CB,CG,CD1,CD2,NE1,CE2,CE3, CZ2,CZ3,CH2
PD498FINALMODEL:VAL 201:N,CA,C,O,CB,CG1, CG2
PD498FINALMODEL:ASP 202:N,CA,C,O,CB,CG, OD1,OD2
PD498FINALMODEL:VAL 203:N,CA,C,O,CB,CG1, CG2
PD498FINALMODEL:THR 204:N,CA,C,O,CB,OG1, CG2
PD498FINALMODEL:ALA 205:N,CA,C,O,CB
PD498FINALMODEL:VAL 208:N,CA,C,O,CB,CG1, CG2
PD498FINALMODEL:GLY 234:N,CA,C,O
PD498FINALMODEL:LEU 235:N,CA,C,O,CB,CG, CD1,CD2
PD498FINALMODEL:ALA 236:N,CA,C,O,CB
PD498FINALMODEL:ALA 237:N,CA,C,O,CB
PD498FINALMODEL:ARG 250:N,CA,C,O,CB,CG,CD,NE,CZ,NH1,NH2
PD498FINALMODEL:ILE 253:N,CA,C,O,CB,CG1, CG2,CD1
PD498FINALMODEL:GLU 254:N,CA,C,O,CB,CG,CD,OE1,OE2
PD498FINALMODEL:ILE 260:N,CA,C,O,CB,CG1, CG2,CD1
PD498FINALMODEL:SER 261:N,CA,C,O,CB,OG
PD498FINALMODEL:THR 263:N,CA,C,O,CB,OG1, CG2
PD498FINALMODEL:GLY 264:N,CA,C,O
PD498FINALMODEL:THR 265:N,CA,C,O,CB,OG1, CG2
PD498FINALMODEL:ASN 266:N,CA,C,O,CB,CG, OD1,ND2

PD498FINALMODEL:PHE
  267:N,CA,C,O,CB,CG,CD1,CD2,CE1,CE2,CZ
PD498FINALMODEL:ILE 272:N,CA,C,O,CB,CG1,
  CG2,CD1
PD498FINALMODEL:CA E281H:CA
PD498FINALMODEL:CA E283H:NA
Subset ACTSITE:
  actsitemole.list
Subset ACTSITE:
  PD498FINALMODEL:36–42,57–60,66–80,100–110,
   115–116,119,132–136,160–164,
  PD498FINALMODEL:182–184,194,206–207,210,
   212–215,222–231
  actsiteatom.list
Subset ACTSITE:
  PD498FINALMODEL:ALA 36:N,CA,C,O,CB
  PD498FINALMODEL:VAL 37:N,CA,C,O,CB,CG1,
   CG2
  PD498FINALMODEL:LEU 38:N,CA,C,O,CB,CG,CD1,
   CD2
  PD498FINALMODEL:ASP 39:N,CA,C,O,CB,CG,OD1,
   OD2
  PD498FINALMODEL:SER 40:N,CA,C,O,CB,OG
  PD498FINALMODEL:GLY 41:N,CA,C,O
  PD498FINALMODEL:VAL 42:N,CA,C,O,CB,CG1,
   CG2
  PD498FINALMODEL:TYR
   57:N,CA,C,O,CB,CG,CD1,CD2,CE1,CE2,CZ,OH
  PD498FINALMODEL:ASP 58:N,CA,C,O,CB,CG,OD1,
   OD2
  PD498FINALMODEL:PHE
   59:N,CA,C,O,CB,CG,CD1,CD2,CE1,CE2,CZ
  PD498FINALMODEL:ILE 60:N,CA,C,O,CB,CG1,CG2,
   CD1
  PD498FINALMODEL:PRO 66:N,CA,CD,C,O,CB,CG
  PD498FINALMODEL:MET 67:N,CA,C,O,CB,CG,SD,
   CE
  PD498FINALMODEL:ASP 68:N,CA,C,O,CB,CG,OD1,
   OD2
  PD498FINALMODEL:LEU 69:N,CA,C,O,CB,CG,CD1,
   CD2
  PD498FINALMODEL:ASN 70:N,CA,C,O,CB,CG,OD1,
   ND2
  PD498FINALMODEL:GLY 71:N,CA,C,O
  PD498FINALMODEL:HIS
   72:N,CA,C,O,CB,CG,ND1,CD2,CE1,NE2
  PD498FINALMODEL:GLY 73:N,CA,C,O
  PD498FINALMODEL:THR 74:N,CA,C,O,CB,OG1,
   CG2
  PD498FINALMODEL:HIS
   75:N,CA,C,O,CB,CG,ND1,CD2,CE1,NE2
  PD498FINALMODEL:VAL 76:N,CA,C,O,CB,CG1,
   CG2
  PD498FINALMODEL:ALA 77:N,CA,C,O,CB
  PD498FINALMODEL:GLY 78:N,CA,C,O
  PD498FINALMODEL:THR 79:N,CA,C,O,CB,OG1,
   CG2
  PD498FINALMODEL:VAL 80:N,CA,C,O,CB,CG1,
   CG2
  PD498FINALMODEL:LEU 100:N,CA,C,O,CB,CG,
   CD1,CD2
  PD498FINALMODEL:ALA 101:N,CA,C,O,CB
  PD498FINALMODEL:VAL 102:N,CA,C,O,CB,CG1,
   CG2
  PD498FINALMODEL:ARG
   103:N,CA,C,O,CB,CG,CD,NE,CZ,NH1,NH2
  PD498FINALMODEL:VAL 104:N,CA,C,O,CB,CG1,
   CG2
  PD498FINALMODEL:LEU 105:N,CA,C,O,CB,CG,
   CD1,CD2
  PD498FINALMODEL:ASP 106:N,CA,C,O,CB,CG,
   OD1,OD2
  PD498FINALMODEL:ALA 107:N,CA,C,O,CB
  PD498FINALMODEL:ASN 108:N,CA,C,O,CB,CG,
   OD1,ND2
  PD498FINALMODEL:GLY 109:N,CA,C,O
  PD498FINALMODEL:SER 110:N,CA,C,O,CB,OG
  PD498FINALMODEL:SER 115:N,CA,C,O,CB,OG
  PD498FINALMODEL:ILE 116:N,CA,C,O,CB,CG1,
   CG2,CD1
  PD498FINALMODEL:GLY 119:N,CA,C,O
  PD498FINALMODEL:ASN 132:N,CA,C,O,CB,CG,
   OD1,ND2
  PD498FINALMODEL:LEU 133:N,CA,C,O,CB,CG,
   CD1,CD2
  PD498FINALMODEL:SER 134:N,CA,C,O,CB,OG
  PD498FINALMODEL:LEU 135:N,CA,C,O,CB,CG,
   CD1,CD2
  PD498FINALMODEL:GLY 136:N,CA,C,O
  PD498FINALMODEL:ALA 160:N,CA,C,O,CB
  PD498FINALMODEL:ALA 161:N,CA,C,O,CB
  PD498FINALMODEL:ALA 162:N,CA,C,O,CB
  PD498FINALMODEL:GLY 163:N,CA,C,O
  PD498FINALMODEL:ASN 164:N,CA,C,O,CB,CG,
   OD1,ND2
  PD498FINALMODEL:VAL 182:N,CA,C,O,CB,CG1,
   CG2
  PD498FINALMODEL:GLY 183:N,CA,C,O
  PD498FINALMODEL:ALA 184:N,CA,C,O,CB
  PD498FINALMODEL:PHE
   194:N,CA,C,O,CB,CG,CD1,CD2,CE1,CE2,CZ
  PD498FINALMODEL:PRO 206:N,CA,CD,C,O,CB,CG
  PD498FINALMODEL:GLY 207:N,CA,C,O
  PD498FINALMODEL:ILE 210:N,CA,C,O,CB,CG1,
   CG2,CD1
  PD498FINALMODEL:SER 212:N,CA,C,O,CB,OG
  PD498FINALMODEL:THR 213:N,CA,C,O,CB,OG1,
   CG2
  PD498FINALMODEL:VAL 214:N,CA,C,O,CB,CG1,
   CG2
  PD498FINALMODEL:PRO 215:N,CA,CD,C,O,CB,CG
  PD498FINALMODEL:MET 222:N,CA,C,O,CB,CG,SD,
   CE
  PD498FINALMODEL:SER 223:N,CA,C,O,CB,OG
  PD498FINALMODEL:GLY 224:N,CA,C,O
  PD498FINALMODEL:THR 225:N,CA,C,O,CB,OG1,
   CG2
  PD498FINALMODEL:SER 226:N,CA,C,O,CB,OG
  PD498FINALMODEL:MET 227:N,CA,C,O,CB,CG,SD,
   CE
  PD498FINALMODEL:ALA 228:N,CA,C,O,CB PD498FINALMODEL:SER 229:N,CA,C,O,CB,OG
PD498FINALMODEL:PRO 230:N,CA,CD,C,O,CB,CG
PD498FINALMODEL:HIS 231:N,CA,C,O,CB,CG,ND1,CD2,CE1,NE2
Subset RESTx:
 restxmole.list
Subset RESTx:
 NEWMODEL:6–7,9–12,43–46,65,87–89,131,173,209, 211,216–221,232–233,
 NEWMODEL:262,E282H
 restxatom.list
Subset RESTx:
 NEWMODEL:PRO 6:N,CA,CD,C,O,CB,CG
 NEWMODEL:TYR 7:N,CA,C,O,CB,CG,CD1,CD2, CE1,CE2,CZ,OH
 NEWMODEL:SER 9:N,CA,C,O,CB,OG
 NEWMODEL:ALA 10:N,CA,C,O,CB
 NEWMODEL:TYR 11:N,CA,C,O,CB,CG,CD1,CD2, CE1,CE2,CZ,OH
 NEWMODEL:GLN 12:N,CA,C,O,CB,CG,CD,OE1,NE2
 NEWMODEL:ASP 43:N,CA,C,O,CB,CG,OD1,OD2
 NEWMODEL:TYR 44:N,CA,C,O,CB,CG,CD1,CD2, CE1,CE2,CZ,OH
 NEWMODEL:ASN 45:N,CA,C,O,CB,CG,OD1,ND2
 NEWMODEL:HIS 46:N,CA,C,O,CB,CG,ND1,CD2, CE1,NE2
 NEWMODEL:ASN 65:N,CA,C,O,CB,CG,OD1,ND2
 NEWMODEL:GLY 87:N,CA,C,O
 NEWMODEL:ILE 88:N,CA,C,O,CB,CG1,CG2,CD1
 NEWMODEL:GLY 89:N,CA,C,O
 NEWMODEL:LEU 131:N,CA,C,O,CB,CG,CD1,CD2
 NEWMODEL:PRO 173:N,CA,CD,C,O,CB,CG
 NEWMODEL:ASN 209:N,CA,C,O,CB,CG,OD1,ND2
 NEWMODEL:ALA 211:N,CA,C,O,CB
 NEWMODEL:ASN 216:N,CA,C,O,CB,CG,OD1,ND2
 NEWMODEL:ASN 217:N,CA,C,O,CB,CG,OD1,ND2
 NEWMODEL:GLY 218:N,CA,C,O
 NEWMODEL:TYR 219:N,CA,C,O,CB,CG,CD1,CD2, CE1,CE2,CZ,OH
 NEWMODEL:SER 220:N,CA,C,O,CB,OG
 NEWMODEL:TYR 221:N,CA,C,O,CB,CG,CD1,CD2, CE1,CE2,CZ,OH
 NEWMODEL:VAL 232:N,CA,C,O,CB,CG1,CG2
 NEWMODEL:ALA 233:N,CA,C,O,CB
 NEWMODEL:GLY 262:N,CA,C,O
 NEWMODEL:CA E282H:CA Example 2

Suitable Substitutions in SAVINASE® for Addition of Amino Attachment Groups (—NH$_2$)

The known X-ray structure of SAVINASE® was used to find where suitable amino attachment groups may is added (Betzel et al, (1992), J. Mol. Biol. 223,p 427–445).

The 3D structure of, SAVINASE® is available in the Brookhaven Databank as 1svn.pbd. A related subtilisin is available as 1st3.pdb.

The sequence of SAVINASE® is shown in SEQ ID NO. 3 The sequence numbering used is that of subtilisin BPN', SAVINASE® having deletions relative to BPN' at positions: 36, 56, 158–159 and 163–164. The active site residues (functional site) are D32, H64 and S221.

The commands performed in Insight (BIOSYM) are shown in the command files makeKzone.bcl and makeKzone2.bcl below:

Conservative Substitutions:
makekzone.bcl
 Delete Subset *
 Color Molecule Atoms * Specified Specification 255,0, 255
 Zone Subset LYS :lys:NZ Static monomer/residue 10 Color_Subset 255,255,0
 Zone Subset NTERM :e1:N Static monomer/residue 10 Color_Subset 255,255,0
 #NOTE: editnextline ACTSITE residues according to the protein
 Zone Subset ACTSITE :e32,e64,e221 Static monomer/residue 8
 Color_Subset 255,255,0
 Combine Subset ALLZONE Union LYS NTERM
 Combine Subset ALLZONE Union ALLZONE ACTSITE
 #NOTE: editnextline object name according to the protein
 Combine Subset REST Difference SAVI8 ALLZONE
 List Subset REST Atom Output_File restatom.list
 List Subset REST monomer/residue Output_File restmole.list
 Color Molecule Atoms ACTSITE Specified Specification 255,0,0
 List Subset ACTSITE Atom Output_File actsiteatom.list
 List Subset ACTSITE monomer/residue Output_File actsitemole.list
 #
 Zone Subset REST5A REST Static Monomer/Residue 5-Color_Subset
 Combine Subset SUB5A Difference REST5A ACTSITE
 Combine Subset SUB5B Difference SUB5A REST
 Color Molecule Atoms SUB5B Specified Specification 255,255,255
 List Subset SUB5B Atom Output_File sub5batom.list
 List Subset SUB5B monomer/residue Output_File sub5bmole.list
 #Now identify sites for lys→arg substitutions and continue with makezone2.bcl
 #Use grep command to identify ARG in restatom.list, sub5batom.list & accsiteatom.list
Comments: 4
 In this case of SAVINASE® REST contains the Arginines Arg10, Arg170 and Arg 186, and SUB5B contains Arg19, Arg45, Arg145 and Arg247.
 These residues are all solvent exposed. The substitutions R10K, R19K, R45K, R145K, R170K, R186K and R247K are identified in SAVINASE® as sites for mutagenesis within the scope of this invention. The residues are substituted below in section 2, and further analysis done. The subset ACTSITE contains Lys94.
 The substitution K94R is a mutation removing Lysine as attachment group close to the active site.
Non-conservative Substitutions:
makeKzone2.bcl
 #sourcefile makezone2.bcl Claus von der Osten 961128
 #
 #having scanned lists (grep arg command) and identified sites for lys→arg substitutions

NOTE: editnextline object name according to protein

Copy Object -To__Clipboard -Displace SAVE8 newmodel Biopolymer

NOTE: editnextline object name according to protein Blank Object On SAVI8

NOTE: editnextlines with lys→arg positions

Replace Residue newmodel:e10 lys L

Replace Residue newmodel:e170 lys L

Replace Residue newmodel:e186 lys L

Replace Residue newmodel:e19 lys L

Replace Residue newmodel:e45 lys L

Replace Residue newmodel:e145 lys L

Replace Residue newmodel:e241 lys L

Now repeat analysis done prior to arg→lys, now including introduced lysines

Color Molecule Atoms newmodel Specified Specification 255,0,255

Zone Subset LYSx newmodel:lys:NZ Static monomer/residue 10

Color__Subset 255,255,0

Zone Subset NTERMx newmodel:e1:N Static monomer/residue 10

Color__Subset 255,255,0

NOTE: editnextline ACTSITEx residues according to the protein

Zone Subset ACTSITEx newmodel:e32,e64,e221 Static monomer/residue 8 Color__Subset 255,255,0

Combine Subset ALLZONEx Union LYSx NTERMx

Combine Subset ALLZONEx Union ALLZONEx ACTSITEx

Combine Subset RESTx Difference newmodel ALLZONEx

List Subset RESTx Atom Output__File restxatom.list

List Subset RESTx monomer/residue Output__File restxmole.list

Color Molecule Atoms ACTSITEx Specified Specification 255,0,0

List Subset ACTSITEx Atom Output__File actsitexatom.list

List Subset ACTSITEx monomer/residue Output__File actsitexmole.list

read restxatom.list or restxmole.list to identify sites for (not_arg)→lys subst. if needed Comments:

Of the residues in RESTx, the following are >5% exposed (see lists below): 5,14,22,38–40,42,75–76,82,86,103–105, 108,133–135,137,140,173,204,206,211–213,215–216,269. The following mutations are proposed in SAVINASE®: P5K, P14K, T22K, T38K, H39K, P40K, L42K, L75K, N76K, L82K, P86K, S103K, V104K, S105K, A108K, A133K, T134K, L135K, Q137K, N140K, N173K, N204K, Q206K, G211K, S212K, T213K, A215K, S216K, N269K. Relevant data for Example 2:

Solvent Accessibility Data for SAVINASE®:

| # SAVI8NOH2O | Fri Nov 29 13:32:07 MET 1996 |
|---|---|
| # residue | area |
| ALA__1 | 118.362808 |
| GLN__2 | 49.422764 |
| SER__3 | 61.982887 |
| VAL__4 | 71.620255 |
| PRO__5 | 21.737535 |
| TRP__6 | 58.718731 |
| GLY__7 | 4.328117 |
| ILE__8 | 6.664074 |
| SER__9 | 60.175900 |
| ARG__10 | 70.928963 |
| VAL__11 | 2.686934 |
| GLN__12 | 72.839996 |
| ALA__13 | 0.000000 |
| PRO__14 | 52.308453 |
| ALA__15 | 38.300892 |
| ALA__16 | 0.000000 |
| HIS__17 | 41.826324 |
| ASN__18 | 136.376602 |
| ARG__19 | 105.678642 |
| GLY__20 | 48.231510 |
| LEU__21 | 17.196377 |
| THR__22 | 36.781742 |
| GLY__23 | 0.000000 |
| SER__24 | 64.151276 |
| GLY__25 | 50.269905 |
| VAL__26 | 4.030401 |
| LYS__27 | 54.239555 |
| VAL__28 | 0.000000 |
| ALA__29 | 0.000000 |
| VAL__30 | 3.572827 |
| LEU__31 | 0.233495 |
| ASP__32 | 1.074774 |
| THR__33 | 1.973557 |
| GLY__34 | 3.638052 |
| ILE__35 | 8.044439 |
| SER__36 | 8.514903 |
| THR__37 | 122.598907 |
| HIS__38 | 18.834011 |
| PRO__39 | 76.570526 |
| ASP__40 | 0.000000 |
| LEU__41 | 19.684013 |
| ASN__42 | 88.870216 |
| ILE__43 | 56.117710 |
| ARG__44 | 110.647194 |
| GLY__45 | 26.935413 |
| GLY__46 | 35.515778 |
| ALA__47 | 21.495472 |
| SER__48 | 34.876190 |
| PHE__49 | 52.647541 |
| VAL__50 | 23.364208 |
| PRO__51 | 110.408752 |
| GLY__52 | 80.282906 |
| GLU__53 | 43.033707 |
| PRO__54 | 124.444336 |
| SER__55 | 60.284889 |
| THR__56 | 47.103241 |
| GLN__57 | 120.803505 |
| ASP__58 | 12.784743 |
| GLY__59 | 61.742443 |
| ASN__60 | 56.760231 |
| GLY__61 | 1.576962 |
| HIS__62 | 38.590118 |
| GLY__63 | 0.000000 |
| THR__64 | 0.537387 |
| HIS__65 | 0.968253 |
| VAL__66 | 1.612160 |
| ALA__67 | 0.00000G |
| GLY__68 | 2.801945 |
| THR__69 | 9.074596 |
| ILE__70 | 0.000000 |
| ALA__71 | 4.577205 |
| ALA__72 | 0.000000 |
| LEU__73 | 47.290039 |

-continued

SAVI8NOH2O  Fri Nov 29 13:32:07 MET 1996

| # residue | area |
|---|---|
| ASN_74 | 102.187248 |
| ASN_75 | 60.210400 |
| SER_76 | 84.614494 |
| ILE_77 | 66.098572 |
| GLY_78 | 17.979534 |
| VAL_79 | 5.642561 |
| LEU_80 | 13.025185 |
| GLY_81 | 0.000000 |
| VAL_82 | 0.268693 |
| ALA_83 | 0.000000 |
| PRO_84 | 18.193810 |
| SER_85 | 56.839039 |
| ALA_86 | 13.075745 |
| GLU_87 | 37.011765 |
| LEU_88 | 2.149547 |
| TYR_89 | 30.633518 |
| ALA_90 | 1.343467 |
| VAL_91 | 0.779450 |
| LYS_92 | 5.862781 |
| VAL_93 | 0.466991 |
| LEU_94 | 10.747736 |
| GLY_95 | 8.707102 |
| ALA_96 | 41.414677 |
| SER_97 | 96.066040 |
| GLY_98 | 33.374485 |
| SER_99 | 67.664116 |
| GLY_100 | 35.571117 |
| SER_101 | 54.096992 |
| VAL_102 | 52.695324 |
| SER_103 | 62.929684 |
| SER_104 | 8.683097 |
| ILE_105 | 15.852910 |
| ALA_106 | 14.509443 |
| GLN_107 | 94.463066 |
| GLY_108 | 0.000000 |
| LEU_109 | 0.537387 |
| GLU_110 | 63.227707 |
| TRP_111 | 55.500740 |
| ALA_112 | 0.502189 |
| GLY_113 | 11.908267 |
| ASN_114 | 107.208527 |
| ASN_115 | 78.811234 |
| GLY_116 | 41.453194 |
| MET_117 | 9.634291 |
| HIS_118 | 54.022118 |
| VAL_119 | 5.105174 |
| ALA_120 | 0.268693 |
| ASN_121 | 0.233495 |
| LEU_122 | 0.537387 |
| SER_123 | 4.004620 |
| LEU_124 | 21.927265 |
| GLY_125 | 55.952454 |
| SER_126 | 40.241180 |
| PRO_127 | 107.409439 |
| SER_128 | 57.988609 |
| PRO_129 | 85.021118 |
| SER_130 | 20.460915 |
| ALA_131 | 57.404362 |
| THR_132 | 74.438805 |
| LEU_133 | 12.091203 |
| GLU_134 | 73.382019 |
| GLN_135 | 114.870010 |
| ALA_136 | 2.122917 |
| VAL_137 | 1.074774 |
| ASN_138 | 55.622704 |
| SER_139 | 29.174965 |
| ALA_140 | 0.268693 |
| THR_141 | 27.962946 |
| SER_142 | 87.263145 |
| ARG_143 | 88.201218 |
| GLY_144 | 38.477882 |
| VAL_145 | 2.079151 |
| LEU_146 | 13.703363 |
| VAL_147 | 2.690253 |
| VAL_148 | 1.074774 |

-continued

SAVI8NOH2O  Fri Nov 29 13:32:07 MET 1996

| # residue | area |
|---|---|
| ALA_149 | 0.000000 |
| ALA_150 | 4.356600 |
| SER_151 | 0.000000 |
| GLY_152 | 12.628590 |
| ASN_153 | 84.248703 |
| SER_154 | 77.662354 |
| GLY_155 | 25.409861 |
| ALA_156 | 38.074570 |
| GLY_157 | 40.493744 |
| SER_158 | 53.915291 |
| ILE_159 | 4.352278 |
| SER_160 | 12.458543 |
| TYR_161 | 29.670284 |
| PRO_162 | 4.030401 |
| ALA_163 | 0.968253 |
| ARG_164 | 84.059120 |
| TYR_165 | 28.641129 |
| ALA_166 | 68.193314 |
| ASN_167 | 61.686481 |
| ALA_168 | 0.537387 |
| MET_169 | 0.586837 |
| ALA_170 | 0.000000 |
| VAL_171 | 0.000000 |
| GLY_172 | 0.000000 |
| ALA_173 | 0.933982 |
| THR_174 | 3.013133 |
| ASP_175 | 34.551376 |
| GLN_176 | 96.873039 |
| ASN_177 | 98.664368 |
| ASN_178 | 41.197159 |
| ASN_179 | 60.263512 |
| ARG_180 | 64.416336 |
| ALA_181 | 7.254722 |
| SER_182 | 91.590881 |
| PHE_183 | 52.126518 |
| SER_184 | 2.101459 |
| GLN_185 | 15.736279 |
| TYR_186 | 44.287792 |
| GLY_187 | 5.114592 |
| ALA_188 | 69.406563 |
| GLY_189 | 36.926083 |
| LEU_190 | 16.511177 |
| ASP_191 | 7.705349 |
| ILE_192 | 0.268693 |
| VAL_193 | 4.299094 |
| ALA_194 | 0.000000 |
| PRO_195 | 0.806080 |
| GLY_196 | 0.000000 |
| VAL_197 | 25.257177 |
| ASN_198 | 82.177422 |
| VAL_199 | 10.747736 |
| GLN_200 | 80.374527 |
| SER_201 | 2.008755 |
| THR_202 | 0.000000 |
| TYR_203 | 80.679886 |
| PRO_204 | 34.632195 |
| GLY_205 | 74.536827 |
| SER_206 | 74.964920 |
| THR_207 | 57.070065 |
| TYR_208 | 82.895500 |
| ALA_209 | 22.838940 |
| SER_210 | 69.045639 |
| LEU_211 | 49.708279 |
| ASN_212 | 86.905457 |
| GLY_213 | 2.686934 |
| THR_214 | 4.669909 |
| SER_215 | 15.225292 |
| MET_216 | 7.261287 |
| ALA_217 | 0.000000 |
| THR_218 | 0.000000 |
| PRO_219 | 0.806080 |
| HIS_220 | 2.662697 |
| VAL_221 | 0.268693 |
| ALA_222 | 0.000000 |
| GLY_223 | 0.000000 |

-continued

| # SAVI8NOH2O | Fri Nov 29 13:32:07 MET 1996 |
|---|---|
| # residue | area |
| ALA_224 | 7.206634 |
| ALA_225 | 1.039576 |
| ALA_226 | 0.268693 |
| LEU_227 | 1.074774 |
| VAL_228 | 1.541764 |
| LYS_229 | 39.262505 |
| GLN_230 | 54.501614 |
| LYS_231 | 81.154129 |
| ASN_232 | 30.004124 |
| PRO_233 | 91.917931 |
| SER_234 | 102.856705 |
| TRP_235 | 64.639481 |
| SER_236 | 51.797619 |
| ASN_237 | 24.866917 |
| VAL_238 | 78.458466 |
| GLN_239 | 73.981461 |
| ILE_240 | 14.474245 |
| ARG_241 | 41.242931 |
| ASN_242 | 64.644814 |
| HIS_243 | 50.671440 |
| LEU_244 | 5.127482 |
| LYS_245 | 48.820000 |
| ASN_246 | 115.264534 |
| THR_247 | 22.205376 |
| ALA_248 | 16.415077 |
| THR_249 | 60.503101 |
| SER_250 | 74.511597 |
| LEU_251 | 48.861599 |
| GLY_252 | 39.124340 |
| SER_253 | 49.811481 |
| THR_254 | 88.421982 |
| ASN_255 | 72.490181 |
| LEU_256 | 54.835758 |
| TYR_257 | 38.798912 |
| GLY_258 | 3.620916 |
| SER_259 | 35.017368 |
| GLY_260 | 0.537387 |
| LEU_261 | 8.598188 |
| VAL_262 | 4.519700 |
| ASN_263 | 16.763659 |
| ALA_264 | 3.413124 |
| GLU_265 | 37.942276 |
| ALA_266 | 15.871746 |
| ALA_267 | 3.947115 |
| THR_268 | 2.475746 |
| ARG_269 | 176.743362 |
| ION_270 | 0.000000 |
| ION_271 | 5.197493 |

Subset REST:
  restmole.list
Subset REST:
  SAVI8:E5–E15,E17–E18,E22,E38–E40,E42–E43,
    E73–E76,E82–E86,E103–E105,
  SAVI8:E108–E109,E111–E112,E115–E116,E122,
    E128–E144,E149–E150,E156–E157,
  SAVI8:E160–E162,E165–E168,E170–E171,E173,
    E180–E188,E190–E192,E200,
  SAVI8:E203–E204,E206,E211–E213,E215–E216,
    E227–E230,E255–E259,E261–E262,
  SAVI8:E267–E269
  restatom.list
Subset REST:
  SAVI8:PRO E5:N,CD,CA,CG,CB,C,O
  SAVI8:TRP E6:N,CA,CD2,CE2,NE1,CD1,CG,CE3,
    CZ3,CH2,CZ2,CB,C,O
  SAVI8:GLY E7:N,CA,C,O
  SAVI8:ILE E8:N,CA,CD1,CG1,CB,CG2,C,O
  SAVI8:SER E9:N,CA,OG,CB,C,O
  SAVI8:ARG E10:N,CA,NH2,NH1,CZ,NE,CD,CG,CB,
    C,O
  SAVI8:VAL E11:N,CA,CG2,CG1,CB,C,O
  SAVI8:GLN E12:N,CA,NE2,OE1,CD,CG,CB,C,O
  SAVI8:ALA E13:N,CA,CB,C,O
  SAVI8:PRO E14:N,CD,CA,CG,CB,C,O
  SAVI8:ALA E15:N,CA,CB,C,O
  SAVI8:HIS E17:N,CA,CD2,NE2,CE1,ND1,CG,CB,C,O
  SAVI8:ASN E18:N,CA,ND2,OD1,CG,CB,C,O
  SAVI8:THR E22:N,CA,CG2,OG1,CB,C,O
  SAVI8:THR E38:N,CA,CG2,OG1,CB,C,O
  SAVI8:HIS E39:N,CA,CD2,NE2,CE1,ND1,CG,CB,C,O
  SAVI8:PRO E40:N,CD,CA,CG,CB,C,O
  SAVI8:LEU E42:N,CA,CD2,CD1,CG,CB,C,O
  SAVI8:ASN E43:N,CA,ND2,OD1,CG,CB,C,O
  SAVI8:ALA E73:N,CA,CB,C,O
  SAVI8:ALA E74:N,CA,CB,C,O
  SAVI8:LEU E75:N,CA,CD2,CD1,CG,CB,C,O
  SAVI8:ASN E76:N,CA,ND2,OD1,CG,CB,C,O
  SAVI8:LEU E82:N,CA,CD2,CD1,CG,CB,C,O
  SAVI8:GLY E83:N,CA,C,O
  SAVI8:VAL E84:N,CA,CG2,CG1,CB,C,O
  SAVI8:ALA E85:N,CA,CB,C,O
  SAVI8:PRO E86:N,CD,CA,CG,CB,C,O
  SAVI8:SER E103:N,CA,OG,CB,C,O
  SAVI8:VAL E104:N,CA,CG2,CG1,CB,C,O
  SAVI8:SER E105:N,CA,OG,CB,C,O
  SAVI8:ALA E108:N,CA,CB,C,O
  SAVI8:GLN E109:N,CA,NE2,OE1,CD,CG,CB,C,O
  SAVI8:LEU E111:N,CA,CD2,CD1,CG,CB,C,O
  SAVI8:GLU E112:N,CA,OE2,OE1,CD,CG,CB,C,O
  SAVI8:GLY E115:N,CA,C,O
  SAVI8:ASN E116:N,CA,ND2,OD1,CG,CB,C,O
  SAVI8:ALA E122:N,CA,CB,C,O
  SAVI8:SER E128:N,CA,OG,CB,C,O
  SAVI8:PRO E129:N,CD,CA,CG,CB,C,O
  SAVI8:SER E130:N,CA,OG,CB,C,O
  SAVI8:PRO E131:N,CD,CA,CG,CB,C,O
  SAVI8:SER E132:N,CA,OG,CB,C,O
  SAVI8:ALA E133:N,CA,CB,C,O
  SAVI8:THR E134:N,CA,CG2,OG1,CB,C,O
  SAVI8:LEU E135:N,CA,CD2,CD1,CG,CB,C,O
  SAVI8:GLU E136:N,CA,OE2,OE1,CD,CG,CB,C,O
  SAVI8:GLN E137:N,CA,NE2,OE1,CD,CG,CB,C,O
  SAVI8:ALA E138:N,CA,CB,C,O
  SAVI8:VAL E139:N,CA,CG2,CG1,CB,C,O
  SAVI8:ASN E140:N,CA,ND2,OD1,CG,CB,C,O
  SAVI8:SER E141:N,CA,OG,CB,C,O
  SAVI8:ALA E142:N,CA,CB,C,O
  SAVI8:THR E143:N,CA,CG2,OG1,CB,C,O
  SAVI8:SER E144:N,CA,OG,CB,C,O
  SAVI8:VAL E149:N,CA,CG2,CG1,CB,C,O
  SAVI8:VAL E150:N,CA,CG2,CG1,CB,C,O
  SAVI8:SER E156:N,CA,OG,CB,C,O
  SAVI8:GLY E157:N,CA,C,O
  SAVI8:ALA E160:N,CA,CB,C,O
  SAVI8:GLY E161:N,CA,C,O SAVI8:SER E162:N,CA,OG,CB,C,O
SAVI8:ILE E165:N,CA,CD1,CG1,CB,CG2,C,O
SAVI8:SER E166:N,CA,OG,CB,C,O
SAVI8:TYR E167:N,CA,OH,CZ,CD2,CE2,CE1,CD1, CG,CB,C,O
SAVI8:PRO E168:N,CD,CA,CG,CB,C,O
SAVI8:ARG E170:N,CA,NH2,NH1,CZ,NE,CD,CG,CB, C,O
SAVI8:TYR E171:N,CA,OH,CZ,CD2,CE2,CE1,CD1, CG,CB,C,O
SAVI8:ASN E173:N,CA,ND2,OD1,CG,CB,C,O
SAVI8:THR E180:N,CA,CG2,OG1,CB,C,O
SAVI8:ASP E181:N,CA,OD2,OD1,CG,CB,C,O
SAVI8:GLN E182:N,CA,NE2,OE1,CD,CG,CB,C,O
SAVI8:ASN E183:N,CA,ND2,OD1,CG,CB,C,O
SAVI8:ASN E184:N,CA,ND2,OD1,CG,CB,C,O
SAVI8:ASN E185:N,CA,ND2,OD1,CG,CB,C,O
SAVI8:ARG E186:N,CA,NH2,NH1,CZ,NE,CD,CG,CB, C,O
SAVI8:ALA E187:N,CA,CB,C,O
SAVI8:SER E188:N,CA,OG,CB,C,O
SAVI8:SER E190:N,CA,OG,CB,C,O
SAVI8:GLN E191:N,CA,NE2,OE1,CD,CG,CB,C,O
SAVI8:TYR E192:N,CA,OH,CZ,CD2,CE2,CE1,CD1$_1$, CG,CB,C,O
SAVI8:ALA E200:N,CA,CB,C,O
SAVI8:VAL E203:N,CA,CG2,CG1,CB,C,O
SAVI8:ASN E204:N,CA,ND2,OD1,CG,CB,C,O
SAVI8:GLN E206:N,CA,NE2,OE1,CD,CG,CB,C,O
SAVI8:GLY E211:N,CA,C,O
SAVI8:SER E212:N,CA,OG,CB,C,O
SAVI8:THR E213:N,CA,CG2,OG1,CB,C,O
SAVI8:ALA E215:N,CA,CB,C,O
SAVI8:SER E216:N,CA,OG,CB,C,O
SAVI8:VAL E227:N,CA,CG2,CG1,CB,C,O
SAVI8:ALA E228:N,CA,CB,C,O
SAVI8:GLY E229:N,CA,C,O
SAVI8:ALA E230:N,CA,CB,C,O
SAVI8:THR E255:N,CA,CG2,OG1,CB,C,O
SAVI8:SER E256:N,CA,OG,CB,C,O
SAVI8:LEU E257:N,CA,CD2,CD1,CG,CB,C,O
SAVI8:GLY E258:N,CA,C,O
SAVI8:SER E259:N,CA,OG,CB,C,O
SAVI8:ASN E261:N,CA,ND2,OD1,CG,CB,C,O
SAVI8:LEU E262:N,CA,CD2,CD1,CG,CB,C,O
SAVI8:LEU E267:N,CA,CD2,CD1,CG,CB,C,O
SAVI8:VAL E268:N,CA,CG2,CG1,CB,C,O
SAVI8:ASN E269:N,CA,ND2,OD1,CG,CB,C,O
Subset SUB5B:
sub5bmole.list
Subset SUB5B:
  SAVI8:E2–E4,E16,E19–E21,E23–E24,E28,E37,E41, E44–E45, E77–E81,E87–E88,
  SAVI8:E90,E113–E114,E117–E118,E120–E121, E145–E148,E169,E172,E174–E176,
  SAVI8:E193–E196,E198–E199,E214,E231–E234,E236, E243,E247,E250,E253–E254,
  SAVI8:E260,E263–E266,E270–E273,M276H–M277H
sub5batom.list
Subset SUB5B:
  SAVI8:GLN E2:N,CA,NE2,OE1,CD,CG,CB,C,O
  SAVI8:SER E3:N,CA,OG,CB,C,O
  SAVI8:VAL E4:N,CA,CG2,CG1,CB,C,O
  SAVI8:ALA E16:N,CA,CB,C,O
  SAVI8:ARG E19:N,CA,NH2,NH1,CZ,NE,CD,CG,CB, C,O
  SAVI8:GLY E20:N,CA,C,O
  SAVI8:LEU E21:N,CA,CD2,CD1,CG,CB,C,O
  SAVI8:GLY.E23:N,CA,C,O
  SAVI8:SER E24:N,CA,OG,CB,C,O
  SAVI8:VAL E28:N,CA,CG2,CG1,CB,C,O
  SAVI8:SER E37:N,CA,OG,CB,C,O
  SAVI8:ASP E41:N,CA,OD2,OD1,CG,CB,C,O
  SAVI8:ILE E44:N,CA,CD1,CG1,CB,CG2,C,O
  SAVI8:ARG E45:N,CA,NH2,NH1,CZ,NE,CD,CG,CB, C,O
  SAVI8:ASN E77:N,CA,ND2,OD1,CG,CB,C,O
  SAVI8:SER E78:N,CA,OG,CB,C,O
  SAVI8:ILE E79:N,CA,CD1,CG1,CB,CG2,C,O
  SAVI8:GLY E80:N,CA,C,O
  SAVI8:VAL E81:N,CA,CG2,CG1,CB,C,O
  SAVI8:SER E87:N,CA,OG,CB,C,O
  SAVI8:ALA E88:N,CA,CB,C,O
  SAVI8:LEU E90:N,CA,CD2,CD1,CG,CB,C,O
  SAVI8:TRP E113:N,CA,CD2,CE2,NE1,CD1,CG,CE3, CZ3,CH2,CZ2,CB,C,O
  SAVI8:ALA E114:N,CA,CB,C,O
  SAVI8:ASN E117:N,CA,ND2,OD1,CG,CB,C,O
  SAVI8:GLY E118:N,CA,C,O
  SAVI8:HIS E120:N,CA,CD2,NE2,CE1,ND1,CG,CB, C,O
  SAVI8:VAL E121:N,CA,CG2,CG1,CB,C,O
  SAVI8:ARG E145:N,CA,NH2,NH1,CZ,NE,CD,CG,CB, C,O
  SAVI8:GLY E146:N,CA,C,O
  SAVI8:VAL E147:N,CA,CG2,CG1,CB,C,O
  SAVI8:LEU E148:N,CA,CD2,CD1,CG,CB,C,O
  SAVI8:ALA E169:N,CA,CB,C,O
  SAVI8:ALA E172:N,CA,CB,C,O
  SAVI8:ALA E174:N,CA,CB,C,O
  SAVI8:MET E175:N,CA,CE,SD,CG,CB,C,O
  SAVI8:ALA E176:N,CA,CB,C,O
  SAVI8:GLY E193:N,CA,C,O
  SAVI8:ALA E194:N,CA,CB,C,O
  SAVI8:GLY E195:N,CA,C,O
  SAVI8:LEU E196:N,CA,CD2,CD1,CG,CB,C,O
  SAVI8:ILE E198:N,CA,CD1,CG1,CB,CG2,C,O
  SAVI8:VAL E199:N,CA,CG2,CG1,CB,C,O
  SAVI8:TYR E214:N,CA,OH,CZ,CD2,CE2,CE1,CD1, CG,CB,C,O
  SAVI8:ALA E231:N,CA,CB,C,O
  SAVI8:ALA E232:N,CA,CB,C,O
  SAVI8:LEU E233:N,CA,CD2,CD1,CG,CB,C,O
  SAVI8:VAL E234:N,CA,CG2,CG1,CB,C,O
  SAVI8:GLN E236:N,CA,NE2,OE1,CD,CG,CB,C,O
  SAVI8:ASN E243:N,CA,ND2,OD1,CG,CB,C,O SAVI8:ARG E247:N,CA,NH2,NH1,CZ,NE,CD,CG,CB, C,O
SAVI8:LEU E250:N,CA,CD2,CD1,CG,CB,C,O
SAVI8:THR E253:N,CA,CG2,OG1,CB,C,O
SAVI8:ALA E254:N,CA,CB,C,O
SAVI8:THR E260:N,CA,CG2,OG1,CB,C,O
SAVI8:TYR E263:N,CA,OH,CZ,CD2,CE2,CE1,CD1, CG,CB,C,O
SAVI8:GLY E264:N,CA,C,O
SAVI8:SER E265:N,CA,OG,CB,C,O
SAVI8:GLY E266:N,CA,C,O
SAVI8:ALA E270:N,CA,CB,C,O
SAVI8:GLU E271:N,CA,OE2,OE1,CD,CG,CB,C,O
SAVI8:ALA E272:N,CA,CB,C,O
SAVI8:ALA E273:N,CA,CB,C,O
SAVI8:ION M276H:CA
SAVI8:ION M277H:CA
Subset ACTSITE:
actsitemole.list
Subset ACTSITE:
SAVI8:E29–E35,E48–E51,E54,E58–E72,E91–E102, E106–E107,E110,E123–E127,
SAVI8: E151–E155,E177–E179,E189,E201–E202,E205, E207–E210,E217–E226
actsiteatom.list
Subset ACTSITE:
SAVI8:ALA E29:N,CA,CB,C,O
SAVI8:VAL E30:N,CA,CG2,CG1,CB,C,O
SAVI8:LEU E31:N,CA,CD2,CD1,CG,CB,C,O
SAVI8:ASP E32:N,CA,OD2,OD1,CG,CB,C,O
SAVI8:THR E33:N,CA,CG2,OG1,CB,C,O
SAVI8:GLY E34:N,CA,C,O
SAVI8:ILE E35:N,CA,CD1,CG1,CB,CG2,C,O
SAVI8:ALA E48:N,CA,CB,C,O
SAVI8:SER E49:N,CA,OG,CB,C,O
SAVI8:PHE E50:N,CA,CD2,CE2,CZ,CE1,CD1,CG,CB, C,O
SAVI8:VAL E51:N,CA,CG2,CG1,CB,C,O
SAVI8:GLU E54:N,CA,OE2,OE1,CD,CG,CB,C,O
SAVI8:THR E58:N,CA,CG2,OG1,CB,C,O
SAVI8:GLN E59:N,CA,NE2,OE1,CD,CG,CB,C,O
SAVI8:ASP E60:N,CA,OD2,OD1,CG,CB,C,O
SAVI8:GLY E61:N,CA,C,O
SAVI8:ASN E62:N,CA,ND2,OD1,CG,CB,C,O
SAVI8:GLY E63:N,CA,C,O
SAVI8:HIS E64:N,CA,CD2,NE2,CE1,ND1,CG,CB,C,O
SAVI8:GLY E65:N,CA,C,O
SAVI8:THR E66:N,CA,CG2,OG1,CB,C,O
SAVI8:HIS E67:N,CA,CD2,NE2,CE1,ND1,CG,CB,C,O
SAVI8:VAL E68:N,CA,CG2,CG1,CB,C,O
SAVI8:ALA E69:N,CA,CB,C,O
SAVI8:GLY E70:N,CA,C,O
SAVI8:THR E71:N,CA,CG2,OG1,CB,C,O
SAVI8:ILE E72:N,CA,CD1,CG1,CB,CG2,C,O
SAVI8:TYR E91:N,CA,OH,CZ,CD2,CE2,CE1,CD1,CG, CB,C,O
SAVI8:ALA E92:N,CA,CB,C,O
SAVI8:VAL E93:N,CA,CG2,CG1,CB,C,O
SAVI8:LYS E94:N,CA,NZ,CE,CD,CG,CB,C,O
SAVI8:VAL E95:N,CA,CG2,CG1,CB,C,O
SAVI8:LEU E96:N,CA,CD2,CD1,CG,CB,C,O
SAVI8:GLY E97:N,CA,C,O
SAVI8:ALA E98:N,CA,CB,C,O
SAVI8:SER E99:N,CA,OG,CB,C,O
SAVI8:GLY E100:N,CA,C,O
SAVI8:SER E101:N,CA,OG,CB,C,O
SAVI8:GLY E102:N,CA,C,O
SAVI8:SER E106:N,CA,OG,CB,C,O
SAVI8:ILE E107:N,CA,CD1,CG1,CB,CG2,C,O
SAVI8:GLY E110:N,CA,C,O
SAVI8:ASN E123:N,CA,ND2,OD1,CG,CB,C,O
SAVI8:LEU E124:N,CA,CD2,CD1,CG,CB,C,O
SAVI8:SER E125:N,CA,OG,CB,C,O
SAVI8:LEU E126:N,CA,CD2,CD1,CG,CB,C,O
SAVI8:GLY E127:N,CA,C,O
SAVI8:ALA E151:N,CA,CB,C,O
SAVI8:ALA E152:N,CA,CB,C,O
SAVI8:SER E153:N,CA,OG,CB,C,O
SAVI8:GLY E154:N,CA,C,O
SAVI8:ASN E155:N,CA,ND2,OD1,CG,CB,C,O
SAVI8:VAL E177:N,CA,CG2,CG1,CB,C,O
SAVI8:GLY E178:N,CA,C,O
SAVI8:ALA E179:N,CA,CB,C,O
SAVI8:PHE E189:N,CA,CD2,CE2,CZ, CE1,CD1,CG, CB,C,O
SAVI8:PRO E201:N,CD,CA,CG,CB,C,O
SAVI8:GLY E202:N,CA,C,O
SAVI8:VAL E205:N,CA,CG2,CG1,CB,C,O
SAVI8:SER E207:N,CA,OG,CB,C,O
SAVI8:THR E208:N,CA,CG2,OG1,CB,C,O
SAVI8:TYR E209:N,CA,OH,CZ,CD2,CE2,CE1,CD1, CG,CB,C,O
SAVI8:PRO E210:N,CD,CA,CG,CB,C,O
SAVI8:LEU E217:N,CA,CD2,CD1,CG,CB,C,O
SAVI8:ASN E218:N,CA,ND2,OD1,CG,CB,C,O
SAVI8:GLY E219:N,CA,C,O
SAVI8:THR E220:N,CA,CG2,OG1,CB,C,O
SAVI8:SER E221:N,CA,OG,CB,C,O
SAVI8:MET E222:N,CA,CE,SD,CG,CB,C,O
SAVI8:ALA E223:N,CA,CB,C,O
SAVI8:THR E224:N,CA,CG2,OG1,CB,C,O
SAVI8:PRO E225:N,CD,CA,CG,CB,C,O
SAVI8:HIS E226:N,CA,CD2,NE2,CE1,ND1,CG,CB, C,O
Subset RESTx:
restxmole.list
Subset RESTx:
NEWMODEL:E5,E13–E14,E22,E38–E40,E42, E73–E76,E82–E86,E103–E105,
NEWMODEL:E108,E122,E133–E135,E137–E140, E149–E150,E173,E204,E206,
NEWMODEL:E211–E213,E215–E216,E227–E229, E258,E269
restxatom.list Subset RESTx:
  NEWMODEL:PRO E5:N,CD,CA,CG,CB,C,O
  NEWMODEL:ALA E13:N,CA,CB,C,O
  NEWMODEL:PRO E14:N,CD,CA,CG,CB,C,O
  NEWMODEL:THR E22:N,CA,CG2,OG1,CB,C,O
  NEWMODEL:THR E38:N,CA,CG2,OG1,CB,C,O
  NEWMODEL:HIS E39:N,CA,CD2,NE2,CE1,ND1,CG,CB,C,O
  NEWMODEL:PRO E40:N,CD,CA,CG,CB,C,O
  NEWMODEL:LEU E42:N,CA,CD2,CD1,CG,CB,C,O
  NEWMODEL:ALA E73:N,CA,CB,C,O
  NEWMODEL:ALA E74:N,CA,CB,C,O
  NEWMODEL:LEU E75:N,CA,CD2,CD1,CG,CB,C,O
  NEWMODEL:ASN E76:N,CA,ND2,OD1,CG,CB,C,O
  NEWMODEL:LEU E82:N,CA,CD2,CD1,CG,CB,C,O
  NEWMODEL:GLY E83:N,CA,C,O
  NEWMODEL:VAL E84:N,CA,CG2,CG1,CB,C,O
  NEWMODEL:ALA E85:N,CA,CB,C,O
  NEWMODEL:PRO E86:N,CD,CA,CG,CB,C,O
  NEWMODEL:SER E103:N,CA,OG,CB,C,O
  NEWMODEL:VAL E104:N,CA,CG2,CG1,CB,C,O
  NEWMODEL:SER E105:N,CA,OG,CB,C,O
  NEWMODEL:ALA E108:N,CA,CB,C,O
  NEWMODEL:ALA E122:N,CA,CB,C,O
  NEWMODEL:ALA E133:N,CA,CB,C,O
  NEWMODEL:THR E134:N,CA,CG2,OG1,CB,C,O
  NEWMODEL:LEU E135:N,CA,CD2,CD1,CG,CB,C,O
  NEWMODEL:GLN E137:N,CA,NE2,OE1,CD,CG,CB,C,O
  NEWMODEL:ALA E138:N,CA,CB,C,O
  NEWMODEL:VAL E139:N,CA,CG2,CG1,CB,C,O
  NEWMODEL:ASN E140:N,CA,ND2,CD1,CG,CB,C,O
  NEWMODEL:VAL E149:N,CA,CG2,CG1,CB,C,O
  NEWMODEL:VAL E150:N,CA,CG2,CG1,CB,C,O
  NEWMODEL:ASN E173:N,CA,ND2,OD1,CG,CB,C,O
  NEWMODEL:ASN E204:N,CA,ND2,OD1,CG,CB,C,O
  NEWMODEL:GLN E206:N,CA,NE2,OE1,CD,CG,CB,C,O
  NEWMODEL:GLY E211:N,CA,C,O
  NEWMODEL:SER E212:N,CA,OG,CB,C,O
  NEWMODEL:THR E213:N,CA,CG2,OG1,CB,C,O
  NEWMODEL:ALA E215:N,CA,CB,C,O
  NEWMODEL:SER E216:N,CA,OG,CB,C,O
  NEWMODEL:VAL E227:N,CA,CG2,CG1,CB,C,O
  NEWMODEL:ALA E228:N,CA,CB,C,O
  NEWMODEL:GLY E229:N,CA,C,O
  NEWMODEL:GLY E258:N,CA,CO
  NEWMODEL:ASN E269:N,CA,ND2,OD1,CG,CB,C,O Example 3
Suitable Substitutions in PD498 for Addition of Carboxylic Acid Attachment Groups (—COOH)

The 3D structure of PD498 was modeled as described in Example 1. Suitable locations for addition of carboxylic attachment groups (Aspartatic acids and Glutamic acids) were found as follows. The procedure described in Example 1 was followed. The commands performed in Insight (BIOSYM) are shown in the command files makeDEzone.bcl and makeDEzone2.bcl below:

Conservative Substutitions:
makeDEzone.bcl
  Delete Subset *
  Color Molecule Atoms * Specified Specification255,0,255
  Zone Subset ASP :asp:od* Static monomer/residue 10
    Color_Subset 255,255,0
  Zone Subset GLU :glu:oe* Static monomer/residue 10
    Color_Subset 255,255,0
  #NOTE: editnextline C-terminal residue number according to the protein
  Zone Subset CTERM :280:0 Static monomer/residue 10
    Color_Subset 255,255,0
  #NOTE: editnextline ACTSITE residues according to the protein
  Zone Subset ACTSITE :39,72,226 Static monomer/residue 8
  Color_Subset 255,255,0
  Combine Subset ALLZONE Union ASP GLU
  Combine Subset ALLZONE Union ALLZONE CTERM
  Combine Subset ALLZONE Union ALLZONE ACTSITE
  #NOTE: editnextline object name according to the protein
  Combine Subset REST Difference PD498FINALMODEL ALLZONE
  List Subset REST Atom output_File restatom.list
  List Subset REST monomer/residue Output_File restmole.list
  Color Molecule Atoms ACTSITE Specified Specification 255,0,0
  List Subset ACTSITE Atom Output_File actsiteatom.list
  List Subset ACTSITE monomer/residue Output_File actsitemole.list
  #
  Zone Subset REST5A REST Static Monomer/Residue 5-
    Color_Subset
  Combine Subset SUB5A Difference REST5A ACTSITE
  Combine Subset SUB5B Difference SUB5A REST
  Color Molecule Atoms SUB5B Specified Specification 255,255,255
  List Subset SUB5B Atom Output_File sub5batom.list
  List Subset SUB5B monomer/residue Output_File sub5bmole.list
  #Now identify sites for asn→asp & gln→glu substitutions and . . .
  #continue with makezone2.bcl.
  #Use grep command to identify asn/gln in restatom.list . . .
  #sub5batom.list & accsiteatom.list
Comments:
  The subset REST contains Gln33 and Asn245, SUB5B contains Gln12, Gln126, Asn209, Gln242, Asn246, Gln248 and Asn266, all of which are solvent exposed.
  The substitutions Q12E or Q12D, Q33E or Q33D, Q126E or Q126D, N209D or N209E, Q242E or Q242D, N245D or N245E, N246D or N246E, Q248E or Q248D and N266D or N266E are identified in PD498 as sites for mutagenesis within the scope of this invention. Residues are substituted below in section 2, and further analysis done:

Non-conservative Substitutions:
makeDEzone2.bcl
```
    #sourcefile makezone2.bcl Claus von der Osten 961128
    #
    #having scanned lists (grep gln/asn command) and iden-
        tified
    sites for . . .
    #asn→asp & gln→glu substitutions
    #NOTE: editnextline object name according to protein
    Copy Object -To_Clipboard -Displace
        PD498FINALMODEL newmodel Biopolymer
    #NOTE: editnextline object name according to protein
    Blank Object On PD498FINALMODEL
    #NOTE: editnextlines with asn→asp & gln→glu posi-
        tions
    Replace Residue newmodel:33 glu L
    Replace Residue newmodel:245 asp L
    Replace Residue newmodel:12 glu L
    Replace Residue newmodel:126 glu L
    Replace Residue newmodel:209 asp L
    Replace Residue newmodel:242 glu L
    Replace Residue newmodel:246 asp L
    Replace Residue newmodel:248 glu L
    Replace Residue newmodel:266 asp L
    #
    #Now repeat analysis done prior to asn→asp & gln→glu,
        . . .
    #now including introduced asp & glu
    Color Molecule Atoms newmodel Specified Specification
        255,0,255
    Zone Subset ASPx newmodel:Asp:od* Static monomer/
        residue 10
    Color_Subset 255,255,0
    Zone Subset GLUx newmodel:glu:oe* Static monomer/
        residue 10
    Color_Subset 255,255,0
    #NOTE: editnextline C-terminal residue number accord-
        ing to the protein
    Zone Subset CTERMx newmodel:280: O Static
        monomer/residue 10
    Color_Subset 255,255,0
    #NOTE. editnextline ACTSITEx residues according to
        the protein
    Zone Subset ACTSITEx newmodel:39,72,226 Static
        monomer/residue
    8 Color_Subset 255,255,0
    Combine Subset ALLZONEx Union ASPx GLUx
    Combine Subset ALLZONEx Union ALLZONEx
        CTERMX
    Combine Subset ALLZONEx Union ALLZONEx
        ACTSITEx
    Combine Subset RESTx Difference newmodel
        ALLZONEx
    List Subset RESTx Atom output_File restxatom.list
    List Subset RESTx monomer/residue Output_File restx-
        mole.list
    #
    Color Molecule Atoms ACTSITEx Specified Specifica-
        tion 255,0,0
    List Subset ACTSITEx Atom Output_File actsitexatom-
        .list
    List Subset ACTSITEx monomer/residue Output_File
        actsitexmole.list
    #
    #read restxatom.list or restxmole.list to identify sites for
        (not_gluasp)→gluasp . . .
    #subst. if needed
```
Comments:

The subset RESTx contains only two residues: A233 and G234, none of which are solvent exposed. No further mutagenesis is required to obtain complete protection of the surface. However, it may be necessary to remove some of the reactive carboxylic groups in the active site region to ensure access to the active site of PD498. Acidic residues within the subset ACTSITE are: D39, D58, D68 and D106. Of these only the two latter are solvent exposed and D39 is a functional residue. The mutations D68N, D68Q, D106N and D106Q were found suitable according to the present invention.

Relevant data for Example 3: Solvent accessibility data for PD498MODEL: see Example 1 above.

Subset REST:
restmole.list
Subset REST:

```
PD498FINALMODEL:10–11,33–35,54–55,129–130,221,233–234,236,240,243,
PD498FINALMODEL:245,262,264–265
``` restatom.list
Subset REST:

```
PD498FINALMODEL:ALA 10:N,CA,C,O,CB
PD498FINALMODEL:TYR 11:N,CA,C,O,CB,CG,CD1,CD2,CE1,CE2,CZ,OH
PD498FINALMODEL:GLN 33:N,CA,C,O,CB,CG,CD,OE1,NE2
PD498FINALMODEL:THR 34:N,CA,C,O,CB,OG1,CG2
PD498FINALMODEL:VAL 35:N,CA,C,O,CB,CG1,CG2
PD498FINALMODEL:ILE 54:N,CA,C,O,CB,CG1,CG2,CD1
PD498FINALMODEL:LYS 55:N,CA,C,O,CB,CG,CD,CE,NZ
PD498FINALMODEL:LYS 129:N,CA,C,O,CB,CG,CD,CE,NZ
PD498FINALMODEL:VAL 130:N,CA,C,O,CB,CG1,CG2
PD498FINALMODEL:TYR 221:N,CA,C,O,CB,CG,CD1,CD2,CE1,CE2,CZ,OH
PD498FINALMODEL:ALA 233:N,CA,C,O,CB
PD498FINALMODEL:GLY 234:N,CA,C,O
PD498FINALMODEL:ALA 236:N,CA,C,O,CB
PD498FINALMODEL:ALA 240:N,CA,C,O,CB
PD498FINALMODEL:GLY 243:N,CA,C,O
PD498FINALMODEL:ASN 245:N,CA,C,O,CB,CG,OD1,ND2
PD498FINALMODEL:GLY 262:N,CA,C,O
PD498FINALMODEL:GLY 264:N,CA,C,O
PD498FINALMODEL:THR 265:N,CA,C,O,CB,OG1,CG2
```

Subset SUB5B:
sub5bmole.list

Subset SUB5B:
  PD498FINALMODEL:6–9,12–13,3–1–32,51–53, 56,81, 93–94,97–99,122,126–128,
  PD498FINALMODEL:131,155–157,159,197–199,209, 211,219–220,232,235,
  PD498FINALMODEL:237–239,241–242,244,246–249, 253,260–261,263,266–268
  sub5batom.list
Subset SUB5B:
  PD498FINALMODEL:PRO 6:N,CA,CD,C,O,CB,CG
  PD498FINALMODEL:TYR 7:N,CA,C,O,CB,CG,CD1, CD2,CE1,CE2,CZ,OH
  PD498FINALMODEL:TYR 8:N,CA,C,O,CB,CG,CD1, CD2,CE1,CE2,CZ,OH
  PD498FINALMODEL:SER 9:N,CA,C,O,CB,OG
  PD498FINALMODEL:GLN 12:N,CA,C,O,CB,CG,CD, OE1,NE2
  PD498FINALMODEL:TYR 13:N,CA,C,O,CB,CG,CD1, CD2,CE1,CE2,CZ,OH
  PD498FINALMODEL:SER 31:N,CA,C,O,CB,OG
  PD498FINALMODEL:THR 32:N,CA,C,O,CB,OG1, CG2
  PD498FINALMODEL:ARG 51:N,CA,C,O,CB,CG,CD, NE,CZ,NH1,NH2
  PD498FINALMODEL:LYS 52:N,CA,C,O,CB,CG,CD, CE,NZ
  PD498FINALMODEL:VAL 53:N,CA,C,O,CB,CG1, CG2
  PD498FINALMODEL:GLY 56:N,CA,C,O
  PD498FINALMODEL:ALA 81:N,CA,C,O,CB
  PD498FINALMODEL:MET 93:N,CA,C,O,CB,CG,SD, CE
  PD498FINALMODEL:ALA 94:N,CA,C,O,CB
  PD498FINALMODEL:THR 97:N,CA,C,O,CB,OG1, CG2
  PD498FINALMODEL:LYS 98:N,CA,C,O,CB,CG,CD, CE,NZ
  PD498FINALMODEL:ILE 99:N,CA,C,O,CB,CG1,CG2, CD1
  PD498FINALMODEL:TYR 122:N,CA,C,O,CB,CG, CD1,CD2,CE1,CE2,CZ,OH
  PD498FINALMODEL:GLN 126:N,CA,C,O,CB,CG,CD, OE1,NE2
  PD498FINALMODEL:GLY 127:N,CA,C,O
  PD498FINALMODEL:ALA 128:N,CA,C,O,CB
  PD498FINALMODEL:LEU 131:N,CA,C,O,CB,CG, CD1,CD2
  PD498FINALMODEL:GLY 155:N,CA,C,O
  PD498FINALMODEL:ALA 156:N,CA,C,O,CB
  PD498FINALMODEL:VAL 157:N,CA,C,O,CB,CG1, CG2
  PD498FINALMODEL:VAL 159:N,CA,C,O,CB,CG1, CG2
  PD498FINALMODEL:TYR 197:N,CA,C,O,CB,CG, CD1,CD2,CE1,CE2,CZ,OH
  PD498FINALMODEL:GLY 198:N,CA,C,O
  PD498FINALMODEL:THR 199:N,CA,C,O,CB,OG1, CG2
  PD498FINALMODEL:ASN 209:N,CA,C,O,CB,CG, OD1,ND2
  PD498FINALMODEL:ALA 211:N,CA,C,O,CB
  PD498FINALMODEL:TYR 219:N,CA,C,O,CB,CG, CD1,CD2,CE1,CE2,CZ,OH
  PD498FINALMODEL:SER 220:N,CA,C,O,CB,OG
  PD498FINALMODEL:VAL 232:N,CA,C,O,CB,CG1, CG2
  PD498FINALMODEL:LEU 235:N,CA,C,O,CB,CG, CD1,CD2
  PD498FINALMODEL:ALA 237:N,CA,C,O,CB
  PD498FINALMODEL:LEU 238:N,CA,C,O,CB,CG, CD1,CD2
  PD498FINALMODEL:LEU 239:N,CA,C,O,CB,CG, CD1,CD2
  PD498FINALMODEL:SER 241:N,CA,C,O,CB,OG
  PD498FINALMODEL:GLN 242:N,CA,C,O,CB,CG,CD, OE1,NE2
  PD498FINALMODEL:LYS 244:N,CA,C,O,CB,CG,CD, CE,NZ
  PD498FINALMODEL:ASN 246:N,CA,C,O,CB,CG, OD1,ND2
  PD498FINALMODEL:VAL 247:N,CA,C,O,CB,CG1, CG2
  PD498FINALMODEL:GLN 248:N,CA,C,O,CB,CG,CD, OE1,NE2
  PD498FINALMODEL:ILE 249:N,CA,C,O,CB,CG1, CG2,CD1
  PD498FINALMODEL:ILE 253:N,CA,C,O,CB,CG1, CG2,CD1
  PD498FINALMODEL:ILE 260:N,CA,C,O,CB,CG1, CG2,CD1
  PD498FINALMODEL:SER 261:N,CA,C,O,CB,OG
  PD498FINALMODEL:THR 263:N,CA,C,O,CB,OG1, CG2
  PD498FINALMODEL:ASN 266:N,CA,C,O,CB,CG, OD1,ND2
  PD498FINALMODEL:PHE 267:N,CA,C,O,CB,CG, CD1,CD2,CE1,CE2,CZ
  PD498FINALMODEL:LYS 268:N,CA,C,O,CB,CG,CD, CE,NZ
Subset ACTSITE:
  actsitemole.list
Subset ACTSITE:
  PD498FINALMODEL:36–42,57–60,66–80,100–110, 115–116,119,132–136,160–164,
  PD498FINALMODEL:182–184,194,206–207,210, 212–215,222–231
  actsiteatom.list
Subset ACTSITE:
  PD498FINALMODEL:ALA 36:N,CA,C,O,CB
  PD498FINALMODEL:VAL 37:N,CA,C,O,CB,CG1, CG2
  PD498FINALMODEL:LEU 38:N,CA,C,O,CB,CG,CD1, CD2
  PD498FINALMODEL:ASP 39:N,CA,C,O,CB,CG,OD1, OD2
  PD498FINALMODEL:SER 40:N,CA,C,O,CB,OG
  PD498FINALMODEL:GLY 41:N,CA,C,O
  PD498FINALMODEL:VAL 42:N,CA,C,O,CB,CG1, CG2
  PD498FINALMODEL:TYR 57:N,CA,C,O,CB,CG,CD1,CD2,CE1,CE2,CZ,OH
  PD498FINALMODEL:ASP 58:N,CA,C,O,CB,CG,OD1, OD2

PD498FINALMODEL:PHE 59:N,CA,C,O,CB,CG,CD1,CD2,CE1,CE2,CZ
PD498FINALMODEL:ILE 60:N,CA,C,O,CB,CG1,CG2,CD1
PD498FINALMODEL:PRO 66:N,CA,CD,C,O,CB,CG
PD498FINALMODEL:MET 67:N,CA,C,O,CB,CG,SD,CE
PD498FINALMODEL:ASP 68:N,CA,C,O,CB,CG,OD1,OD2
PD498FINALMODEL:LEU 69:N,CA,C,O,CB,CG,CD1,CD2
PD498FINALMODEL:ASN 70:N,CA,C,O,CB,CG,OD1,ND2
PD498FINALMODEL:GLY 71:N,CA,C,O
PD498FINALMODEL:HIS 72:N,CA,C,O,CB,CG,ND1,CD2,CE1,NE2
PD498FINALMODEL:GLY 73:N,CA,C,O
PD498FINALMODEL:THR 74:N,CA,C,O,CB,OG1,CG2
PD498FINALMODEL:HIS 75:N,CA,C,O,CB,CG,ND1,CD2,CE1,NE2
PD498FINALMODEL:VAL 76:N,CA,C,O,CB,CG1,CG2
PD498FINALMODEL:ALA 77:N,CA,C,O,CB
PD498FINALMODEL:GLY 78:N,CA,C,O
PD498FINALMODEL:THR 79:N,CA,C,O,CB,OG1,CG2
PD498FINALMODEL:VAL 80:N,CA,C,O,CB,CG1,CG2
PD498FINALMODEL:LEU 100:N,CA,C,O,CB,CG,CD1,CD2
PD498FINALMODEL:ALA 101:N,CA,C,O,CB
PD498FINALMODEL:VAL 102:N,CA,C,O,CB,CG1,CG2
PD498FINALMODEL:ARG 103:N,CA,C,O,CB,CG,CD,NE,CZ,NH1,NH2
PD498FINALMODEL:VAL 104:N,CA,C,O,CB,CG1,CG2
PD498FINALMODEL:LEU 105:N,CA,C,O,CB,CG,CD1,CD2
PD498FINALMODEL:ASP 106:N,CA,C,O,CB,CG,OD1,OD2
PD498FINALMODEL:ALA 107:N,CA,C,O,CB
PD498FINALMODEL:ASN 108:N,CA,C,O,CB,CG,OD1,ND2
PD498FINALMODEL:GLY 109:N,CA,C,O
PD498FINALMODEL:SER 110:N,CA,C,O,CB,OG
PD498FINALMODEL:SER 115:N,CA,C,O,CB,OG
PD498FINALMODEL:ILE 116:N,CA,C,O,CB,CG1,CG2,CD1
PD498FINALMODEL:GLY 119:N,CA,C,O
PD498FINALMODEL:ASN 132:N,CA,C,O,CB,CG,OD1,ND2
PD498FINALMODEL:LEU 133:N,CA,C,O,CB,CG,CD1,CD2
PD498FINALMODEL:SER 134:N,CA,C,O,CB,OG
PD498FINALMODEL:LEU 135:N,CA,C,O,CB,CG,CD1,CD2
PD498FINALMODEL:GLY 136:N,CA,C,O
PD498FINALMODEL:ALA 160:N,CA,C,O,CB
PD498FINALMODEL:ALA 161:N,CA,C,O,CB
PD498FINALMODEL:ALA 162:N,CA,C,O,CB
PD498FINALMODEL:GLY 163:N,CA,C,O
PD498FINALMODEL:ASN 164:N,CA,C,O,CB,CG,OD1,ND2
PD498FINALMODEL:VAL 182:N,CA,C,O,CB,CG1,CG2
PD498FINALMODEL:GLY 183:N,CA,C,O
PD498FINALMODEL:ALA 184:N,CA,C,O,CB
PD498FINALMODEL:PHE 194:N,CA,C,O,CB,CG,CD1,CD2,CE1,CE2,CZ
PD498FINALMODEL:PRO 206:N,CA,CD,C,O,CB,CG
PD498FINALMODEL:GLY 207:N,CA,C,O
PD498FINALMODEL:ILE 210:N,CA,C,O,CB,CG1,CG2,CD1
PD498FINALMODEL:SER 212:N,CA,C,O,CB,OG
PD498FINALMODEL:THR 213:N,CA,C,O,CB,OG1,CG2
PD498FINALMODEL:VAL 214:N,CA,C,O,CB,CG1,CG2
PD498FINALMODEL:PRO 215:N,CA,CD,C,O,CB,CG
PD498FINALMODEL:MET 222:N,CA,C,O,CB,CG,SD,CE
PD498FINALMODEL:SER 223:N,CA,C,O,CB,OG
PD498FINALMODEL:GLY 224:N,CA,C,O
PD498FINALMODEL:THR 225:N,CA,C,O,CB,OG1,CG2
PD498FINALMODEL:SER 226:N,CA,C,O,CB,OG
PD498FINALMODEL:MET 227:N,CA,C,O,CB,CG,SD,CE
PD498FINALMODEL:ALA 228:N,CA,C,O,CB
PD498FINALMODEL:SER 229:N,CA,C,O,CB,OG
PD498FINALMODEL:PRO 230:N,CA,CD,C,O,CB,CG
PD498FINALMODEL:HIS 231:N,CA,C,O,CB,CG,ND1,CD2,CE1,NE2
Subset RESTx:
　restxmole.list
Subset RESTX:
　NEWMODEL:233–234
　restxatom.list
Subset RESTX:
　NEWMODEL:ALA 233:N,CA,C,O,CB
　NEWMODEL:GLY 234:N,CA,C,O Example 4

Suitable Substitutions in the *Arthromyces Ramosus* Peroxidase for Addition of Carboxylic Acid Attachment Groups (—COOH)

Suitable locations for addition of carboxylic attachment groups (Aspartatic acids and Glutamic acids) in a non-hydrolytic enzyme, *Arthromyces ramosus* peroxidase were found as follows.

The 3D structure of this oxido-reductase is available in the Brookhaven Databank as 1arp.pdb. This *A. ramosus* peroxidase contains 344 amino acid residues. The first eight residues are not visible in the X-ray structure: QGPGGGGG, and N143 is glycosylated. The procedure described in Example 1 was followed.

The amino acid sequence of *Arthromyces ramosus* Peroxidase (E.C.1.11.1.7) is shown in SEQ ID NO 4.

The commands performed in Insight (BIOSYM) are shown in the command files makeDEzone.bcl and makeDEzone2.bcl below. The C-terminal residue is P344, the ACTSITE is defined as the heme group and the two histidines coordinating it (H56 & H184).

Conservative Substitutions:

makeDEzone.bcl

Delete Subset *

Color Molecule Atoms * Specified Specification 255,0, 255

Zone Subset ASP :asp:od* Static monomer/residue 10 Color_Subset 255,255,0

Zone Subset GLU :glu:oe* Static monomer/residue 10 Color_Subset 255,255,0

NOTE: editnextline C-terminal residue number according to the 40 protein

Zone Subset CTERM :344:0 Static monomer/residue 10 Color_Subset 255,255,0

NOTE: editnextline ACTSITE residues according to the protein

Zone Subset ACTSITE :HEM,56,184 Static monomer/residue 8

Color_Subset 255,255,0

Combine Subset ALLZONE Union ASP GLU

Combine Subset ALLZONE Union ALLZONE CTERM

Combine Subset ALLZONE Union ALLZONE ACTSITE

NOTE: editnextline object name according to the protein

Combine Subset REST Difference ARP ALLZONE

List Subset REST Atom Output_File restatom. list

List Subset REST monomer/residue Output_File restmole.list

Color Molecule Atoms ACTSITE Specified Specification 255,0,0

List Subset ACTSITE Atom Output_File actsiteatom.list

List Subset ACTSITE monomer/residue output File actsitemole.list

Zone Subset REST5A REST Static Monomer/Residue 5- Color_Subset

Combine Subset SUB5A Difference REST5A ACTSITE

Combine Subset SUB5B Difference SUB5A REST

Color Molecule Atoms SUB5B Specified Specification 255,255,255

List Subset SUB5B Atom Output_File sub5batom.list

List Subset SUB5B monomer/residue Output_File sub5bmole.list

Now identify sites for asn→asp & gln→glu substitutions and . . .

continue with makezone2.bcl.

Use grep command to identify asn/gln in restatom.list sub5batom.list & accsiteatom.list

Comments:

The subset REST contains Gln70, and SUB5B contains Gln34, Asn128, Asn303 all of which are solvent exposed. The substitutions Q34E or Q34D, Q70E or Q70D, N128D or N128E and N303D or N303E are identified in *A. ramosus* peroxidase as sites for mutagenesis. Residues are substituted below and further analysis done:

Non-conservative Substitutions:

makeDEzone2.bcl sourcefile makezone2.bcl Claus von der Osten 961128

having scanned lists (grep gln/asn command) and identified sites for . . .

asn→asp & gln→glu substitutions

NOTE: editnextline object name according to protein

Copy Object -To_Clipboard -Displace ARP newmodel Biopolymer

NOTE: editnextline object name according to protein Blank Object On ARP

NOTE: editnextlines with asn→asp & gln→glu positions

Replace Residue newmodel:34 glu L

Replace Residue newmodel:70 glu L

Replace Residue newmodel:128 asp L

Replace Residue newmodel:303 asp L

Now repeat analysis done prior to asn→asp & gln→glu, . . .

now including introduced asp & glu

Color Molecule Atoms newmodel Specified Specification 255,0,255

Zone Subset ASPx newmodel:asp:od* Static monomer/residue 10

Color_Subset 255,255,0

Zone Subset GLUx newmodel:glu:oe* Static monomer/residue 10

Color_Subset 255,255,0

NOTE: editnextline C-terminal residue number according to the protein

Zone Subset CTERMX newmodel:344:0 Static monomer/residue 10

Color_Subset 255,255,0

NOTE: editnextline ACTSITEx residues according to the protein

Zone Subset ACTSITEx newmodel:HEM,56,184 Static monomer/residue

8 Color_Subset 255,255,0

Combine Subset ALLZONEx Union ASPx GLUx

Combine Subset ALLZONEx Union ALLZONEx CTERMx

Combine Subset ALLZONEx Union ALLZONEx ACTSITEx

Combine Subset RESTX Difference newmodel ALLZONEx

List Subset RESTx Atom Output_File restxatom.list

List Subset RESTX monomer/residue Output_File restxmole.list

Color Molecule Atoms ACTSITEx Specified Specification 255,0,0

List Subset ACTSITEx Atom Output_File actsitexatom.list

List Subset ACTSITEx monomer/residue Output_File actsitexmole.list

read restxatom.list or restxmole.list to identify sites for (not_gluasp)→gluasp . . .

subst. if needed

Comments:

The subset RESTX contains only four residues: S9, S334, G335 and P336, all of which are >5% solvent exposed. The mutations S9D, S9E, S334D, S334E, G335D, G335E, P336D and P336E are proposed in *A. ramosus* peroxidase. Acidic residues within the subset ACTSITE are: E44, D57, D77, E87, E176, D179, E190, D202, D209, D246 and the N-terminal carboxylic acid on P344. Of these only E44, D77, E176, D179, E190, D209, D246 and the N-terminal carboxylic acid on P344 are solvent exposed. Suitable sites for mutations are E44Q, D77N, E176Q, D179N, E190Q, D209N and D246N. D246N and D246E are risky mutations due to D246's importance for binding of heme.

The N-terminal 8 residues were not included in the calculations above, as they do not appear in the structure. None of these 8 residues, QGPGGGG, contain carboxylic groups. The following variants are proposed as possible mutations to enable attachment to this region: Q1E, Q1, G2E, G2D, P3E, P3D, G4E, G4D, G5E, G5D, G6E, G6D, G7E, G7D, G8E, G8D.

Relevant Data for Example 4:

Solvent accessibility data for *A. ramosus* peroxidase (Note: as the first eight residues are missing in the X-ray structure, the residue numbers printed in the accessibility list below are 8 lower than those used elsewhere for residue numbering.

| # ARP | Thu Jan 30 15:39:05 MET |
|---|---|
| # residue | area |
| SER_1 | 143.698257 |
| VAL_2 | 54.879990 |
| THR_3 | 86.932701 |
| CYS_4 | 8.303715 |
| PRO_5 | 126.854782 |
| GLY_6 | 53.771488 |
| GLY_7 | 48.137802 |
| GLN_8 | 62.288475 |
| SER_9 | 79.932549 |
| THR_10 | 16.299215 |
| SER_11 | 81.928642 |
| ASN_12 | 51.432678 |
| SER_13 | 81.993019 |
| GLN_14 | 92.344009 |
| CYS_15 | 0.000000 |
| CYS_16 | 32.317432 |
| VAL_17 | 54.067810 |
| TRP_18 | 6.451035 |
| PHE_19 | 25.852070 |
| ASP_20 | 79.033997 |
| VAL_21 | 0.268693 |
| LEU_22 | 22.032858 |
| ASP_23 | 90.111404 |
| ASP_24 | 43.99324G |
| LEU_25 | 1.074774 |
| GLN_26 | 25.589321 |
| THR_27 | 82.698059 |
| ASN_28 | 96.600883 |
| PHE_29 | 32.375275 |
| TYR_30 | 5.898365 |
| GLN_31 | 103.380585 |
| GLY_32 | 40.042034 |
| SER_33 | 46.789322 |
| LYS_34 | 87.161873 |
| CYS_35 | 12.827215 |
| GLU_36 | 51.582657 |
| SER_37 | 16.378180 |
| PRO_38 | 33.560043 |
| VAL_39 | 6.448641 |
| ARG_40 | 7.068311 |
| LYS_41 | 15.291286 |
| ILE_42 | 1.612160 |

-continued

| # ARP | Thu Jan 30 15:39:05 MET |
|---|---|
| # residue | area |
| LEU_43 | 1.880854 |
| ARG_44 | 16.906845 |
| ILE_45 | 0.000000 |
| VAL_46 | 2.312647 |
| PHE_47 | 2.955627 |
| HIS_48 | 20.392527 |
| ASP_49 | 4.238116 |
| ALA_50 | 0.510757 |
| ILE_51 | 1.576962 |
| GLY_52 | 2.858601 |
| PHE_53 | 48.633503 |
| SER_54 | 8.973248 |
| PRO_55 | 58.822315 |
| ALA_56 | 59.782852 |
| LEU_57 | 46.483955 |
| THR_58 | 86.744827 |
| ALA_59 | 89.515816 |
| ALA_60 | 81.163239 |
| GLY_61 | 70.119019 |
| GLN_62 | 112.635498 |
| PHE_63 | 93.522354 |
| GLY_64 | 2.742587 |
| GLY_65 | 13.379636 |
| GLY_66 | 22.722847 |
| GLY_67 | 0.000000 |
| ALA_68 | 0.268693 |
| ASP_69 | 12.074840 |
| GLY_70 | 0.700486 |
| SER_71 | 0.000000 |
| ILE_72 | 0.000000 |
| ILE_73 | 0.000000 |
| ALA_74 | 17.304443 |
| HIS_75 | 41.071186 |
| SER_76 | 20.000793 |
| ASN_77 | 120.855316 |
| ILE_78 | 66.574982 |
| GLU_79 | 2.334954 |
| LEU_80 | 41.329689 |
| ALA_81 | 77.370575 |
| PHE_82 | 38.758759 |
| PRO_83 | 131.946289 |
| ALA_84 | 34.893864 |
| ASN_85 | 5.457000 |
| GLY_86 | 43.364151 |
| GLY_87 | 51.561348 |
| LEU_88 | 0.242063 |
| THR_89 | 73.343575 |
| ASP_90 | 130.139389 |
| THR_91 | 17.863211 |
| ILE_92 | 0.268693 |
| GLU_93 | 92.210396 |
| ALA_94 | 35.445068 |
| LEU_95 | 1.343467 |
| ARG_96 | 31.175611 |
| ALA_97 | 44.650192 |
| VAL_98 | 17.698566 |
| GLY_99 | 1.471369 |
| ILE_100 | 62.441463 |
| ASN_101 | 107.139748 |
| HIS_102 | 46.952496 |
| GLY_103 | 46.559296 |
| VAL_104 | 11.342628 |
| SER_105 | 15.225677 |
| PHE_106 | 6.422011 |
| GLY_107 | 3.426864 |
| ASP_108 | 10.740790 |
| LEU_109 | 0.268693 |
| ILE_110 | 1.880854 |
| GLN_111 | 31.867456 |
| PHE_112 | 0.000000 |
| ALA_113 | 0.000000 |
| THR_114 | 3.656114 |
| ALA_115 | 8.299393 |
| VAL_116 | 0.268693 |
| GLY_117 | 0.268693 |

-continued

ARP   Thu Jan 30 15:39:05 MET

| # residue | area |
|---|---|
| MET_118 | 3.761708 |
| SER_119 | 14.536770 |
| ASN_120 | 25.928799 |
| CYS_121 | 0.537387 |
| PRO_122 | 29.798336 |
| GLY_123 | 33.080013 |
| SER_124 | 17.115562 |
| PRO_125 | 36.908714 |
| ARG_126 | 108.274727 |
| LEU_127 | 21.238588 |
| GLU_128 | 53.742313 |
| PHE_129 | 3.761708 |
| LEU_130 | 12.928699 |
| THR_131 | 10.414591 |
| GLY_132 | 47.266495 |
| ARG_133 | 12.247048 |
| SER_134 | 63.047237 |
| ASN_135 | 31.403708 |
| SER_136 | 97.999619 |
| SER_137 | 28.505201 |
| GLN_138 | 102.845520 |
| PRO_139 | 49.691917 |
| SER_140 | 9.423104 |
| PRO_141 | 25.724171 |
| PRO_142 | 80.706665 |
| SER_143 | 105.318176 |
| LEU_144 | 20.154398 |
| ILE_145 | 41.288322 |
| PRO_146 | 10.462679 |
| GLY_147 | 19.803421 |
| PRO_148 | 18.130360 |
| GLY_149 | 47.391853 |
| ASN_150 | 60.248917 |
| THR_151 | 87.887985 |
| VAL_152 | 13.870322 |
| THR_153 | 74.664734 |
| ALA_154 | 45.251106 |
| ILE_155 | 2.686934 |
| LEU_156 | 28.720940 |
| ASP_157 | 110.081253 |
| ARG_158 | 31.228874 |
| MET_159 | 1.612160 |
| GLY_160 | 38.223858 |
| ASP_161 | 46.293152 |
| ALA_162 | 9.877204 |
| GLY_163 | 34.267326 |
| PHE_164 | 11.057570 |
| SER_165 | 51.158882 |
| PRO_166 | 62.767738 |
| ASP_167 | 75.164917 |
| GLU_168 | 43.334976 |
| VAL_169 | 6.365355 |
| VAL_170 | 2.955627 |
| ASP_171 | 7.004863 |
| LEU_172 | 1.880854 |
| LEU_173 | 3.197691 |
| ALA_174 | 0.000000 |
| ALA_175 | 1.074774 |
| HIS_176 | 0.502189 |
| SER_177 | 0.806080 |
| LEU_178 | 3.197691 |
| ALA_179 | 3.337480 |
| SER_180 | 0.466991 |
| GLN_181 | 2.122917 |
| GLU_182 | 40.996552 |
| GLY_183 | 62.098671 |
| LEU_184 | 23.954853 |
| ASN_185 | 15.918136 |
| SER_186 | 95.185318 |
| ALA_187 | 59.075272 |
| ILE_188 | 27.675419 |
| PHE_189 | 102.799423 |
| ARG_190 | 55.265549 |
| SER_191 | 6.986028 |
| PRO_192 | 2.686934 |

-continued

ARP   Thu Jan 30 15:39:05 MET

| # residue | area |
|---|---|
| LEU_193 | 12.321225 |
| ASP_194 | 2.127163 |
| SER_195 | 33.556419 |
| THR_196 | 33.049286 |
| PRO_197 | 20.874798 |
| GLN_198 | 65.729698 |
| VAL_199 | 31.705818 |
| PHE_200 | 4.753195 |
| ASP_201 | 13.744506 |
| THR_202 | 1.612160 |
| GLN_203 | 16.081930 |
| PHE_204 | 2.581340 |
| TYR_205 | 1.880854 |
| ILE_206 | 9.356181 |
| GLU_207 | 0.735684 |
| THR_208 | 10.685907 |
| LEU_209 | 9.672962 |
| LEU_210 | 2.955627 |
| LYS_211 | 77.176834 |
| GLY_212 | 40.968609 |
| THR_213 | 78.718216 |
| THR_214 | 21.738384 |
| GLN_215 | 77.622299 |
| PRO_216 | 25.441587 |
| GLY_217 | 8.320850 |
| PRO_218 | 96.972305 |
| SER_219 | 64.627823 |
| LEU_220 | 85.732414 |
| GLY_221 | 27.361111 |
| PHE_222 | 134.620178 |
| ALA_223 | 3.873014 |
| GLU_224 | 12.141763 |
| GLU_225 | 65.129868 |
| LEU_226 | 76.105843 |
| SER_227 | 0.268693 |
| PRO_228 | 7.017754 |
| PHE_229 | 0.000000 |
| PRO_230 | 47.827423 |
| GLY_231 | 23.790522 |
| GLU_232 | 6.643466 |
| PHE_233 | 6.713862 |
| ARG_234 | 18.012030 |
| MET_235 | 4.598188 |
| ARG_236 | 91.415581 |
| SER_237 | 1.982125 |
| ASP_238 | 6.246871 |
| ALA_239 | 12.897283 |
| LEU_240 | 76.820526 |
| LEU_241 | 3.224321 |
| ALA_242 | 1.400973 |
| ARG_243 | 77.207176 |
| ASP_244 | 36.207306 |
| SER_245 | 104.023796 |
| ARG_246 | 121.852341 |
| THR_247 | 2.955627 |
| ALA_248 | 4.810700 |
| CYS_249 | 47.331306 |
| ARG_250 | 62.062778 |
| TRP_251 | 2.418241 |
| GLN_252 | 5.554953 |
| SER_253 | 38.284832 |
| MET_254 | 1.124224 |
| THR_255 | 0.000000 |
| SER_256 | 53.758987 |
| SER_257 | 37.276134 |
| ASN_258 | 44.381340 |
| GLU_259 | 149.565140 |
| VAL_260 | 57.500389 |
| MET_261 | 2.679314 |
| GLY_262 | 10.175152 |
| GLN_263 | 107.458916 |
| ARG_264 | 36.402130 |
| TYR_265 | 0.233495 |
| ARG_266 | 91.179619 |
| ALA_267 | 53.708500 |

-continued

| # ARP | Thu Jan 30 15:39:05 MET |
|---|---|
| # residue | area |
| ALA__268 | 6.504294 |
| MET__269 | 17.122011 |
| ALA__270 | 22.455158 |
| LYS__271 | 73.386177 |
| MET__272 | 3.959508 |
| SER__273 | 15.043281 |
| VAL__274 | 23.887930 |
| LEU__275 | 17.196379 |
| GLY__276 | 44.362202 |
| PHE__277 | 68.062485 |
| ASP__278 | 94.902039 |
| ARG__279 | 113.549011 |
| ASN__280 | 134.886017 |
| ALA__281 | 72.340973 |
| LEU__282 | 26.692348 |
| THR__283 | 27.696728 |
| ASP__284 | 72.214157 |
| CYS__285 | 0.000000 |
| SER__286 | 28.209335 |
| ASP__287 | 64.560753 |
| VAL__288 | 7.040061 |
| ILE__289 | 8.665112 |
| PRO__290 | 48.682365 |
| SER__291 | 86.141670 |
| ALA__292 | 29.031240 |
| VAL__293 | 84.432014 |
| SER__294 | 85.944153 |
| ASN__295 | 49.017288 |
| ASN__296 | 133.459198 |
| ALA__297 | 57.283794 |
| ALA__298 | 65.233749 |
| PRO__299 | 24.751518 |
| VAL__300 | 45.409184 |
| ILE__301 | 8.060802 |
| PRO__302 | 14.742939 |
| GLY__303 | 16.589832 |
| GLY__304 | 34.238071 |
| LEU__305 | 24.719791 |
| THR__306 | 49.356300 |
| VAL__307 | 71.491821 |
| ASP__308 | 130.906174 |
| ASP__309 | 31.733070 |
| ILE__310 | 19.581894 |
| GLU__311 | 81.414574 |
| VAL__312 | 94.769890 |
| SER__313 | 39.688896 |
| CYS__314 | 9.998511 |
| PRO__315 | 120.328018 |
| SER__316 | 95.364319 |
| GLU__317 | 65.560959 |
| PRO__318 | 100.254364 |
| PHE__319 | 46.284115 |
| PRO__320 | 31.328060 |
| GLU__321 | 177.602249 |
| ILE__322 | 33.449741 |
| ALA__323 | 46.892982 |
| THR__324 | 79.976471 |
| ALA__325 | 36.423820 |
| SER__326 | 124.467422 |
| GLY__327 | 28.219524 |
| PRO__328 | 107.553696 |
| LEU__329 | 86.789825 |
| PRO__330 | 34.287163 |
| SER__331 | 75.764053 |
| LEU__332 | 32.840569 |
| ALA__333 | 61.516434 |
| PRO__334 | 82.389992 |
| ALA__335 | 6.246871 |
| PRO__336 | 56.750813 |
| HEM__337 | 60.435017 |
| CA__338 | 2.078997 |
| CA__339 | 0.000000 |
| NAG__340 | 141.534668 |
| NAG__341 | 186.311371 |

Subset REST:
  restmole.list
Subset REST:
  ARP:9,69–70,125,127,133,299–301,334–336
  restatom.list
Subset REST:
  ARP:SER 9:N,CA,C,O,CB,OG
  ARP:GLY 69:N,CA,C,O
  ARP:GLN 70:N,CA,C,O,CB,CG,CD,OE1,NE2
  ARP:GLY 125:N,CA,C,O
  ARP:SER 127:N,CA,C,O,CB,OG
  ARP:PRO 133:N,CA,CD,C,O,CB,CG
  ARP:SER 299:N,CA,C,O,CB,OG
  ARP:ALA 300:N,CA,C,O,CB
  ARP:VAL 301:N,CA,C,O,CB,CG1,CG2
  ARP:SER 334:N,CA,C,O,CB,OG
  ARP:GLY 335:N,CA,C,O
  ARP:PRO 336:N,CA,CD,C,O,CB,CG
Subset SUB5B:
  sub5bmole.list
Subset SUB5B:
  ARP:10–11,34,38,65–68,71–72,120–121,123–124,
    128–132,134,270,274,
  ARP:297–298,302–303,311–312,332–333,337–338
  sub5batom.list
Subset SUB5B:
  ARP:VAL 10:N,CA,C,O,CB,CG1,CG2
  ARP:THR 11:N,CA,C,O,CB,OG1,CG2
  ARP:GLN 34:N,CA,C,O,CB,CG,CD,OE1,NE2
  ARP:TYR 38:N,CA,C,O,CB,CG,CD1,CD2,CE1,CE2,
    CZ,OH
  ARP:LEU 65:N,CA,C,O,CB,CG,CD1,CD2
  ARP:THR 66:N,CA,C,O,CB,OG1,CG2
  ARP:ALA 67:N,CA,C,O,CB
  ARP:ALA 68:N,CA,C,O,CB
  ARP:PHE 71:N,CA,C,O,CB,CG,CD1,CD2,CE1,CE2,CZ
  ARP:GLY 72:N,CA,C,O
  ARP:PHE 120:N,CA,C,O,CB,CG,CD1,CD2,CE1,CE2,
    CZ
  ARP:ALA 121:N,CA,C,O,CB
  ARP:ALA 123:N,CA,C,O,CB
  ARP:VAL 124:N,CA,C,O,CB,CG1,CG2
  ARP:ASN 128:N,CA,C,O,CB,CG,OD1,ND2
  ARP:CYS 129:N,CA,C,O,CB,SG
  ARP:PRO 130:N,CA,CD,C,O,CB,CG
  ARP:GLY 131:N,CA,C,O
  ARP:SER 132:N,CA,C,O,CB,OG
  ARP:ARG 134:N,CA,C,O,CB,CG,CD,NE,CZ,NH1,NH2
  ARP:GLY 270:N,CA,C,O
  ARP:ARG 274:N,CA,C,O,CB,CG,CD,NE,CZ,NH1,NH2
  ARP:ILE 297:N,CA,C,O,CB,CG1,CG2,CD1
  ARP:PRO 298:N,CA,CD,C,O,CB,CG
  ARP:SER 302:N,CA,C,O,CB,OG
  ARP:ASN 303:N,CA,C,O,CB,CG,OD1,ND2
  ARP:GLY 311:N,CA,C,O
  ARP:GLY 312:N,CA,C,O
  ARP:THR 332:N,CA,C,O,CB,OG1,CG2
  ARP:ALA 333:N,CA,C,O,CB ARP:LEU 337:N,CA,C,O,CB,CG,CD1,CD2
ARP:PRO 338:N,CA,CD,C,O,CB,CG
Subset ACTSITE:
actsitemole.list
Subset ACTSITE:
ARP:44–61,75–77,79–80,87–88,90–96,99,118,122,126,135,148–149,152–158,
ARP:163–164,167,176–194,197–205,207–209,211–213,216,230–231,241,
ARP:243–246,249,259,273,277,280,343–347H
actsiteatom.list
Subset ACTSITE:
ARP:GLU 44:N,CA,C,O,CB,CG,CD,OE1,OE2
ARP:SER 45:N,CA,C,O,CB,OG
ARP:PRO 46:N,CA,CD,C,O,CB,CG
ARP:VAL 47:N,CA,C,O,CB,CG1,CG2
ARP:ARG 48:N,CA,C,O,CB,CG,CD,NE,CZ,NH1,NH2
ARP:LYS 49:N,CA,C,O,CB,CG,CD,CE,NZ
ARP:ILE 50:N,CA,C,O,CB,CG1,CG2,CD1
ARP:LEU 51:N,CA,C,O,CB,CG,CD1,CD2
ARP:ARG 52:N,CA,C,O,CB,CG,CD,NE,CZ,NH1,NH2
ARP:ILE 53:N,CA,C,O,CB,CG1,CG2,CD1
ARP:VAL 54:N,CA,C,O,CB,CG1,CG2
ARP:PHE 55:N,CA,C,O,CB,CG,CD1,CD2,CE1,CE2,CZ
ARP:HIS 56:N,CA,C,O,CB,CG,ND1,CD2,CE1,NE2
ARP:ASP 57:N,CA,C,O,CB,CG,OD1,OD2
ARP:ALA 58:N,CA,C,O,CB
ARP:ILE 59:N,CA,C,O,CB,CG1,CG2,CD1
ARP:GLY 60:N,CA,C,O
ARP:PHE 61:N,CA,C,O,CB,CG,CD1,CD2,CE1,CE2,CZ
ARP:GLY 15:N,CA,C,O
ARP:ALA 76:N,CA,C,O,CB
ARP:ASP 77:N,CA,C,O,CB,CG,OD1,OD2
ARP:SER 79:N,CA,C,O,CB,OG
ARP:ILE 80:N,CA,C,O,CB,CG1,CG2,CD1
ARP:GLU 87:N,CA,C,O,CB,CG,CD,OE1,OE2
ARP:LEU 88:N,CA,C,O,CB,CG,CD1,CD2
ARP:PHE 90:N,CA,C,O,CB,CG,CD1,CD2,CE1,CE2,CZ
ARP:PRO 91:N,CA,CD,C,O,CB,CG
ARP:ALA 92:N,CA,C,O,CB
ARP:ASN 93:N,CA,C,O,CB,CG,OD1,ND2
ARP:GLY 94:N,CA,C,O
ARP:GLY 95:N,CA,C,O
ARP:LEU 96:N,CA,C,O,CB,CG,CD1,CD2
ARP:THR 99:N,CA,C,O,CB,OG1,CG2
ARP:ILE 118:N,CA,C,O,CB,CG1,CG2,CD1
ARP:THR 122:N,CA,C,O,CB,OG1,CG2
ARP:MET 126:N,CA,C,O,CB,CG,SD,CE
ARP:LEU 135:N,CA,C,O,CB,CG,CD1,CD2
ARP:SER 148:N,CA,C,O,CB,OG
ARP:PRO 149:N,CA,CD,C,O,CB,CG
ARP:LEU 152:N,CA,C,O,CB,CG,CD1,CD2
ARP:ILE 153:N,CA,C,O,CB,CG1,CG2,CD1
ARP:PRO 154:N,CA,CD,C,O,CB,CG
ARP:GLY 155:N,CA,C,O
ARP:PRO 156:N,CA,CD,C,O,CB,CG
ARP:GLY 157:N,CA,C,O
ARP:ASN 158:N,CA,C,O,CB,CG,OD1,ND2
ARP:ILE 163:N,CA,C,O,CB,CG1,CG2,CD1
ARP:LEU 164:N,CA,C,O,CB,CG,CD1,CD2
ARP:MET 167:N,CA,C,O,CB,CG,SD,CE
ARP:GLU 176:N,CA,C,O,CB,CG,CD,OE1,OE2
ARP:VAL 177:N,CA,C,O,CB,CG1,CG2
ARP:VAL 178:N,CA,C,O,CB,CG1,CG2
ARP:ASP 179:N,CA,C,O,CB,CG,OD1,OD2
ARP:LEU 180:N,CA,C,O,CB,CG,CD1,CD2
ARP:LEU 181:N,CA,C,O,CB,CG,CD1,CD2
ARP:ALA 182:N,CA,C,O,CB
ARP:ALA 183:N,CA,C,O,CB
ARP:HIS 184:N,CA,C,O,CB,CG,ND1,CD2,CE1,NE2
ARP:SER 185:N,CA,C,O,CB,OG
ARP:LEU 186:N,CA,C,O,CB,CG,CD1,CD2
ARP:ALA 187:N,CA,C,O,CB
ARP:SER 188:N,CA,C,O,CB,OG
ARP:GLN 189:N,CA,C,O,CB,CG,CD,OE1,NE2
ARP:GLU 190:N,CA,C,O,CB,CG,CD,OE1,OE2
ARP:GLY 191:N,CA,C,O
ARP:LEU 192:N,CA,C,O,CB,CG,CD1, CD2
ARP:ASN 193:N,CA,C,O,CB,CG,OD1,ND2
ARP:SER 194:N,CA,C,O,CB,OG
ARP:PHE 197:N,CA,C,O,CB,CG,CD1,CD2,CE1,CE2,CZ
ARP:ARG 198:N,CA,C,O,CB,CG,CD,NE,CZ,NH1,NH2
ARP:SER 199:N,CA,C,O,CB,OG
ARP:PRO 200:N,CA,CD,C,O,CB,CG
ARP:LEU 201:N,CA,C,O,CB,CG,CD1,CD2
ARP:ASP 202:N,CA,C,O,CB,CG,OD1,OD2
ARP:SER 203:N,CA,C,O,CB,OG
ARP:THR 204:N,CA,C,O,CB,OG1,CG2
ARP:PRO 205:N,CA,CD,C,O,CB,CG
ARP:VAL 207:N,CA,C,O,CB,CG1,CG2
ARP:PHE 208:N,CA,C,O,CB,CG,CD1,CD2,CE1,CE2,CZ
ARP:ASP 209:N,CA,C,O,CB,CG,OD1,OD2
ARP:GLN 211:N,CA,C,O,CB,CG,CD,OE1,NE2
ARP:PHE 212:N,CA,C,O,CB,CG,CD1,CD2,CE1,CE2,CZ
ARP:TYR 213:N,CA,C,O,CB,CG,CD1,CD2,CE1,CE2,CZ,OH
ARP:THR 216:N,CA,C,O,CB,OG1,CG2
ARP:PHE 230:N,CA,C,O,CB,CG,CD1,CD2,CE1,CE2,CZ
ARP:ALA 231:N,CA,C,O,CB
ARP:PHE241:N,CA,C,O,CB,CG,CD1,CD2,CE1,CE2,CZ
ARP:MET 243:N,CA,C,O,CB,CG,SD,CE
ARP:ARG 244:N,CA,C,O,CB,CG,CD,NE,CZ,NH1,NH2
ARP:SER 245:N,CA,C,O,CB,OG
ARP:ASP 246:N,CA,C,O,CB,CG,OD1,OD2
ARP:LEU 249:N,CA,C,O,CB,CG,CD1,CD2
ARP:TRP 259:N,CA,C,O,CB,CG,CD1, CD2,NE1,CE2,CE3,CZ2,CZ3,CH2
ARP:TYR 273:N,CA,C,O,CB,CG,CD1,CD2,CE1,CE2,CZ,OH
ARP:MET 277:N,CA,C,O,CB,CG,SD,CE ARP:MET 280:N,CA,C,O,CB,CG,SD,CE
ARP:ALA 343:N,CA,C,O,CB
ARP:PRO 344:N,CA,CD,C,O,OXT,CB,CG
ARP:HEM 345H:FE,NA,NB,NC,ND,CHA,CHB, CHC, CHD,C1A,C2A,C3A,C4A,CMA,CAA,CBA,CGA
ARP:HEM 345H:O1A,O2A,C1B,C2B,C3B,C4B,CMB, CAB,CBB,C1C,C2C,C3C,C4C,CMC,CAC,CBC
ARP:HEM 345H:C1D,C2D,C3D,C4D,CMD,CAD,CBD, CGD,O1D,O2D
ARP:CA 346H:CA
ARP:CA 347H:CA
Subset RESTx:
  restxmole.list
Subset RESTX
  NEWMODEL:9,334–336
  restxatom.list
Subset RESTX:
  NEWMODEL:SER 9:N,CA,C,O,CB,OG
  NEWMODEL:SER 334:N,CA,C,O,CB,OG
  NEWMODEL:GLY 335:N,CA,C,O
  NEWMODEL:PRO 336:N,CA,CD,C,O,CB,CG Example 5

Activation of mPEG 15,000 With N-succinimidyl Carbonate mPEG 15,000 was suspended in toluene (4 ml/g of mPEG) 20% was distilled off at normal pressure to dry the reactants azeotropically. Dichloromethane (dry 1 ml/g mPEG) was added when the solution was cooled to 30° C. and phosgene in toluene (1.93 M 5 mole/mole mPEG) was added and mixture stirred at room temperature overnight. The mixture was evaporated to dryness and the desired product was obtained as waxy lumps.

After evaporation dichloromethane and toluene (1:2, dry 3 ml/g mPEG) was added to re-dissolve the white solid. N-Hydroxy succinimide (2 mole/mole mPEG.) was added as a solid and then triethylamine (1.1 mole/mole mPEG). The mixture was stirred for 3 hours. initially unclear, then clear and ending with a small precipitate. The mixture was evaporated to dryness and recrystallized from ethyl acetate (10ml) with warm filtration to remove salts and insoluble traces. The blank liquid was left for slow cooling at ambient temperature for 16 hours and then in the refrigerator, overnight. The white precipitate was filtered and washed with a little cold ethyl acetate and dried to yield 98% (w/w). NMR Indicating 80–90% activation and 5 o/oo (w/w) HNEt$_3$Cl. $^1$H-NMR for mPEG 15,000 (CDCl$_3$) d 1.42 t (I=4.8 CH$_3$ i HNEt$_3$Cl), 2.84 s (I=3.7 succinimide), 3.10 dq (I=3.4 CH$_2$ i HNEt$_3$Cl), 3.38 s (I=2.7 CH$_3$ i OMe), 3.40* dd (I=4.5 o/oo, $^{13}$C satellite), 3.64 bs (I=1364 main peak), 3.89* dd (I=4.8 o/oo, $^{13}$C satellite), 4.47 dd (I=1.8, CH2 in PEG). No change was seen after storage in a desiccator at 22° C. for 4 months.

Example 6

Activation of mPEG 5,000 With N-succinimidyl Carbonate

Activation of mPEG 5,000 with N-succinimidyl carbonate was performed as described in Example 5.

Example 7

Construction and Expression of PD498 Variants:

PD498 site-directed variants were constructed using the "maxioligonucleotide-PCR" method described by Sarkar et al., (1990): BioTechniques 8: 404–407.

The template plasmid was shuttle vector pPD498 or an analogue of this containing a variant of the PD498 protease gene.

The following PD498 variants were constructed, expressed and purified.

A: R28K
B: R62K
C: R169K
D: R28K+R62K
E: R28K+R169K
F: R62K+R169K
G: R28K+R69K+R169K

Construction of Variants

For introduction of the R28K substitution a synthetic oligonucleotide having the sequence: GGG ATG TAA CCA AGG GAA GCA GCA CTC AAA CG (SEQ ID NO. 7) was used.

A PCR fragment of 769 bp was ligated into the pPD498 plasmid prepared by Bst E II and Bgl II digestion. Positive variants were recognized by StyI digestion and verified by DNA sequencing of the total 769 bp insert.

For introduction of the R62K substitution a synthetic oligonucleotide having the sequence: CGA CTT TAT CGA TAA GGA CAA TAA CCC (SEQ ID NO. 8) was used.

A PCR fragment of 769 bp was ligated into the pPD498 plasmid prepared by Bst E II and Bgl II digestion. Positive variants were recognized by ClaI digestion and verified by DNA sequencing of the total 769 bp insert.

For introduction of the R169K substitution a synthetic oligonucleotide having the sequence: CAA TGT ATC CAA AAC GTT CCA ACC AGC (SEQ ID NO. 9) was used.

A PCR fragment of 769 bp was ligated into the pPD498 plasmid prepared by.Bst E II and Bgl II digestion. Positive variants were recognized by the absence of a Rsa I restriction site and verified by DNA sequencing of the total 769 bp insert.

For simultaneous introduction of the R28K and the R62K substitutions, synthetic oligonucleotides having the sequence: GGG ATG TAA CCA AGG GAA GCA GCA CTC AAA CG (SEQ ID NO. 7) and the sequence: CGA CTT TAT CGA TAA GGA CAA TAA CCC (SEQ ID No. 8) were used simultaneous. A PCR fragment of 769 bp was ligated into the pPD498 plasmid prepared by Bst E II and Bgl II digestion. Positive variants were recognized by StyI and ClaI digestion and verified by DNA sequencing of the total 769 bp insert.

For simultaneous introduction of the R28K and the R169K substitutions, synthetic oligonucleotides having the sequence: GGG ATG TAA CCA AGG GAA GCA GCA CTC AAA CG (SEQ ID NO. 7) and the sequence: CAA TGT ATC CAA AAC GTT CCA ACC AGC (SEQ ID NO. 9) were used simultaneously. A PCR fragment of 769 bp was ligated into the pPD498 plasmid prepared by Bst E II and Bgl II digestion. Positive variants were recognized by StyI digestion and absence of a Rsa I site. The variant was verified by DNA sequencing of the total 769 bp insert.

For simultaneous introduction of the R62K and the R169K substitutions, synthetic oligonucleotides having the sequence: CGA CTT TAT CGA TAA GGA CAA TAA CCC (SEQ ID NO. 8) and the sequence: CAA TGT ATC CAA AAC GTT CCA ACC AGC (SEQ ID NO. 9) were used simultaneously. A PCR fragment of 769 bp was ligated into the pPD498 plasmid prepared by Bst E II and Bgl II digestion. Positive variants were recognized by ClaI digestion and absence of a Rsa I site. The variant was verified by DNA sequencing of the total 769 bp insert.

For simultaneous introduction of the R28K, the R62K and the 169K substitutions, synthetic oligonucleotides having the sequence: GGG ATG TAA CCA AGG GAA GCA GCA CTC AAA CG (SEQ ID No. 7) the sequence: CGA CTT TAT CGA TAA GGA CAA TAA CCC (SEQ ID NO. 8) and the sequence: CAA TGT ATC CAA AAC GTT CCA ACC AGC (SEQ ID NO. 9) were used simultaneously. A PCR fragment of 769 bp was ligated into the pPD498 plasmid prepared by Bst E II and Bgl II digestion. Positive variants were recognized by StyI and ClaI digestion and absence of a Rsa I site. The variant was verified by DNA sequencing of the total 769 bp insert.

Fermentation, Expression and Purification of PD498 Variants

Vectors hosting the above mentioned PD498 variants were purified from *E. coli* cultures and transformed into *B. subtilis* in which organism the variants were fermented, expressed and purified as described in the "Materials and Methods" section above.

Example 7

Conjugation of Triple Substituted PD498 Variant With Activated mPEG 5,000

200 mg of triple substituted PD498 variant (i.e. the R28K+R62K+R169K substituted variant) was incubated in 50 mm NaBorate, pH 10, with 1.8 g of activated mPEG 5,000 with N-succinimidyl carbonate (prepared according to Example 2), in a final volume of 20 ml. The reaction was carried out at ambient temperature using magnetic stirring. Reaction time was 1 hour. The reaction was stopped by adding DMG buffer to a final concentration of 5 mM dimethyl glutarate, 1 mM $CaCl_2$ and 50 mM borate, pH 5.0.

The molecule weight of the obtained derivative was approximately 120 kDa, corresponding to about 16 moles of mPEG attached per mole enzyme.

Compared to the parent enzyme, residual activity was close to 100% towards peptide substrate (succinyl-Ala-Ala-Pro-Phe-p-Nitroanilide).

Example 8

Allergenicity Trails of PD498 Variant-SPEG5.000 in Guinea Pigs

Dunkin Hartley guinea pigs are stimulated with 1.0 μg PD498-SPEG 5,000 and 1.0 μg modified variant PD498-SPEG 5,000 by intratracheal installation.

Sera from immunized Dunkin Hartley guinea pigs are tested during the trial period in a specific IgG, ELISA (described above) to elucidate whether the molecules could activate the immune response system giving rise to a specific $IgG_1$ response indicating an allergenic response.

The $IgG_1$ levels of Dunkin Hartley guinea pigs during the trail period of 10 weeks are observed.

Example 9

Suitable Substitutions in *Humicola lanuginosa* Lipase for Addition of Amino Attachment Groups (—$NH_2$)

The 3D structure of *Humicola lanuginosa* lipase (SEQ ID NO 6) is available in Brookhaven Databank as 1tib.pdb. The lipase consists of 269 amino acids.

The procedure described in Example 1 was followed. The sequence of *H. lanuginosa* lipase is shown below in the table listing solvent accessibility data for *H. lanuginosa* lipase. *H. lanuginosa* residue numbering is used (1–269), and the active site residues (functional site) are S146, S201 and H258. The synonym TIB is used for *H. lanuginosa* lipase.

The commands performed in Insight (BIOSYM) are shown in the command files makeKzone.bcl and makeKzone2.bcl below:

Conservative Substitutions:
makeKzone.bcl
 1 Delete Subset *
 2 Color Molecule Atoms * Specified Specification 255,0,255
 3 Zone Subset LYS :lys:NZ Static monomer/residue Color_Subset 255,255,0
 4 Zone Subset NTERM :1:N Static monomer/residue Color_Subset 255,255,0
 5 #NOTE: editnextline ACTSITE residues according to the protein
 6 Zone Subset ACTSITE :146,201,258 Static monomer/residue 8 Color_Subset 255,255,0
 7 Combine Subset ALLZONE Union LYS NTERM
 8 Combine Subset ALLZONE Union ALLZONE ACTSITE
 9 #NOTE: editnextline object name according to the protein
10 Combine Subset REST Difference TIB ALLZONE
11 List Subset REST Atom Output_File restatom.list
12 List Subset REST monomer/residue Output_File restmole.list
13 Color Molecule Atoms ACTSITE Specified Specification 255,0,0
14 List Subset ACTSITE Atom Output_File actsiteatom.list
15 List Subset ACTSITE monomer/residue.Output_File actsitemole.list
16 #
17 Zone Subset REST5A REST Static Monomer/Residue 5—Color_Subset
18 Combine Subset SUB5A Difference REST5A ACTSITE
19 Combine Subset SUB5B Difference SUB5A REST
20 Color Molecule Atoms SUB5B Specified Specification 255,255,255
21 List Subset SUB5B Atom Output_File sub5batom.list
22 List Subset SUB5B monomer/residue Output_File sub5bmole.list
23 #Now identify sites for lys→arg substitutions and continue with makezone2.bcl
24 #Use grep command to identify ARG in restatom.list, sub5batom.list & accsiteatom.list Comments:

In this case of *H. lanuginosa* (=TIB), REST contains the Arginines Arg133, Arg139, Arg160, Arg179 and Arg 209, and SUB5B contains Arg118 and R125.

These residues are all solvent exposed. The substitutions R133K, R139K, R160K, R179K, R209K, R118K and R125K are identified in TIB as sites for mutagenesis within the scope of this invention. The residues are substituted below in section 2, and further analysis done. The subset ACTSITE contains no lysines.

Non-conservative Substitutions:
makeKzone2.bcl
 1 #sourcefile makezone2.bcl Claus-von der Osten 961128
 2 #
 3 #having scanned lists (grep arg command) and identified sites for lys→arg substitutions
 4 #NOTE: editnextline object name according to protein
 5 Copy Object -To_Clipboard -Displace TIB newmodel
 6 Biopolymer
 7 #NOTE: editnextline object name according to protein
 8 Blank Object On TIB
 9 #NOTE: editnextlines with lys→arg positions
10 Replace Residue newmodel:118 lys L 11 Replace Residue newmodel:125 lys L
12 Replace Residue newmodel:133 lys L
13 Replace Residue newmodel:139 lys L
14 Replace Residue newmodel:160 lys L
15 Replace Residue newmodel:179 lys L
16 Replace Residue newmodel:209 lys L
17 #
18 #Now repeat analysis done prior to arg→lys, now including introduced lysines
19 Color Molecule Atoms newmodel Specified Specification 255,0,255
20 Zone Subset LYSx newmodel:lys:NZ Static monomer/residue 10 Color_Subset 255,255,0
21 Zone Subset NTERMx newmodel:1:N Static monomer/residue 10 Color_Subset 255,255,0
22 #NOTE: editnextline ACTSITEx residues according to the protein
23 Zone Subset ACTSITEx newmodel:146,201,258 Static monomer/residue 8 Color_Subset 255,255,0
24 Combine Subset ALLZONEx Union LYSx NTERMx
25 Combine Subset ALLZONEx Union ALLZONEx ACTSITEx
26 Combine Subset RESTX Difference newmodel ALLZONEx
27 List Subset RESTX Atom Output_File restxatom.list
28 List Subset RESTX monomer/residue Output_File restxmole.list
29 #
30 Color Molecule Atoms ACTSITEx Specified Specification 255,0,0
31 List Subset ACTSITEx Atom Output_File actsitexatom.list
32 List Subset ACTSITEx monomer/residue Output_File actsitexmole.list
33 #
34 #read restxatom.list or restxmole.list to identify sites for (not_arg)→lys subst. if needed Comments:

Of the residues in RESTX, the following are >5% exposed (see lists below): 18,31–33,36,38,40,48,50,56–62, 64,78,88,91–93,104–106,120,136,225,227–229,250,262, 268. Of these three are Cysteines involved in disulfide bridge formation, and consequently for structural reasons excluded from the residues to be mutated. The following mutations are proposed in *H. lanuginosa* lipase (TIB): A18K,G31K,T32K,N33K,G38K,A40K,D48K,T50K,E56K, D57K,S58K,G59K, V60K,G61K,D62K,T64K,L78K, N88K,G91K,N92K,L93K,S105K,G106K, V120K,P136K, G225K,L227K,V228K,P229K,P250K,F262K. Relevant data for Example 2:

| # TIBNOH2O | |
|---|---|
| # residue | area |
| GLU_1 | 110.792610 |
| VAL_2 | 18.002457 |
| SER_3 | 53.019516 |
| GLN_4 | 85.770164 |
| ASP_5 | 107.565826 |
| LEU_6 | 33.022659 |

-continued

| # TIBNOH2O | |
|---|---|
| # residue | area |
| PHE_7 | 34.392754 |
| ASN_8 | 84.855331 |
| GLN_9 | 39.175591 |
| PHE_10 | 2.149547 |
| ASN_11 | 40.544380 |
| LEU_12 | 27.648788 |
| PHE_13 | 2.418241 |
| ALA_14 | 4.625293 |
| GLN_15 | 28.202387 |
| TYR_16 | 0.969180 |
| SER_17 | 0.000000 |
| ALA_18 | 7.008336 |
| ALA_19 | 0.000000 |
| ALA_20 | 0.000000 |
| TYR_21 | 6.947358 |
| CYS_22 | 8.060802 |
| GLY_23 | 32.147034 |
| LYS_24 | 168.890747 |
| ASN_25 | 8.014721 |
| ASN_26 | 11.815564 |
| ASP_27 | 92.263428 |
| ALA_28 | 18.206699 |
| PRO_29 | 83.188431 |
| ALA_30 | 69.428421 |
| GLY_31 | 50.693439 |
| THR_32 | 52.171135 |
| ASN_33 | 111.230743 |
| ILE_34 | 2.801945 |
| THR_35 | 82.130569 |
| CYS_36 | 17.269245 |
| THR_37 | 96.731941 |
| GLY_38 | 77.870995 |
| ASN_39 | 123.051003 |
| ALA_40 | 27.985256 |
| CYS_41 | 0.752820 |
| PRO_42 | 46.258949 |
| GLU_43 | 69.773987 |
| VAL_44 | 0.735684 |
| GLU_45 | 77.169510 |
| LYS_46 | 141.213562 |
| ALA_47 | 10.249716 |
| ASP_48 | 109.913902 |
| ALA_49 | 2.602721 |
| THR_50 | 32.012184 |
| PHE_51 | 8.255627 |
| LEU_52 | 60.093613 |
| TYR_53 | 77.877937 |
| SER_54 | 26.980494 |
| PHE_55 | 10.747735 |
| GLU_56 | 112.689758 |
| ASP_57 | 92.064278 |
| SER_58 | 32.990780 |
| GLY_59 | 53.371807 |
| VAL_60 | 83.563644 |
| GLY_61 | 69.625633 |
| ASP_62 | 75.520988 |
| VAL_63 | 4.030401 |
| THR_64 | 8.652839 |
| GLY_65 | 0.000000 |
| PHE_66 | 0.268693 |
| LEU_67 | 11.822510 |
| ALA_68 | 0.537387 |
| LEU_69 | 30.243870 |
| ASP_70 | 0.000000 |
| ASN_71 | 84.101044 |
| THR_72 | 89.271126 |
| ASN_73 | 70.742401 |
| LYS_74 | 98.319168 |
| LEU_75 | 8.329495 |
| ILE_76 | 5.197878 |
| VAL_77 | 0.806080 |
| LEU_78 | 5.293978 |
| SER_79 | 0.000000 |
| PHE_80 | 2.079151 |
| ARG_81 | 41.085312 |

-continued

| # residue | # TIBNOH2O area |
|---|---|
| GLY_82 | 1.471369 |
| SER_83 | 43.794014 |
| ARG_84 | 100.26127 |
| SER_85 | 70.607552 |
| ILE_86 | 59.696865 |
| GLU_87 | 136.510773 |
| ASN_88 | 119.376373 |
| TRP_89 | 102.851227 |
| ILE_90 | 78.068588 |
| GLY_91 | 60.783607 |
| ASN_92 | 45.769428 |
| LEU_93 | 134.228363 |
| ASN_94 | 101.810959 |
| PHE_95 | 41.212212 |
| ASP_96 | 79.645950 |
| LEU_97 | 25.281572 |
| LYS_98 | 88.840263 |
| GLU_99 | 132.377090 |
| ILE_100 | 9.135575 |
| ASN_101 | 63.444527 |
| ASP_102 | 88.652847 |
| ILE_103 | 33.470661 |
| CYS_104 | 11.553816 |
| SER_105 | 99.461174 |
| GLY_106 | 40.325161 |
| CYS_107 | 4.433561 |
| ARG_108 | 97.450104 |
| GLY_109 | 1.343467 |
| HIS_110 | 4.652464 |
| ASP_111 | 37.023655 |
| GLY_112 | 29.930408 |
| PHE_113 | 14.976435 |
| THR_114 | 10.430954 |
| SER_115 | 40.606895 |
| SER_116 | 13.462922 |
| TRP_117 | 10.747735 |
| ARG_118 | 114.364281 |
| SER_119 | 46.880249 |
| VAL_120 | 13.434669 |
| ALA_121 | 18.258261 |
| ASP_122 | 110.753098 |
| THR_123 | 69.641922 |
| LEU_124 | 17.090784 |
| ARG_125 | 73.929977 |
| GLN_126 | 101.320190 |
| LYS_127 | 84.450241 |
| VAL_128 | 6.448641 |
| GLU_129 | 47.700993 |
| ASP_130 | 75.529091 |
| ALA_131 | 11.340775 |
| VAL_132 | 27.896025 |
| ARG_133 | 153.136490 |
| GLU_134 | 132.140594 |
| HIS_135 | 54.553406 |
| PRO_136 | 97.386963 |
| ASP_137 | 22.653191 |
| TYR_138 | 35.392658 |
| ARG_139 | 74.321243 |
| VAL_140 | 10.173222 |
| VAL_141 | 0.233495 |
| PHE_142 | 3.224321 |
| THR_143 | 0.000000 |
| GLY_144 | 0.000000 |
| HIS_145 | 4.514527 |
| SER_146 | 15.749787 |
| LEU_147 | 40.709171 |
| GLY_148 | 0.000000 |
| GLY_149 | 0.000000 |
| ALA_150 | 0.537387 |
| LEU_151 | 22.838938 |
| ALA_152 | 0.268693 |
| THR_153 | 18.078798 |
| VAL_154 | 7.254722 |
| ALA_155 | 0.000000 |
| GLY_156 | 0.000000 |

-continued

| # residue | # TIBNOH2O area |
|---|---|
| ALA_157 | 15.140230 |
| ASP_158 | 41.645477 |
| LEU_159 | 6.144750 |
| ARG_160 | 41.939716 |
| GLY_161 | 68.978180 |
| ASN_162 | 68.243805 |
| GLY_163 | 79.181274 |
| TYR_164 | 36.190247 |
| ASP_165 | 103.068283 |
| ILE_166 | 0.000000 |
| ASP_167 | 24.326443 |
| VAL_168 | 4.299094 |
| PHE_169 | 0.466991 |
| SER_170 | 3.339332 |
| TYR_171 | 0.000000 |
| GLY_172 | 0.000000 |
| ALA_173 | 12.674671 |
| PRO_174 | 13.117888 |
| ARG_175 | 10.004488 |
| VAL_176 | 21.422220 |
| GLY_177 | 2.680759 |
| ASN_178 | 21.018063 |
| ARG_179 | 110.282166 |
| ALA_180 | 33.210381 |
| PHE_181 | 4.567788 |
| ALA_182 | 3.897251 |
| GLU_183 | 76.354004 |
| PHE_184 | 71.225983 |
| LEU_185 | 24.985012 |
| THR_186 | 47.023815 |
| VAL_187 | 98.244606 |
| GLN_188 | 54.152954 |
| THR_189 | 88.660645 |
| GLY_190 | 24.792120 |
| GLY_191 | 10.726818 |
| THR_192 | 45.458744 |
| LEU_193 | 16.633211 |
| TYR_194 | 34.829491 |
| ARG_195 | 29.030851 |
| ILE_196 | 1.973557 |
| THR_197 | 3.493014 |
| HIS_198 | 1.532270 |
| THR_199 | 34.785877 |
| ASN_200 | 39.789238 |
| ASP_201 | 0.000000 |
| ILE_202 | 31.168434 |
| VAL_203 | 29.521076 |
| PRO_204 | 3.515322 |
| ARG_205 | 44.882454 |
| LEU_206 | 51.051746 |
| PRO_207 | 12.575329 |
| PRO_208 | 43.259636 |
| ARG_209 | 113.700233 |
| GLU_210 | 154.628540 |
| PHE_211 | 112.505188 |
| GLY_212 | 30.084938 |
| TYR_213 | 3.268936 |
| SER_214 | 12.471436 |
| HIS_215 | 23.354481 |
| SER_216 | 16.406200 |
| SER_217 | 14.665598 |
| PRO_218 | 17.240993 |
| GLU_219 | 13.145291 |
| TYR_220 | 18.718306 |
| TRP_221 | 39.229233 |
| ILE_222 | 5.105175 |
| LYS_223 | 120.739983 |
| SER_224 | 15.407301 |
| GLY_225 | 29.306646 |
| THR_226 | 66.806862 |
| LEU_227 | 122.682808 |
| VAL_228 | 60.923004 |
| PRO_229 | 104.620377 |
| VAL_230 | 23.398251 |
| THR_231 | 63.372971 |

-continued

| # TIBNOH2O | |
|---|---|
| # residue | area |
| ARG__232 | 80.357857 |
| ASN__233 | 89.255066 |
| ASP__234 | 43.011250 |
| ILE__235 | 2.114349 |
| VAL__236 | 45.140491 |
| LYS__237 | 105.651306 |
| ILE__238 | 24.671705 |
| GLU__239 | 116.891907 |
| GLY__240 | 31.965794 |
| ILE__241 | 46.278099 |
| ASP__242 | 28.963699 |
| ALA__243 | 25.158146 |
| THR__244 | 98.351440 |
| GLY__245 | 43.842186 |
| GLY__246 | 0.700486 |
| ASN__247 | 3.926274 |
| ASN__248 | 51.047890 |
| GLN__249 | 66.699188 |
| PRO__250 | 132.414047 |
| ASN__251 | 70.213730 |
| ILE__252 | 141.498062 |
| PRO__253 | 59.089233 |
| ASP__254 | 59.010895 |
| ILE__255 | 63.298943 |
| PRO__256 | 78.608688 |
| ALA__257 | 0.806080 |
| HIS__258 | 3.761708 |
| LEU__259 | 50.747856 |
| TRP__260 | 35.229710 |
| TYR__261 | 5.440791 |
| PHE__262 | 36.457939 |
| GLY__263 | 22.071375 |
| LEU__264 | 109.148178 |
| ILE__265 | 2.418241 |
| GLY__266 | 17.730062 |
| THR__267 | 68.217873 |
| CYS__268 | 15.418195 |
| LEU__269 | 165.990997 |

Subset REST:
 restmole.list
Subset REST:
 TIB:5,8–9,13–14,16,18–20,31–34,36,38,40,48–80,
  56–66,68,76–79,88,91–93,
 TIB:100–107,116–117,119–121,132–134,136,139–142,
  154–40 169,177–185,
 TIB:187,189–191,207–212,214–216,225,227–229,
  241–244,250,262,268
 restatom.list
Subset REST:
 TIB:ASP 5:N,CA,C,O,CB,CG,OD1,OD2
 TIB:ASN 8:N,CA,C,O,CB,CG,OD1,ND2
 TIB:GLN 9:N,CA,C,O,CB,CG,CD,OE1,NE2
 TIB:PHE 13:N,CA,C,O,CB,CG,CD1,CD2,CE1,CE2,CZ
 TIB:ALA 14:N,CA,C,0,CB
 TIB:TYR 16:N,CA,C,O,CB,CG,CD1,CD2,CE1,CE2,CZ,
  OH
 TIB:ALA 18:N,CA,C,0,CB
 TIB:ALA 19:N,CA,C,O,CB
 TIB:ALA 20:N,CA,C,O,CB
 TIB:GLY 31:N,CA,C,O
 TIB:THR 32:N,CA,C,O,CB,OG1,CG2
 TIB:ASN 33:N,CA,C,O,CB,CG,OD1,ND2
 TIB:ILE 34:N,CA,C,O,CB,CG1,CG2,CD1
 TIB:CYS 36:N,CA,C,O,CB,SG
 TIB:GLY 38:N,CA,C,O
 TIB:ALA 40:N,CA,C,O,CB
 TIB:ASP 48:N,CA,C,O,CB,CG,OD1,OD2
 TIB:ALA 49:N,CA,C,O,CB
 TIB:THR 50:N,CA,C,O,CB,OG1,CG2
 TIB:GLU 56:N,CA,C,O,CB,CG,CD,OE1,OE2
 TIB:ASP 57:N,CA,C,O,CB,CG,OD1,OD2
 TIB:SER 58:N,CA,C,O,CB,OG
 TIB:GLY 59:N,CA,C,O
 TIB:VAL 60:N,CA,C,O,CB,CG1,CG2
 TIB:GLY 61:N,CA,C,O
 TIB:ASP 62:N,CA,C,O,CB,CG,OD1,OD2
 TIB:VAL 63:N,CA,C,O,CB,CG1,CG2
 TIB:THR 64:N,CA,C,O,CB,OG1,CG2
 TIB:GLY 65:N,CA,C,O
 TIB:PHE 66:N,CA,C,O,CB,CG,CD1,CD2,CE1,CE2,CZ
 TIB:ALA 68:N,CA,C,O,CB
 TIB:ILE 76:N,CA,C,O,CB,CG1,CG2,CD1
 TIB:VAL 77:N,CA,C,O,CB,CG1,CG2
 TIB:LEU 78:N,CA,C,O,CB,CG,CD1,CD2
 TIB:SER 79:N,CA,C,O,CB,OG
 TIB:ASN 88:N,CA,C,O,CB,CG,OD1,ND2
 TIB:GLY 91:N,CA,C,O
 TIB:ASN 92:N,CA,C,O,CB,CG,OD1,ND2
 TIB:LEU 93:N,CA,C,O,CB,CG,CD1,CD2
 TIB:ILE 100:N,CA,C,O,CB,CG1,CG2,CD1
 TIB:ASN 101:N,CA,C,O,CB,CG,OD1,ND2
 TIB:ASP 102:N,CA,C,O,CB,CG,OD1,OD2
 TIB:ILE 103:N,CA,C,O,CB,CG1,CG2,CD1
 TIB:CYS 104:N,CA,C,O,CB,SG
 TIB:SER 105:N,CA,C,O,CB,OG
 TIB:GLY 106:N,CA,C,O
 TIB:CYS 107:N,CA,C,O,CB,SG
 TIB:SER 116:N,CA,C,O,CB,OG
 TIB:TRP 117:N,CA,C,O,CB,CG,CD1,CD2,NE1,CE2,
  CE3,CZ2,CZ3,CH2
 TIB:SER 119:N,CA,C,O,CB,OG
 TIB:VAL 120:N,CA,C,O,CB,CG1,CG2
 TIB:ALA 121:N,CA,C,O,CB
 TIB:VAL 132:N,CA,C,O,CB,CG1,CG2
 TIB:ARG 133:N,CA,C,O,CB,CG,CD,NE,CZ,NH1,NH2
 TIB:GLU 134:N,CA,C,O,CB,CG,CD,OE1,OE2
 TIB:PRO 136:N,CA,CD,C,O,CB,CG
 TIB:ARG 139:N,CA,C,O,CB,CG,CD,NE,CZ,NH1,NH2
 TIB:VAL 140:N,CA,C..,O,CB,CG1,CG2
 TIB:VAL 141:N,CA,C,O,CB,CG1,CG2
 TIB:PHE 142:N,CA,C,O,CB,CG,CD1,CD2,CE1,CE2,
  CZ
 TIB:VAL 154:N,CA,C,O,CB,CG1,CG2
 TIB:ALA 155:N,CA,C,O,CB
 TIB:GLY 156:N,CA,C,O
 TIB:ALA 157:N,CA,C,O,CB
 TIB:ASP 158:N,CA,C,O,CB,CG,OD1,OD2
 TIB:LEU 159:N,CA,C,O,CB,CG,CD1,CD2
 TIB:ARG 160:N,CA,C,O,CB,CG,CD,NE,CZ,NH1,NH2
 TIB:GLY 161:N,CA,C,O
 TIB:ASN 162:N,CA,C,O,CB,CG,OD1,ND2

TIB:GLY 163:N,CA,C,O
TIB:TYR 164:N,CA,C,O,CB,CG,CD1,CD2,CE1,CE2,CZ,OH
TIB:ASP 165:N,CA,C,O,CB,CG,OD1,OD2
TIB:ILE 166:N,CA,C,O,CB,CG1,CG2,CD1
TIB:ASP 167:N,CA,C,O,CB,CG,OD1,OD2
TIB:VAL 168:N,CA,C,O,CB,CG1,CG2
TIB:PHE 169:N,CA,C,O,CB,CG,CD1,CD2,CE1,CE2,CZ
TIB:GLY 177:N,CA,C,O
TIB:ASN 178:N,CA,C,O,CB,CG,OD1,ND2
TIB:ARG 179:N,CA,C,O,CB,CG,CD,NE,CZ,NH1,NH2
TIB:ALA 180:N,CA,C,O,CB
TIB:PHE 181:N,CA,C,O,CB,CG,CD1,CD2,CE1,CE2,CZ
TIB:ALA 182:N,CA,C,O,CB
TIB:GLU 183:N,CA,C,O,CB,CG,CD,OE1,OE2
TIB:PHE 184:N,CA,C,O,CB,CG,CD1,CD2,CE1,CE2,CZ
TIB:LEU 185:N,CA,C,O,CB,CG,CD1,CD2
TIB:VAL 187:N,CA,C,O,CB,CG1,CG2
TIB:THR 189:N,CA,C,O,CB,OG1,CG2
TIB:GLY 190:N,CA,C,O
TIB:GLY 191:N,CA,C,O
TIB:PRO 207:N,CA,CD,C,O,CB,CG
TIB:PRO 208:N,CA,CD,C,O,CB,CG
TIB:ARG 209:N,CA,C,O,CB,CG,CD,NE,CZ,NH1,NH2
TIB:GLU 210:N,CA,C,O,CB,CG,CD,OE1,OE2
TIB:PHE 211:N,CA,C,O,CB,CG,CD1,CD2,CE1,CE2,CZ
TIB:GLY 212:N,CA,C,O
TIB:SER 214:N,CA,C,O,CB,OG
TIB:HIS 215:N,CA,C,O,CB,CG,ND1,CD2,CE1,NE2
TIB:SER 216:N,CA,C,O,CB,OG
TIB:GLY 225:N,CA,C,O
TIB:LEU 227:N,CA,C,O,CB,CG,CD1,CD2
TIB:VAL 228:N,CA,C,O,CB,CG1,CG2
TIB:PRO 229:N,CA,CD,C,O,CB,CG
TIB:ILE 241:N,CA,C,O,CB,CG1,CG2,CD1
TIB:ASP 242:N,CA,C,O,CB,CG,OD1,OD2
TIB:ALA 243:N,CA,C,O,CB
TIB:THR 244:N,CA,C,O,CB,OG1,CG2
TIB:PRO 250:N,CA,CD,C,O,CB,CG
TIB:PHE 262:N,CA,C,O,CB,CG,CD1,CD2,CE1,CE2,CZ
TIB:CYS 268:N,CA,C,O,CB,SG
Subset SUB5B:
sub5mole.list
Subset SUB5B:
TIB:3–4,6–7,10–12,15,22–23,25–30,35,37,39,41–42,44–47,51–55,67,69–70,
TIB:72,74–75,94–99,108–112,114–115,118,122–126,128–131,135,137–138,
TIB:186,188,192–195,213,217–219,223–224,230–231,234–235,238–240,
TIB:245,269
sub5batom.list Subset SUB5B:
TIB:SER 3:N,CA,C,O,CB,OG
TIB:GLN 4:N,CA,C,O,CB,CG,CD,OE1,NE2
TIB:LEU 6:N,CA,C,O,CB,CG,CD1,CD2
TIB:PHE 7:N,CA,C,O,CB,CG,CD1,CD2,CE1,CE2,CZ
TIB:PHE 10:N,CA,C,O,CB,CG,CD1,CD2,CE1,CE2,CZ
TIB:ASN 11:N,CA,C,O,CB,CG,OD1,ND2
TIB:.LEU 12:N,CA,C,O,CB,CG,CD1,CD2
TIB:GLN 15:N,CA,C,O,CB,CG,CD,OE1,NE2
TIB:CYS 22:N,CA,C,O,CB,SG
TIB:GLY 23:N,CA,C,O
TIB:ASN 25:N,CA,C,O,CB,CG,OD1,ND2
TIB:ASN 26:N,CA,C,O,CB,CG,OD1,ND2
TIB:ASP 27:N,CA,C,0,CB,CG,OD1,OD2
TIB:ALA 28:N,CA,C,O,CB
TIB:PRO 29:N,CA,CD,C,O,CB,CG
TIB:ALA 30:N,CA,C,O,CB
TIB:THR 35:N,CA,C,O,CB,OG1,CG2
TIB:THR 37:N,CA,C,O,CB,OG1,CG2
TIB:ASN 39:N,CA,C,O,CB,CG,OD1,ND2
TIB:CYS 41:N,CA,C,O,CB,SG
TIB:PRO 42:N,CA,CD,C,O,CB,CG
TIB:VAL 44:N,CA,C,O,CB,CG1,CG2
TIB:GLU-45:N,CA,C,O,CB,CG,CD,OE1,OE2
TIB:LYS 46:N,CA,C,O,CB,CG,CD,CE,NZ
TIB:ALA 47:N,CA,C,O,CB
TIB:PHE 51:N,CA,C,O,CB,CG,CD1,CD2,CE1,CE2,CZ
TIB:LEU 52:N,CA,C,O,CB,CG,CD1,CD2
TIB:TYR 53:N,CA,C,O;CB,CG,CD1,CD2,CE1,CE2,CZ,OH
TIB:SER 54:N,CA,C,O,CB,OG
TIB:PHE 55:N,CA,C,O,CB,CG,CD1,CD2,CE1,CE2,CZ
TIB:LEU 67:N,CA,C,O,CB,CG,CD1,CD2
TIB:LEU 69:N,CA,C,O,CB,CG,CD1,CD2
TIB:ASP 70:N,CA,C,O,CB,CG,OD1,OD2
TIB:THR 72:N,CA,C,O,CB,OG1,CG2
TIB:LYS 74:N,CA,C,O,CB,CG,CD,CE,NZ
TIB:LEU 75:N,CA,C,O,CB,CG,CD1,CD2
TIB:ASN 94:N,CA,C,O,CB,CG,OD1,ND2
TIB:PHE 95:N,CA,C,O,CB,CG,CD1,CD2,CE1,CE2,CZ
TIB:ASP 96:N,CA,C,O,CB,CG,OD1,OD2
TIB:LEU 97:N,CA,C,O,CB,CG,CD1,CD2
TIB:LYS 98:N,CA,C,O,CB,CG,CD,CE,NZ
TIB:GLU 99:N,CA,C,O,CB,CG,CD,OE1,OE2
TIB:ARG 108:N,CA,C,O,CB,CG,CD,NE,CZ,NH1,NH2
TIB:GLY 109:N,CA,C,O
TIB:HIS 110:N,CA,C,O,CB,CG,ND1,CD2,CE1,NE2
TIB:ASP 111:N,CA,C,O,CB,CG,OD1,OD2
TIB:GLY 112:N,CA,C,O
TIB:THR 114:N,CA,C,O,CB,OG1,CG2
TIB:SER 115:N,CA,C,O,CB,OG
TIB:ARG 118:N,CA,C,O,CB,CG,CD,NE,CZ,NH1,NH2
TIB:ASP 122:N,CA,C,O,CB,CG,OD1,OD2
TIB:THR 123:N,CA,C,O,CB,OG1,CG2
TIB:LEU 124:N,CA,C,O,CB,CG,CD1,CD2
TIB:ARG 125:N,CA,C,O,CB,CG,CD,NE,CZ,NH1,NH2
TIB:GLN 126:N,CA,C,O,CB,CG,CD,OE1,NE2

TIB:VAL 128:N,CA,C,O,CB,CG1,CG2
TIB:GLU 129:N,CA,C,O,CB,CG,CD,OE1,OE2
TIB:ASP 130:N,CA,C,O,CB,CG,OD1,OD2
TIB:ALA 131:N,CA,C,O,CB
TIB:HIS 135:N,CA,C,O,CB,CG,ND1,CD2,CE1,NE2
TIB:ASP 137:N,CA,C,O,CB,CG,OD1,OD2
TIB:TYR 138:N,CA,C,O,CB,CG,CD1,CD2,CE1,CE2,CZ,OH
TIB:THR 186:N,CA,C,O,CB,OG1,CG2
TIB:GLN 188:N,CA,C,O,CB,CG,CD,OE1,NE2
TIB:THR 192:N,CA,C,O,CB,OG1,CG2
TIB:LEU 193:N,CA,C,O,CB,CG,CD1,CD2
TIB:TYR 194:N,CA,C,O,CB,CG,CD1,CD2,CE1,CE2,CZ,OH
TIB:ARG 195:N,CA,C,O,CB,CG,CD,NE,CZ,NH1,NH2
TIB:TYR 213:N,CA,C,O,CB,CG,CD1,CD2,CE1,CE2,CZ,OH
TIB:SER 217:N,CA,C,O,CB,OG
TIB:PRO 218:N,CA,CD,C,O,CB,CG
TIB:GLU 219:N,CA,C,O,CB,CG,CD,OE1,OE2
TIB:LYS 223:N,CA,C,O,CB,CG,CD,CE,NZ
TIB:SER 224:N,CA,C,O,CB,OG
TIB:VAL 230:N,CA,C,O,CB,CG1,CG2
TIB:THR 231:N,CA,C,O,CB,OG1,CG2
TIB:ASP 234:N,CA,C,O,CB,CG,OD1,OD2
TIB:ILE 235:N,CA,C,O,CB,CG1,CG2,CD1
TIB:ILE 238:N,CA,C,O,CB,CG1,CG2,CD1
TIB:GLU 239:N,CA,C, 0,CB,CG,CD,OE1,OE2
TIB:GLY 240:N,CA,C,O
TIB:GLY 245:N,CA,C,O
TIB:LEU 269:N,CA,C,O,CB,OXT,CG,CD1,CD2
Subset ACTSITE:
actsitemole.list
Subset ACTSITE:
TIB:17,21,80–87,89–90,113,143–153,170–176,196–206,221–222,226,246–249,
TIB:251–261,263–267
actsiteatom.list
Subset ACTSITE:
TIB:SER 17:N,CA,C,0,CB,OG
TIB:TYR 21:N,CA,C,O,CB,CG,CD1,CD2,CE1,CE2,CZ,OH
TIB:PHE 80:N,CA,C,O,CB,CG,CD1,CD2,CE1,CE2,CZ
TIB:ARG 81:N,CA,C,O,CB,CG,CD,NE,CZ,NH1,NH2
TIB:GLY 82:N,CA,C,O
TIB:SER 83:N,CA,C,O,CB,OG
TIB:ARG 84:N,CA,C,O,CB,CG,CD,NE,CZ,NH1,NH2
TIB:SER 85:N,CA,C,O,CB,OG
TIB:ILE 86:N,CA,C,O,CB,CG1,CG2,CD1
TIB:GLU 87:N,CA,C,O,CB,CG,CD,OE1,OE2
TIB:TRP 89:N,CA,C,O,CB,CG,CD1,CD2,NE1,CE2,CE3,CZ2,CZ3,CH2
TIB:ILE 90:N,CA,C,O,CB,CG1,CG2,CD1
TIB:PHE 113:N,CA,C,O,CB,CG,CD1,CD2,CE1,CE2,CZ
TIB:THR 143:N,CA,C,O,CB,OG1,CG2
TIB:GLY 144:N,CA,C,O
TIB:HIS 145:N,CA,C,O,CB,CG,ND1,CD2,CE1,NE2
TIB:SER 146:N,CA,C,O,CB,OG
TIB:LEU 147:N,CA,C,O,CB,CG,CD1,CD2
TIB:GLY 148:N,CA,C,O
TIB:GLY 149:N,CA,C,O
TIB:ALA 150:N,CA,C,O,CB
TIB:LEU 151:N,CA,C,O,CB,CG,CD1,CD2
TIB:ALA 152:N,CA,C,O,CB
TIB:THR 153:N,CA,C,O,CB,OG1,CG2
TIB:SER 170:N,CA,C,O,CB,OG
TIB:TYR 171:N,CA,C,O,CB,CG,CD1,CD2,CE1,CE2,CZ,OH
TIB:GLY 172:N,CA,C,O
TIB:ALA 173:N,CA,C,O,CB
TIB:PRO 174:N,CA,CD,C,O,CB,CG
TIB:ARG 175:N,CA,C,O,CB,CG,CD,NE,CZ,NH1,NH2
TIB:VAL 176:N,CA,C,O,CB,CG1,CG2
TIB:ILE 196:N,CA,C,O,CB,CG1,CG2,CD1
TIB:THR 197:N,CA,C,O,CB,OG1,CG2
TIB:HIS 198:N,CA,C,00CB,CG,ND1,CD2,CE1,NE2
TIB:THR 199:N,CA,C,O,CB,OG1,CG2
TIB:ASN 200:N,CA,C,O,CB,CG,OD1,ND2
TIB:ASP 201:N,CA,C,O,CB,CG,OD1,OD2
TIB:ILE 202:N,CA,C,O,CB,CG1,CG2,CD1
TIB:VAL 203:N,CA,C,O,CB,CG1,CG2
TIB:PRO 204:N,CA,CD,C,O,CB,CG
TIB:ARG 205:N,CA,C,O,CB,CG,CD,NE,CZ,NH1,NH2
TIB:LEU 206:N,CA,C,O,CB,CG,CD1,CD2
TIB:TRP 221:N,CA,C,O,CB,CG,CD1,CD2,NE1,CE2,CE3,CZ2,CZ3,CH2
TIB:ILE 222:N,CA,C,O,CB,CG1,CG2,CD1
TIB:THR 226:N,CA,C,O,CB,OG1,CG2
TIB:GLY 246:N,CA,C,O
TIB:ASN 247:N,CA,C,O,CB,CG,OD1,ND2
TIB:ASN 248:N,CA,C,O,CB,CG,OD1,ND2
TIB:GLN 249:N,CA,C,O,CB,CG,CD,OE1,NE2
TIB:ASN 251:N,CA,C,O,CB,CG,OD1,ND2
TIB:ILE 252:N,CA,C,O,CB,CG1,CG2,CD1
TIB:PRO 253:N,CA,CD,C,O,CB,CG
TIB:ASP 254:N,CA,C,O,CB,CG,OD1,OD2
TIB:ILE 255:N,CA,C,O,CB,CG1,CG2,CD1
TIB:PRO 256:N,CA,CD,C,O,CB,CG
TIB:ALA 257:N,CA,C,O,CB
TIB:HIS 258:N,CA,C,O,CB,CG,ND1,CD2,CE1,NE2
TIB:LEU 259:N,CA,C,O,CB,CG,CD1,CD2
TIB:TRP 260:N,CA,C,O,CB,CG,CD1,CD2,NE1,CE2,CE3,CZ2,CZ3,CH2
TIB:TYR 261:N,CA,C,O,CB,CG,CD1,CD2,CE1,CE2,CZ,OH
TIB:GLY 263:N,CA,C,O
TIB:LEU 264:N,CA,C,O,CB,CG,CD1,CD2
TIB:ILE 265:N,CA,C,O,CB,CG1,CG2,CD1
TIB:GLY 266:N,CA,C,O
TIB:THR 267:N,CA,C,O,CB,OG1,CG2
Subset RESTX:
restxmole.list
Subset RESTX:
NEWMODEL:14,16,18–20,31–34,36,38,40,48–50,56–66,68,78–79,88,91–93, NEWMODEL:104–106,120,136,225,227–229,250,262, 268
restxatom.list
Subset RESTX:
NEWMODEL:ALA 14:N,CA,C,O,CB
NEWMODEL:TYR 16:N,CA,C,O,CB,CG,CD1,CD2, CE1,CE2,CZ,OH
NEWMODEL:ALA 18:N,CA,C,O,CB
NEWMODEL:ALA 19:N,CA,C,O,CB
NEWMODEL:ALA 20:N,CA,C,O,CB
NEWMODEL:GLY 31:N,CA,C,O
NEWMODEL:THR 32:N,CA,C,O,CB,OG1,CG2
NEWMODEL:ASN 33:N,CA,C,O,CB,CG,OD1,ND2
NEWMODEL:ILE 34:N,CA,C,O,CB,CG1,CG2,CD1
NEWMODEL:CYS 36:N,CA,C,O,CB,SG
NEWMODEL:GLY 38:N,CA,C,O
NEWMODEL:ALA 40:N,CA,C,O,CB
NEWMODEL:ASP 48:N,CA,C,O,CB,CG,OD1,OD2
NEWMODEL:ALA 49:N,CA,C,O,CB
NEWMODEL:THR 50:N,CA,C,O,CB,OG1,CG2
NEWMODEL:GLU 56:N,CA,C,O,CB,CG,CD,OE1,OE2
NEWMODEL:ASP 57:N,CA,C,O,CB,CG,OD1,OD2
NEWMODEL:SER 58:N,CA,C,O,CB,OG
NEWMODEL:GLY 59:N,CA,C,O
NEWMODEL:VAL 60:N,CA,C,O,CB,CG1,CG2
NEWMODEL:GLY 61:N,CA,C,O
NEWMODEL:ASP 62:N,CA,C,O,CB,CG,OD1,OD2
NEWMODEL:VAL 63:N,CA,C,O,CB,CG1,CG2
NEWMODEL:THR 64:N,CA,C,O,CB,OG1,CG2
NEWMODEL:GLY 65:N,CA,C,O
NEWMODEL:PHE 66:N,CA,C,O,CB,CG,CD1,CD2, CE1,CE2,CZ
NEWMODEL:ALA 68:N,CA,C,O,CB
NEWMODEL:LEU 78:N,CA,C,O,CB,CG,CD1,CD2
NEWMODEL:SER 79:N,CA,C,O,CB,OG
NEWMODEL:ASN 88:N,CA,C,O,CB,CG,OD1,ND2
NEWMODEL:GLY 91:N,CA,C,O
NEWMODEL:ASN 92:N,CA,C,O,CB,CG,OD1,ND2
NEWMODEL:LEU 93:N,CA,C,O,CB,CG,CD1,CD2
NEWMODEL:CYS 104:N,CA,C,O,CB,SG
NEWMODEL:SER 105:N,CA,C,O,CB,OG
NEWMODEL:GLY 106:N,CA,C,O
NEWMODEL:VAL 120:N,CA,C,O,CB,CG1,CG2
NEWMODEL:PRO 136:N,CA,CD,C,O,CB,CG
NEWMODEL:GLY 225:N,CA,C,O
NEWMODEL:LEU 227:N,CA,C,O,CB,CG,CD1,CD2
NEWMODEL:VAL 228:N,CA,C,O,CB,CG1,CG2
NEWMODEL:PRO 229:N,CA,CD,C,O,CB,CG
NEWMODEL:PRO 250:N,CA,CD,C,O,CB,CG
NEWMODEL:PHE 262:N,CA,C,O,CB,CG,CD1,CD2, CE1,CE2,CZ
NEWMODEL:CYS 268:N,CA,C,O,CB,SG Example 10

Providing a Lipase Variant E87K+D254K

The *Humicola lanuginosa* lipase variant E87K+D254K was constructed, expressed and purified as described in WO 92/05249.

Example 11

Lipase-S-PEG 15,000 Conjugate

The lipase variant E87K+D254K-SPEG conjugate was prepared as described in Example 7, except that the enzyme is the *Humicola lanuginosa* lipase variant (E87K+D254K) described in Example 10 and the polymer is mPEG15,000.

Example 12

Immunogenecity Assessed as IgG, of Lipase Variant (D87K+D254K) in Balb/C Mice

Balb/c mice were immunized by subcutanuous injection of:

i) 50 μl 0.9% (wt/vol) NaCl solution (control group, 8 mice) (control), ii) 50 μl 0.9% (wt/vol) NaCl solution containing 25 μg of protein of a *Humicola lanuginosa* lipase variant (E87K+D254K) (group 1, 8 mice) (unmodified lipase variant), iii) 50% 0.9% (wt/vol) NaCl solution containing a *Humicola lanugoinosa* lipase variant substituted in position D87K+D254K and coupled to a N-succinimidyl carbonate activated mPEG 15,000(group 2, 8 mice) (lipase-SPEG15,000).

The amount of protein for each batch was measured by optical density measurements. Blood samples (200 pl) were collected from the eyes one week after the immunization, but before the following immunization. Serum was obtained by blood clotting, and centrifugation.

The IgG$_1$ response was determined by use of the Balb/C mice IgG, ELISA method as described above.

Results:

Five weekly immunizations were required to elicit a detectable humoral response to the unmodified *Humicola lanuginosa* variant. The antibody titers elicited by the conjugate (i.e. lipase-SPEG15,000 ranged between 960 and 1920, and were only 2 to 4x lower than the antibody titer of 3840 that was elicited by unmodified HL82-Lipolase (figure to the left).

The Results of the Tests are Shown in FIG. 1

As will be apparent to those skilled in the art, in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A conjugate comprising a protease moiety conjugated to one or more polymers, wherein the protease moiety is a *Bacillus lentus* protease comprising one or more of the following substitutions: P5K, R10K, R19K, H39K, P40K, L42K, L75K, N76K, L82K, P86K, S103K, V104K, S105K, A108K, A133K, T134K, L135K, R145K, R170K, R186K, Q206K, G211K, S212K, A215K, S216K, R247K and N269K, wherein the positions are numbered according to the amino acid sequence of the mature subtilisin BPN'.

2. The conjugate of claim 1, wherein the protease has an amino acid sequence of SEQ ID NO: 3.

3. The conjugate of claim 1, wherein the polymer(s) have a molecular weight from 1 to 60 kDa.

4. The conjugate of claim 1, wherein the polymer(s) are natural or synthetic homo- or heteropolymers.

5. The conjugate of claim 1, wherein the polymer(s) are selected from the group consisting of polyols, polyamines, polycarboxyl acids and polymers comprising a hydroxyl group and an amine group.

6. The conjugate of claim 1, wherein the polymer(s) are selected from the group consisting of polyalkylene oxides (PAO), PEG-glycidyl ethers (Epox-PEG), PEG-oxycarbonylimidazole (CDI-PEG), branched PEGs, polyvinyl alcohols (PVA), poly-carboxylates, polyvinylpyrolidones, poly-D,L-amino acids, polyethylene-co-maleic acid anhydride, polystyrene-co-malic acid anhydrides, dextrans, heparins, homologous albumins, celluloses, hydrolysates of chitosan, starches, glycogen, agaroses and derivatives thereof, guar gum, pullulan, inulin, xanthan gum, carrageenin, pectin, alginic acid hydrolysates and bio-polymers.

7. The conjugate of claim 1, wherein the polymer(s) are polyalkylene glycols (PAG) or methoxypolyethylene glycols (mPEG).

8. The conjugate of claim 1, wherein the polymer(s) are selected from the group consisting of polyethylene glycols (PEG), polypropylene glycols and carboxymethyl-dextrans.

9. The conjugate of claim 1, wherein the polymer(s) are selected from the group consisting of methylcellulose, carboxymethylcellulose, ethylcellulose, hydroxyethylcellulose carboxyethylcellulose and hydroxypropylcellulose.

10. The conjugate of claim 1, wherein the polymer(s) are hydroxyethyl-starches or hydroxypropyl-starches.

11. The conjugate of claim 1, wherein the polymer(s) are methoxypolyethylene glycols (mPEG).

* * * * *